US009303071B2

(12) United States Patent
Simard et al.

(10) Patent No.: US 9,303,071 B2
(45) Date of Patent: Apr. 5, 2016

(54) SALMONID ALPHAVIRUS AND USES THEREOF

(71) Applicant: Novartis Tiergesundheit AG, Basel (CH)

(72) Inventors: Nathalie Simard, Basel (CH); Michael Horne, Basel (CH)

(73) Assignee: Novartis Tiergesundheit AG, Basel (CH)

( * ) Notice: Subject to any disclaimer, the term of this patent is extended or adjusted under 35 U.S.C. 154(b) by 0 days.

(21) Appl. No.: 14/421,276

(22) PCT Filed: Sep. 17, 2013

(86) PCT No.: PCT/EP2013/069241
§ 371 (c)(1),
(2) Date: Feb. 12, 2015

(87) PCT Pub. No.: WO2014/041189
PCT Pub. Date: Mar. 20, 2014

(65) Prior Publication Data
US 2015/0232515 A1    Aug. 20, 2015

(30) Foreign Application Priority Data

Sep. 17, 2012  (EP) .................................... 12184758

(51) Int. Cl.
| C07K 14/005 | (2006.01) |
| A61K 39/12 | (2006.01) |
| C12N 7/00 | (2006.01) |
| A61K 39/00 | (2006.01) |

(52) U.S. Cl.
CPC ............... *C07K 14/005* (2013.01); *A61K 39/12* (2013.01); *C12N 7/00* (2013.01); *A61K 2039/53* (2013.01); *A61K 2039/552* (2013.01); *C12N 2770/36122* (2013.01); *C12N 2770/36134* (2013.01)

(58) Field of Classification Search
None
See application file for complete search history.

(56) References Cited

FOREIGN PATENT DOCUMENTS

| GB | 2457158 A | 12/2009 |
| WO | 8806626 | 9/1988 |
| WO | 9000594 | 1/1990 |
| WO | 9014363 | 11/1990 |
| WO | 9113157 | 9/1991 |
| WO | 9201796 | 2/1992 |
| WO | 9221376 | 12/1992 |

OTHER PUBLICATIONS

Weston, Salmon Pancreas Disease Virus, an Alphavirus Infecting Farmed Atlantic Salmon, Salmo salar L., Virology 1999, pp. 188-195, vol. 256.
Widera, Increased DNA Vaccine Delivery and Immunogenicity by Electroporation In Vivo, Immunology, 2000, pp. 4625-4640, vol. 164.
Xiang, Manipulation of the Immune Response to a Plasmid-Encoded Viral Antigen by Coinoculation with Plasmids Expressing Cokines, Immunity, 1995, pp. 129-135, vol. 2.
Xu, Superior protection conferred by inactivated whole virus vaccine over subunit and DNA vaccines against salmonid alphavirus infection in Atlantic salmon (Salmo salar L), Vaccine, 2012, pp. 3918-3928, vol. 30.
Cole, The EBV-Hybridoma Technique and Its Application to Human Lung Cancer, Monoclonal Antibodies and Cancer Therapy, 1985, pp. 77-96.
Longberg, Human Antibodies from Transgenic Mice, Intern. Rev. Immunol., pp. 63-93, vol. 13, 1995.
Weston, Comparison of Two Aquatic Alphaviruses, Salmon Pancreas Disease Virus and Sleeping Disease Virus, by Using Genome Sequence Analysis, Monoclonal Reactivity, and Cross-Infection, Journal of Virology, Jun. 2002, pp. 6155-6163. vol. 76, No. 12.
Database UNIPROTKB Q8QL52 2015.
Database UNIPROTKB M4M589 2015.
AMARA, Control of a Mucosal Challenge and Prevention of AIDS by a Multiprotein DNA/MVA Vaccine, Science, Apr. 2001, pp. 69-74, vol. 292.
Boerner, Production of Antigen-Specific Human Monoclonal Antibodies from In Vitro-Primed Human Splenocytes, The Journal of Immunology, Jul. 1991, pp. 86-95, vol. 147.
Bolivar, Construction and Characterization of new Cloning Vehicle, Gene, 1977, pp. 75-93, vol. 2.
Bolivar, Construction and Characterization of new Cloning Vehicle, Gene, 1977, pp. 95-113, vol. 2.
Caley, Venezuelan equine encephalitis virus vectors expressing HIV-1 proteins: vector design strategies for improved vaccine efficacy, Vaccine, 1999, pp. 3124-3135, vol. 17.
Covarrubias, Construction and characterization of new cloning vehicles, Gene, 1981, pp. 25-35, vol. 13.
Dubensky, Delivery Systems for Gene-based Vaccines, Molecular Medicine, 2000, pp. 723-732, vol. 6(9).
Ebersbach, Affilin—Novel Binding Molecules Based on Human γ-B-Crystallin, an All β-Sheet Protein, Journal Molecular Biology, 2007, pp. 172-185, vol. 372.
Fraley, New generation liposomes: the engineering of an efficient vehicle for intracellular delivery of nucleic acids, TIBS, 1981, pp. 77-80.
Goeddel, Systems for Heterologous Gene Expression, Methods in Enzymology, 1990, pp. 3-7, vol. 185.
Grabulovski, A Novel, Non-immunogenic Fyn SH3-derived Binding Protein with Tumor Vascular Targeting Properties, The Journal of Biological Chemistry, Feb. 2007, pp. 3196-3204, vol. 282 No. 5.

(Continued)

*Primary Examiner* — Benjamin P Blumel
(74) *Attorney, Agent, or Firm* — David L. Pflugh; Elizabeth A. McGraw

(57) ABSTRACT

This disclosure relates to reagents, methods for treating, diagnosing, and tracking diseases associated with salmon alphavirus.

16 Claims, 20 Drawing Sheets

(56) References Cited

OTHER PUBLICATIONS

Figure 1:
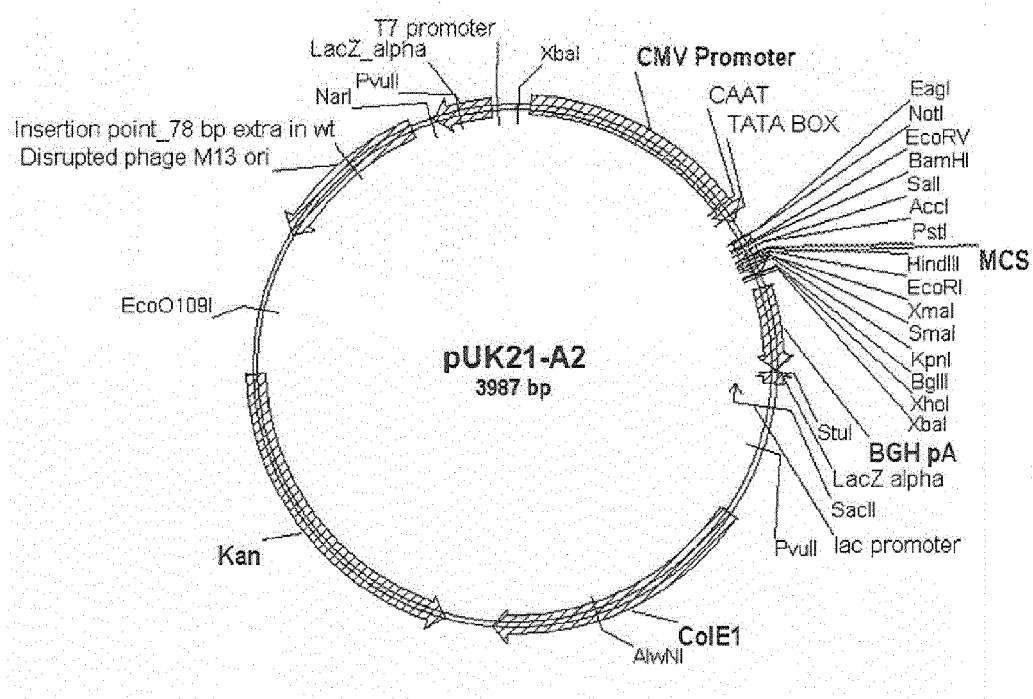

Hanke, Enhancement of MHC class I-restricted peptide-specific T cell induction by a DNA prime/WA boost vaccination regime, Vaccine, 1998, pp. 439-445, vol. 16 No. 5.
Hodneland, New subtype of salmonid alphavirus (SAV), Togaviridae, from Atlantic salmon Salmo salar and rainbow trout Oncorhynchus mykiss in Norway, Diseases of Aquatic Organisms, 2005, pp. 113-120, vol. 66.
Hoogenboom, Human Antibodies from Synthetic Repertoires of Germline Vh Gene Segments Rearranged in Vitro, Journal Molebular Biology, 1992, pp. 381-388, vol. 227.
Huang, Human Immunodeficiency Virus Type 1-Specific Immunity after Genetic Immunization Is Enhanced by Modification of Gag and Pol Expression, Journal of Virology, May 2001, pp. 4947-4951, vol. 75, No. 10.
Wasaki, Enhanced CTL Responses Mediated by Plasmid DNA Immunogens Encoding Costimulatory Molecules and Cytokines, The Journal of Immunology, 1997, pp. 4951-4601, vol. 158.
Jones, Replacing the complementarity-determining regions in a human antibody with those from a mouse, Nature, 1986, pp. 522-525, vol. 3211.
Jorgensen, CpG DNA Induces Protective Antiviral Immune Responsesin Atlantic Salmon (Salmo salar L.), Journal of Virology, Nov. 2003, pp. 11471-11479, vol. 77, No. 21.
Kim, Modulation of amplitude and direction of in vivo immune responses by co-administration of cytokine gene expression cassettes with DNA immunogens, Eur. Journal Immunology, 1998, pp. 1089-1103, vol. 28.
Kohler, Continuous cultures of fuced cells secreting antibody of predefiined specificity, Nature, 1975, pp. 496-497 vol. 256.
Koide, Antibody Mimics Based on the Scaffold of the Fibronectin Type III Domain, Monobodies, 2007, pp. 95-109.
Krehenbrink, Artificial Binding Proteins (Affitins) as Probes for Conformational Changes in Secretin PuID, Journal Molecular Biology, 2008, pp. 1058-1068, vol. 383.
Leitner, Enhancement of Tumor-specific Immune Response with Plasmid DNA Replicon Vectors, Cancer Research, Jan. 2000, pp. 51-55, vol. 60.
Liu, Gene-Based Vaccines, Molecular Therapy, Jun. 2000, pp. 497-500, vol. 1, No. 6.
Lonberg, Antigen-specific human antibodies from mice comprising four distinct genetic modification, Nature, 1994, pp. 856-859, vol. 368.
Marks, By-Passing Immunication: Building High Affinity Human Antibodies by Chain Shuffling, Biotechnology, 1992, pp. 779-783, vol. 10.
Marks, By-passing Immunization Human Antibodies from V-gene Libraries Displayed on Phage, Journal of Molecular Biology, 1991, pp. 581-597, vol. 222.
Morrison, Success in specification, Nature, 1994, pp. 812-813, vol. 369.
Neuberger, Generating high-avidity human Mabs in mice, Nature Biotechnology, 1996, pp. 826, vol. 14.
Nygren, Alternative binding proteins: Affibody bingind proteins developed from a small three-helix bundle scaffold, FEBS Journal, 2008, pp. 2668-2676, vol. 275.
Presta, Antibody engineering, Current Opinion in Structural Biology, 1992, pp. 593-596, vol. 2.
Riechmann, Reshaping human antibodies for therapy, Nature, 1988, pp. 323-327, vol. 332.
Sambrook, Molecular cloning, A Laboratory Manual, Second Edition 1989.
Scheerlinck, Genetic adjuvants for DNA vaccines, Vaccine, 2001, pp. 2647-2656, vol. 19.
Scott, Regulation of Plasmid Replication, Microbiological Reviews, 1984, pp. 1-23, vol. 48, No. 1.
Silverman, Multivalent avimer proteins evolved by exon shuffling of a family of human receptor domains, Nature Biotechnology, 2005, pp. 1556-1561, vol. 23, No. 12.
Skerra, Alternative binding proteins: Anticalins—harnessing the structural plasticity of the lipocalin ligand pocket to engineer novel binding activities, FEBS Journal 275 (2008) 2677-2683.
Strandskog, Characterization of three distinct CpG oligonucleotide classeswhich differ in ability to induce IFN a/b activity and cell proliferation in Atlantic salmon (Salmo salar L.) leukocytes, Developmental and Comparative Immunology, 2007, pp. 39-51, vol. 31.
Strauss, The Alpha, viruses: Gene Expression, Replication, and Evolution, Microbiological Reviews, Sep. 1994, pp. 491-562, vol. 58 No. 3.
Stumpp, A new generation of protein therapeutics, Drug Discovery Today, Aug. 2008, pp. 695-701, vol. 13, No. 15-16.
Sullivan, Development of a preventive vaccine for Ebola virus infection in primates, Nature, Nov. 2000, pp. 605-609, vol. 408.
Thomson, Targeting a Polyepitope Protein Incorporating Multiple Class II-Restricted Viral Epitopes to the SecretoryEndocytic Path, Journal of Virology, Mar. 1998, pp. 2246-2252, vol. 72, No. 3.
Tomizawa, Replication of Colicin E1 Plasmid DNA in Cell Extracts*. Origin and Direction of Replication, Prob, Nat. Acad. Science, Jun. 1974, pp. 2260-2264, vol. 71, No. 6.
Velders, Defined Flanking Spacers and Enhanced Proteolysis Is Essential for Eradication of Established Tumors by an Epitope String DNA Vaccine, Journal of Immunology, 2001, pp. 5366-5371, vol. 166.
Verhoeyen, Reshaping Human Antibodies: Grafting an Antilysozyme Activity, Science, 1987, pp. 1534-1536, vol. 239.
Villoing, Rainbow Trout Sleeping Disease Virus Is an Atypical Alphavirus, Journal of Virology, Jan. 2000, pp. 173-183, vol. 74, No. 1.
Nixon, Engineered protein inhibitors of proteases, Current Opinion in Drug Discovery & Development, 2006, pp. 261-268, vol. 9, No. 2.
Fishwild, High-avidity human IgGk monoclonal antibodies from a novel strain of minilocus transgenic mice, Nature Biotechnology, 1996, pp. 845-851, vol. 14.
Harlow, Antibodies, Antibodies, A Laboratory Manual, 1988.
Harlow, Antibodies, Using Antibodies, A Laboratory Manual, 1998.
Innis, A Guide to Methods and Applications, PCR Protocols, 1989.
Remington, The Science and Practice of Pharmacy, 21st Edition, 2009.

*Parental plasmid pUK21-A2*

FIGURE 2

*Construction of pUK-SPDV-poly2#57*

←— SPDV Structural Polyprotein gene —→

Viral ssRNA (≈ 11.9 kb) (positive-strand)

↓

←——— Reverse Primer

First strand cDNA fragment containing the polyprotein

↓

Forward primer ↓ ———→
←——— ↑ Reverse primer

PCR amplification

Double stranded cDNA encoding the polyprotein gene (≈ 4 kb)

↓

Restriction digest

*NotI* ——————— *NotI* ————— *EcoRI*
——————— *EcoRI*    +    pUK21-A2

Polyprotein gene (with 150 bp deletion)

↓ pUK-SPDV-poly2#57

FIGURE 3

*Construction of pUK-SPDV-poly2#1*

← SPDV Structural Polyprotein gene →

Viral ssRNA (≈ 11.9 kb) (positive-strand)

First strand cDNA fragment containing the polyprotein

Reverse Primer

PCR amplification

Forward primer

Reverse primer

Double stranded cDNA encoding the 150 bp missing region (≈ 750 bp)

Restriction digest

EcoRV / EcoRI + pUK-SPDV-poly2#57 (EcoRV, EcoRI)

↓

Polyprotein gene (complete)

pUK-SPDV-poly2#1

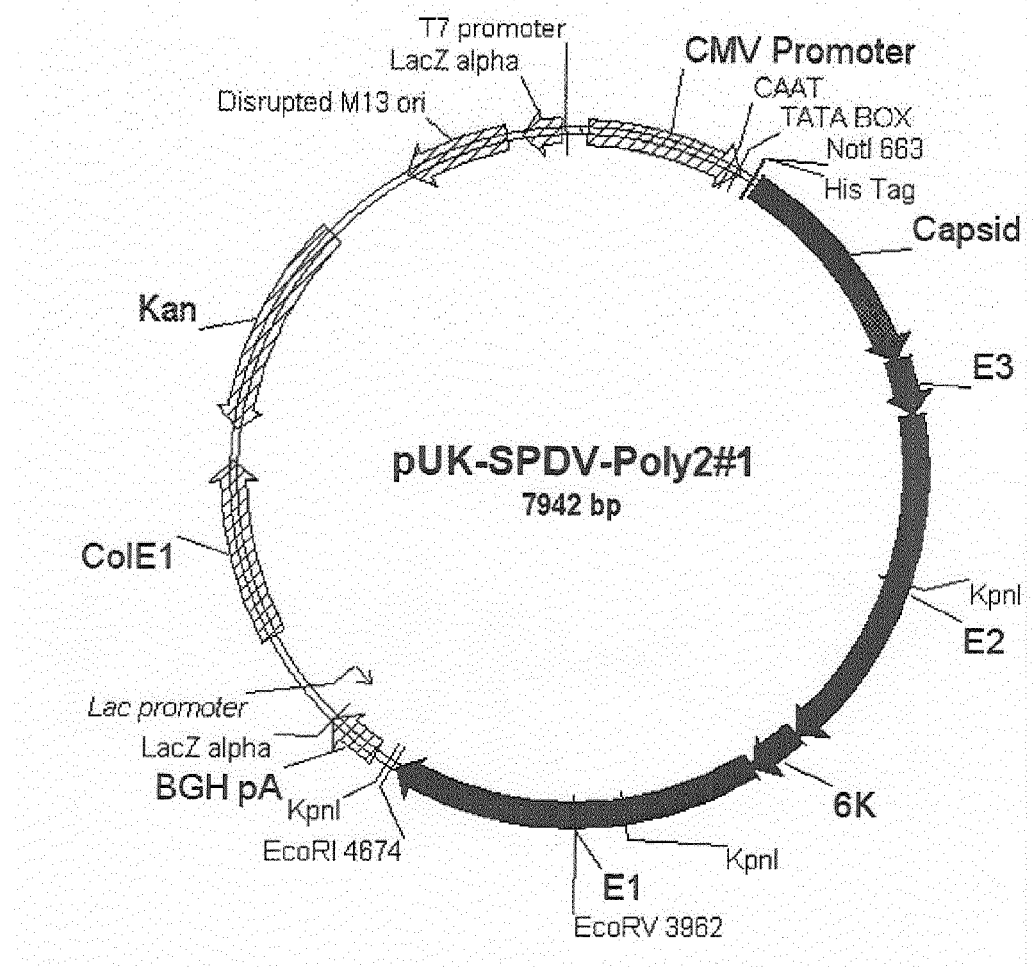

FIGURE 5
*Nucleic acid encoding SAV2 structural polyprotein*

```
 641                                                     ATGCATCATC ACCATCACCA TATGTTTCCC ATGCAATTCA CCAACTCAGC
 721  CTATCCCCAG ATGGAGCCCA TGTTCGCACC GGCTTCTCGA GGACAAGTAC AGCCGTATCG GCCGCCCACA AACCGCCGCC
 801  AAGAGCCGCA AGTCGGCAAC GCTGCTATTC CTGCCCTCCC GAACCAGATG AGCGCCTCCC AGCTCCAGGT GGCTGGACTT
 881  GCCGCCCAGG CAAGGGTGGA CCGTCGTGGA CCGAGACGTG TTCAGAAGAA CAAGCAGAAG AAGAAGAACT CTTCCAACGG
 961  AGAAAAACCC AAGGAGAAGA AGAAGAAGCA AAAACAACAG GAGAAGAAAG GGAGCGGCGG TGAAAAAGTC AAGAAGCCAC
1041  GGAACCGGCC CGGGAAGGAG GTAAGGATCT CCGTAAAGCC TGCCCGACAG AGCACCTTCC CCGTCTACCA TGACGGTGCC
1121  ATATCCGGCT ATGCGGTGCT GATTGGCTCC CGCCTGTTTA AGCCAGCGCA CGTGAAGGGT AAGATCGACC ACCCCGAACT
1201  GGCGGACATC AAGTTCCAGG TCGCCGAGGA CATGGACCTC GAAGCAGCCG CATACCCCAA GAGCATGCGA GACCAAGCGG
1281  CTGAACCAGC AACCATGACG GATCGAGTGT ACAACTGGGA ATACGGCACT ATCAGAGTGG AGGACAACGT CCTGATCGAT
1361  GCGAGCGGCA GAGCCAAGCC GGGTGACAGC GGCAGGGCCA TCACCGACAA CTCAGGAAAG GTTGTCGCTA TCGTCCTCGG
1441  AGGAGGACCC GATGGTAGGC GCACACGTCT CTCCGTGATA GGTTTCGACA AGAAGCTGAA GGCCAGAGAG ATCGCCTACA
1521  GCGAGGCCAT CCCTTGGACA CGGGCACCAG CTCTCCTGCT GCTGCCCATG GTCATCGCCT GTACCTACAA CTCCAACACC
1601  TTTGACTGCT CCAAACCGTC CTGCCAGGAC TGTTGCATTA CTGCTGAACC AAAGAAGGCC ATGACTATGC TGAAGGACAA
1681  CCTGAATGAC CCGAATTACT GGGACCTGCT TATTCCCGTC ACCACCTGCA GTTCCCCCCG AAAAAAGACG CCTCTGTCTA
1761  CGTCGCCTGC CGCCCCTTAC GACACACAAA TTCTCGCCCC CCACGCAGCT GCCTCCCCGT ATACGGCCTA CTCCCCCCAT
1841  TGTGACGGAA CTGCCTGCAT CTCGCCGATA GCTATCGACG AGGTGGTAAG TAGCGGTAGT GACCACGTCC TTCGCATCCG
1921  GGTCGGTTCT CAATCGGGAG TGACCGCTAA AGGCGGTGCG GCGGGTGAAA CCTCTCTGCG ATACCTGGGA AGGGACGGTA
2001  AGGTTCACGC CGCGGACAAC ACGCGGCTCG TGGTGCGCAC CACTGCAAAG TGTGACGTGC TGCAGGCCAC TGGCCACTAC
2081  ATTCTGGCCA ACTGCCCAGT GGGGCAGAGT CTCACTGTTG CGGCCACACT GGACCCCACC CGGCATCAAT GTACCACGCT
2161  TTTCGAACAT CAAGTAACGG AGAAGTTCAC AAGAGAACGC AGCAAGGCCC ACCACCTGTC CGATCTGACC AAGAAATGCA
2241  CCAGGTTTTC CACCACCCCG AAGAAATCCG CGCTCTATCT CGTGGATGTG TATGACGCTC TGCCGATTTC TGTAGAGATC
2321  AGCACCGTGG TGACATGCAA CGAAAGTCAG TGCACAGTGA GGGTGCCACC CGGTACCACA GTGAAATTCG ATAAGAAGTG
2401  CAAGAGCGCT GCCCAAGCGA CCGTCACCTT CACCAGCGCC TCCCAGACGT TTACGTGCGA GGAGCCGGTC CTAACGGCCG
2481  CCAGTATCAC CCAGGGCAAG CCGCACCTTA GATCGTCAAT GCTGCCCAGC GGAGGCAAAG AGGTGAAAGC CAGGATTCCA
2561  TTCCCGTTCC CGCCAGAGAC TGCGACCTGC AGAGTGACTG TCGCCCCACT GCCATCGATC ACCTATGAGG AAAGCGATGT
2641  CCTGCTGGCC GGCACTGCGA AATACCCCGT GCTGCTAACT ACACGGAATC TTGGTTTCCA TAGCAACGCC ACATCCGAAT
2721  GGATCCAGGG TAAGTACCTG CGCCGCATCC CGGTCACGCC CCAAGGGATC GAACTAATGT GGGGAAACAA CGCACCGCTG
2801  CACTTCTGGT CATCTGTCAG GTACGCATCT GGGGACGCCG ACGCGTACCC CTGGGAACTT CTGGTGCACC ACATCAAGCA
2881  CCATCCGGAG TATGCCTGGC CGTTTGTAGG ACTTGCATCT GGCCTACTGG CCGTTGCAGC ATGCGTGTTT GCGTGCGCAT
2961  GCAACAGGGT GCGGTACTCT CTGCTTGCCA ACACGTTCAA CCCGAACCCA CCACCACTGA CCGCACTGAC TGCAGCACTG
3041  TGCTGCATAC CTGGGGCTCG CGCGGATCAA CCCTACCTGG ACATCATTGC CTACTTGTGG ACCAACAGCA AAGTGGCCTT
3121  CGGGCTGCAA TGCGCGGCGC CCGTGGCTTG TATGCTCATC GTCACATACG CCCTTAGACA CTGCAGATTG TGCTGCAAGT
3201  CTTTTTTAGG GGTAAGAGGG TGGTCGGCTC TGTTGCTCAT CCTTGCGTAT GTACAGAGCT GCAAGAGCTA CGAACACACC
3281  GTGGTGGTCC CAATGGATCC AAGAGCCCCG TCGTACGAGG CGGTGATAAA CCGGAATGGC TATGACCCCC TGAAGCTGAC
3361  CATCGCAGTG AATTTCACCG TCATCTCACC AACTACGGCT CTGGAATACT GGACCTGTGC AGGAGTCCCT GTCGTCGAGC
3441  CGCCCCATGT GGGCTGCTGC ACGTCAGTGT CCTGCCCCAC CGACCTCTCC ACGCTGCACG CGTTCACCGG CAAAGCCGTC
3521  TCCGACGTGC ACTGCGATGT GCACACAAAC GTGTACCCCT TGTTGTGGGG TGCGGCTCAC TGCTTTTGTT CCACTGAAAA
3601  CACCCAGCTC ACCCCTGTGC CCGCCACCCT TTCTCACTTC TCCCCTCACG ACCCAGAACC CGCCCACGCG TTCAGCGTTC
3681  ACAGCAGCTC AGTCACTGCA GAGATCCTGG TGACGCTTGG TGAAGTGGTG ACGGCAGTCC ACGTTTACGT GGACGGGGTA
3761  ACATCAGCCA GGGGTACCGA CCTCAAGATC GTGGCTGGCC CAATAACAAC TGACTACTCC CCGTTTGATC GCAAAGTAGT
3841  CCGTATCAGC GAAGAGGTCT ATAACTACGA CTGGCCTCCT TACGGGGCTG GTCGACCAGG CACATTCGGA GACATTCAAG
3921  CTAGGTCAAC CAACTATGTC AAACCCAATG ATCTGTACGG GGRTRTCGGG ATTGAAGTAC TGCAGCCGAC TAATGACCAC
4001  GTGCACGTGG CTTACACGTA TACGACCTCC GGCTTACTGC GTTGCTTGCA GGACGCTCCG AAACCACTCA GTGTCACAGC
4081  ACCGCACGGT TGTAAGATCA GTGCTAACCC GCTCCTGGCC CTCGATTGTG GGGTTGGTGC CGTCCCCATG TCCATCAACA
4161  TTCCGGACGC GAAGTTCACC CGCAAATTAA AGGATCCGAA ACCATCGGCC CTGAAATGCG TGGTGGACAG TTGCGAGTAC
4241  GGGGTGGACT ACGGGGGCGC CGCCACGATC ACCTACGAGG GCCACGAGGC TGGGAAGTGC GGGATCCATT CCCTGACACC
4321  AGGAGTCCCT CTGAGAACAT CAGTGGTTGA AGTAGTTGCC GGGGCTAATA CCGTCAAAAC GACCTTCTCC TCACCCACGC
4401  CCGAGGTCAC ACTCGAGGTA GAGATCTGTT CGGCAATAGT GAAGTGCCCC AGTGAGTGCA CTCCACCGAA GGAACACGTA
4481  GTCCCAGCCA GGCCTCGCCA TGGCAGCGAC ACTGGAGGCT ACATCTCCGG GCCCGCAATG CGCTGGGCGG GAGGGATTGT
4561  AGGGACCCTA GTGGTCCTGT TCCTCATCCT TGCCGTCACC TACTGCGTGG TGAAGAAGTG CCGCTCTAAA AGAATCCGGA
4641  TAGTCAAGAG CTAA
```

SEQ ID NO.: 1

FIGURE 6 atgtttcccatgcaattcaccaactcagcctatcgccagatggagcccatgttcgcaccggcttctcgagg
acaagtacagccgtatcggccgcgcacaaagcgccgccaagagccgcaagtcggcaacgctgctattgctg
ccctcgcgaaccagatgagcgcgctccagctgcaggtggctggacttgccggccaggcaagggtggaccgt
cgtggaccgagacgtgttcagaagaacaagcagaagaagaagaactcttccaacggagaaaaacccaagga
gaagaagaagaagcaaaaccacaggagaagaaagggagcggcggtgaaaaagtcaagaagccacggaacc
ggccgggaaggaggtaaggatctccgtaaagcgtgcccgacagagcaccttcccgtgtaccatgacggt
gccatatccggctatgcggtgctgattggctcccgcgtgtttaagccagcgcacgtgaagggtaagatcga
ccaccccgaactggcggacatcaagttccaggtcgccgaggacatggacctcgaagcagccgcatacccca
agagcatgcgagaccaagcggctgaaccagcaaccatgacggatggagtgtacaactgggaatacggcact
atcagagtggaggacaacgtcgtgatcgatgcgagcggcagaggcaagccgggtgacagcggcagggccat
caccgacaactcaggaaagttgtcggtatcgtcctccggaggaggacccgatggtaggcgcacacgtctct
ccgtgataggtttcgacaagaagctgaaggccagagagatcgcctacagcgaggccatcccttggacacgc
gcaccagctctcctgctgctgcccatggtcatcgcctgtacctacaactccaacaccttttgactgctccaa
acgtcctgccaggactgttgcattactgctgaaccaaagaaggccatgactatgctgaaggacaacctga
atgacccgaattactgggacctgcttattgccgtcaccacctgcagttccgccgaaaaaagagggctgtg
tctacgtcgcctgccgccgcttacgacacacaaattctcgccgcccacgcagctgcctccccgtatagggc
gtactgcccgattgtgacggaactgcctgcatctcgccgatagctatcgacgaggtggtaagtagcggta
gtgaccacgtccttcgcatccgggtcggttctcaatcgggagtgaccgctaaaggcggtgcggcggtgaa
acctctctgcgatacctggaaggggacggtaaggttcacgccgcggacaacacgcggctcgtggtgcgcac
cactgcaaagtgtgacgtgctgcaggccactggccactacattctggccaactgcccagtggggcagagtc
tcactgttgcggccacactggacggcacccggcatcaatgtaccacggttttcgaacatcaagtaacggag
aagttcacaagagaacgcagcaagggccaccacctgtccgatctgaccaagaaatgcaccaggttttccac
caccccgaagaaatccgcgctctatctcgtggatgtgtatgacgctctgccgatttctgtagagatcagca
ccgtggtgacatgcaacgaaagtcagtgcacagtgagggtgccacccggtaccacagtgaaattcgataag
aagtgcaagagcgctgcccaagcgaccgtcaccttcaccagcggctcccagacgtttacgtgcgaggagcc
ggtcctaacggccgccagtatcacccagggcaagccgcaccttagatcgtcaatgctgcccagcggaggca
aagaggtgaaagcgaggattccattcccgttcccgccagagactgcgacctgcagagtgagtgtcgcccca
ctgccatcgatcacctatgaggaaagcgatgtcctgctggccggcactgcgaaataccccgtgctgctaac
tacacggaatcttggtttccatagcaacgccacatccgaatggatccagggtaagtacctgcgccgcatcc
cggtcacgccccaaggggatcgaactaatgtggggaaacaacgcacgctgcacttctggtcatctgtcagg
tacgcatctggggacgccgacgcgtacccctgggaacttctggtgcaccacatcaagcaccatccggagta
tgcgtgggcgtttgtaggagttgcatgtggcctactggccgttgcagcatgcgtgtttgcgtgcgcatgca
acagggtgcggtactctctgcttgccaacacgttcaacccgaacccaccaccactgaccgcactgactgca
gcactgtgctgcatacctggggctcgcgcggatcaaccctacctggacatcattgcctacttgtggaccaa
cagcaaagtggccttcgggctgcaatgcgcggcgccgtggcttgtatgctcatcgtcacatacgcccta
gacactgcagattgtgctgcaagtcttttttaggggtaagagggtggtcggctctgttggtcatccttgcg
tatgtacagagctgcaagagctacaacacaccgtggtggtcccaatggatccaagagccccgtcgtacga
ggcggtgataaaccggaactgggtatgacccccctgaagctgaccatcgcagtgaatttcaccgtcatctcac
caactacggctctggaatactggacctgtgcaggagtccctgtcgtcgagccgccccatgtgggctgctgc
acgtcagtgtcctgccccaccgacctctccacgctgcacgcgttcaccggcaaagccgtctccgacgtgca
ctgcgatgtgcacacaaacgtgtacccctgttgtgggtgcggctcactgcttttgttccactgaaaaca
cgcaggtcagcgctgtggccgccaccgtttctgagttctgcgctcaggacgcagaacgcgccgaggcgttc
agcgttcacagcagctcagtcactgcagagatcctggtgacgcttggtgaagtggtgacggcagtccacgt
ttacgtggacgggtaacatcagccaggggtaccgacctcaagatcgtggctggcccaataacaactgact
actccccgtttgatcgcaaagtagtccgtatcagcgaagaggtctataactacgactggcctccttacggg
gctggtcgaccaggcacattcggagacattcaagctaggtcaaccaactatgtcaaacccaatgatctgta
cgggatatcggattgaagtactgcagccgactaatgaccacgtgcacgtggcttacacgtatacgacct
ccgggttactgcgttggttgcaggacgctccgaaaccactcagtgtcacagcaccgcacggttgtaagatc
agtggctaacccgctcctggccctcgattgtggggttggtgccgtcccatgtccatcaacattccggacgc
gaagttcacccgcaaattaaaggatccgaaaccatcggccctgaaatgcgtggtggacagttgcgagtacg
gggtggactacggggcgccgccacgatcacctacgagggccacgaggctgggaagtgcgggatccattcc
ctgacaccaggagtccctctgagaacatcagtggttgaagtagttgccgcgctaataccgtcaaaacgac
cttctcctcaccacgcccgaggtcacactcgaggtagagatctgttcggcaatagtgaagtgcgccagtg
agtgcactccaccgaaggaacacgtagtcgcagccaggcctcgccatggcagcgacactggaggctacatc
tccgggccgcaatgcgctgggccggagggattgtagggacctagtggtcctgttcctcatccttgccgt
cacctactgcgtggtgaagaagtgccgctctaaaagaatccggatagtcaagagctaa (SEQ ID NO.: 2)

FIGURE 7

```
   1  CTAGATCCGA TGTACGGGCC AGATATACGC GTTGACATTG ATTATTGACT AGTTATTAAT
  60  AGTAATCAAT TACGGGGTCA TTAGTTCATA GCCCATATAT GGAGTTCCGC GTTACATAAC
 121  TTACGGTAAA TGGCCCGCCT GGCTGACCGC CCAACGACCC CCGCCCATTG ACGTCAATAA
 181  TGACGTATGT TCCCATAGTA ACGCCAATAG GGACTTTCCA TTGACGTCAA TGGGTGGAGT
 241  ATTTACGGTA AACTGCCCAC TTGGCAGTAC ATCAAGTGTA TCATATGCCA AGTACGCCCC
 301  CTATTGACGT CAATGACGGT AAATGGCCCG CCTGGCATTA TGCCCAGTAC ATGACCTTAT
 361  GGGACTTTCC TACTTGGCAG TACATCTACG TATTAGTCAT CGCTATTACC ATGGTGATGC
 421  GGTTTTGGCA GTACATCAAT GGGCGTGGAT AGCGGTTTGA CTCACGGGGA TTTCCAAGTC
 481  TCCACCCCAT TGACGTCAAT GGGAGTTTGT TTTGGCACCA AAATCAACGG GACTTTCCAA
 541  AATGTCGTAA CAACTCCGCC CCATTGACGC AAATGGGCGG TAGGCGTGTA CGGTGGGAGG
 601  TCTATATAAG CAGAGCTCTC TGGCTAACTA GAGAACCCAC TGCTTACTGG CTTATCGAAA
       NotI       His-tag                       Insert start site
 661  TTGCGGCCGC ATGCATCATC ACCATCACCA TATGTTTCCC ATGCAATTCA CCAACTCAGC
 721  CTATCGCCAG ATGGAGCCCA TGTTCGCACC GGCTTCTCGA GGACAAGTAC AGCCGTATCG
 781  GCCGCGCACA AAGCGCCGCC AAGAGCCGCA AGTCGGCAAC GCTGCTATTG CTGCCCTCGC
 841  GAACCAGATG AGCGCGCTCC AGCTGCAGGT GGCTGGACTT GCCGGCCAGG CAAGGGTGGA
 901  CCGTCGTGGA CCGAGACGTG TTCAGAAGAA CAAGCAGAAG AAGAAGAACT CTTCCAACGG
 961  AGAAAAACCC AAGGAGAAGA AGAAGAGCA AAAACAACAG GAGAAGAAAG GGAGCGGCGG
1021  TGAAAAAGTC AAAGAGCCAC GGAACCGGCC CGGGAAGGAG GTAAGGATCT CCGTAAAGCG
1081  TGCCCGACAG AGCACCTTCC CCGTGTACCA TGACGGTGCC ATATCCGGCT ATGCGGTGCT
1141  GATTGGCTCC CGCGTGTTTA AGCCAGCGCA CGTGAAGCGT AAGATCGACC ACCCCGAACT
1201  GGCGGACATC AAGTTCCAGG TCGCCGAGGA CATGGACCTC GAAGCAGCCG CATACCCCAA
1261  GAGCATGCGA GACCAAGCGG CTGAACCAGC AACCATGACG GATGGAGTGT ACAACTGGGA
1321  ATACGGCACT ATCAGAGTGG AGGACAACGT CGTGATCGAT GCGAGCGGCA GAGGCAAGCC
1381  GGGTGACAGC GGCAGGGCCA TCACCGACAA CTCAGGAAAG GTTGTCGGTA TCGTCCTCGG
1441  AGGAGGACCC GATGGTAGGC GCACACGTCT CTCCGTGATA GGTTTCGACA GAAGCTGAA
1501  GGCCAGAGAG ATCGCCTACA GCGAGGCCAT CCCTTGGACA CGCGCACCAG CTCTCCTGCT
1561  GCTGCCCATG GTCATCGCCT GTACCTACAA CTCCAACACC TTTGACTGCT CCAAACCGTC
1621  CTGCCAGGAC TGTTGCATTA CTGCTGAACC AAAGAAGGCC ATGACTATGC TGAAGGACAA
1681  CCTGAATGAC CCGAATTACT GGGACCTGCT TATTGCCGTC ACCACCTGCA GTTCCGCCCG
1741  AAAAAAGAGG GCTGTGTCTA CGTCGCCTGC CGCCGCTTAC GACACACAAA TTCTCGCCGC
1801  CCACGCAGCT GCCTCCCCGT ATAGGGCGTA CTGCCCCGAT TGTGACGGAA CTGCCTGCAT
1861  CTCGCCGATA GCTATCGACG AGGTGGTAAG TAGCGGTAGT GACCACGTCC TTCGCATCCG
1921  GGTCGGTTCT CAATCGGGAG TGACCGCTAA AGGCGGTGCG GCGGGTGAAA CCTCTCTGCG
1981  ATACCTGGGA AGGGACGGTA AGGTTCACGC CGCGGACAAC ACGCGGCTCG TGGTGCGCAC
2041  CACTGCAAAG TGTGACGTGC TGCAGGCCAC TGGGCACTAC ATTCTGGCCA ACTGCCCAGT
2101  GGGGCAGAGT CTCACTGTTG CGGCCACACT GGACGGCACC CGGCATCAAT GTACCACGGT
2161  TTTCGAACAT CAAGTAACGG AGAAGTTCAC AAGAGAACGC AGCAAGGGCC ACCACCTGTC
2221  CGATCTGACC AAGAAATGCA CCAGGTTTTC CACCACCCCG AAGAAATCCG CGCTCTATCT
2281  CGTGGATGTG TATGACGCTC TGCCGATTTC TGTAGAGATC AGCACCGTGG TGACATGCAA
2341  CGAAAGTCAG TGCACAGTGA GGGTGCCACC CGGTACCACA GTGAAATTCG ATAAGAAGTG
2401  CAAGAGCGCT GCCCAAGCGA CCGTCACCTT CACCAGCGGC TCCCAGACGT TTACGTGCGA
2461  GGAGCCGGTC CTAACGGCCG CCAGTATCAC CAGGGCAAG CCGCACCTTA GATCGTCAAT
2521  GCTGCCCAGC GGAGGCAAAG AGGTGAAAGC GAGGATTCCA TTCCCGTTCC CGCCAGAGAC
2581  TGCGACCTGC AGAGTGAGTG TCGCCCCACT GCCATCGATC ACCTATGAGG AAAGCGATGT
2641  CCTGCTGGCC GGCACTGCGA ATACCCCGT GCTGCTAACT ACACGGAATC TTGGTTTCCA
2701  TAGCAACGCC ACATCCGAAT GGATCCAGGG TAAGTACCTG CGCCGCATCC CGGTCACGCC
2761  CCAAGGGATC GAACTAATGT GGGGAAACAA CGCACCGCTG CACTTCTGGT CATCTGTCAG
2821  GTACGCATCT GGGGACGCCG ACGCGTACCC CTGGGAACTT CTGGTGCACC ACATCAAGCA
2881  CCATCCGGAG TATGCGTGGG CGTTTGTAGG AGTTGCATGT GGCCTACTGG CCGTTGCAGC
```

FIGURE 7 (continued)

```
2941  ATGCGTGTTT GCGTGCGCAT GCAACAGGGT GCGGTACTCT CTGCTTGCCA ACACGTTCAA
3001  CCCGAACCCA CCACCACTGA CCGCACTGAC TGCAGCACTG TGCTGCATAC CTGGGGCTCG
3061  CGCGGATCAA CCCTACCTGG ACATCATTGC CTACTTGTGG ACCAACAGCA AAGTGGCCTT
3121  CGGGCTGCAA TGCCGGCGC CCGTGGCTTG TATGCTCATC GTCACATACG CCCTTAGACA
3181  CTGCAGATTG TGCTGCAAGT CTTTTTTAGG GGTAAGAGGG TGGTCGGCTC TGTTGGTCAT
3241  CCTTGCGTAT GTACAGAGCT GCAAGAGCTA CGAACACACC GTGGTGGTCC CAATGGATCC
3301  AAGAGCCCCG TCGTACGAGG CGGTGATAAA CCGGAATGGG TATGACCCCC TGAAGCTGAC
3361  CATCGCAGTG AATTTCACCG TCATCTCACC AACTACGGCT CTGGAATACT GGACCTGTGC
3421  AGGAGTCCCT GTCGTCGAGC CGCCCCATGT GGGCTGCTGC ACGTCAGTGT CCTGCCCCAC
3481  CGACCTCTCC ACGCTGCACG CGTTCACCGG CAAAGCCGTC TCCGACGTGC ACTGCGATGT
3541  GCACACAAAC GTGTACCCCT TGTTGTGGGG TGCGGCTCAC TGCTTTTGTT CCACTGAAAA
3601  CACGCAGGTC AGCGCTGTGG CCGCCACCGT TTCTGAGTTC TGCGCTCAGG ACGCAGAACG
3661  CGCCGAGGCG TTCAGCCGTTC ACAGCAGCTC AGTCACTGCA GACATCCTGG TGACGCTTGG
3721  TGAAGTGGTG ACGGCAGTCC ACGTTTACGT GGACGGGGTA ACATCAGCCA GGGGTACCGA
3781  CCTCAAGATC GTGGCTGGCC CAATAACAAC TGACTACTCC CCGTTTGATC GCAAAGTAGT
3841  CCGTATCAGC GAAGAGGTCT ATAACTACGA CTGGCCTCCT TACGGGGCTG GTCGACCAGG
3901  CACATTCGGA GACATTCAAG CTAGGTCAAC CAACTATGTC AAACCCAATG ATCTGTACGG
3961  GGATATCGGG ATTGAAGTAC TGCAGCCGAC TAATGACCAC GTGCACGTGG CTTACACGTA
4021  TACGACCTCC GGGTTACTGC GTTGGTTGCA GGACGCTCCG AAACCACTCA GTGTCACAGC
4081  ACCGCACGGT TGTAAGATCA GTGCTAACCC GCTCCTGGCC CTCGATTGTG GGGTTGGTGC
4141  CGTCCCCATG TCCATCAACA TTCCGGACGC GAAGTTCACC CGCAAATTAA AGGATCCGAA
4201  ACCATCGGCC CTGAAATGCG TGGTGGACAG TTGCGAGTAC GGGGTGGACT ACGGGGGCGC
4261  CGCCACGATC ACCTACGAGG GCCACGAGGC TGGGAAGTGC GGGATCCATT CCCTGACACC
4321  AGGAGTCCCT CTGAGAACAT CAGTGGTTGA AGTAGTTGCC GGCGCTAATA CCGTCAAAAC
4381  GACCTTCTCC TCACCCACGC CCGAGGTCAC ACTCGAGGTA GAGATCTGTT CGGCAATAGT
4441  GAAGTGCGCC AGTGAGTGCA CTCCACCGAA GGAACACGTA GTCGCAGCCA GGCCTCGCCA
4501  TGGCAGCGAC ACTGGAGGCT ACATCTCCGG GCCCGCAATG CGCTGGGCCG GAGGGATTGT
4561  AGGGACCCTA GTGGTCCTGT TCCTCATCCT TGCCGTCACC TACTGCGTGG TGAAGAAGTG
                                                            Stop Codon
4621  CCGCTCTAAA AGAATCCGGA TAGTCAAGAG CTAAATTCCG GTATACAAAT TGCGAATTCG
4681  AGCTCCCGGG TACCATGCA TGCATCGATA GATCTCGAGT CTAGACTAGA GCTCGCTGAT
4741  CAGCCTCGAC TGTGCCTTCT AGTTGCCAGC CATCTGTTGT TTGCCCCTCC CCCGTGCCTT
4801  CCTTGACCCT GGAAGGTGCC ACTCCCACTG TCCTTTCCTA ATAAAATGAG GAAATTGCAT
4861  CGCATTGTCT GAGTAGGTGT CATTCTATTC TGGGGGGTGG GGTGGGGCAG GACAGCAAGG
4921  GGGAGGATTG GGAAGACAAT AGCAGGCATG CTGGGGAAGG CCTCGGACTA GTGGCGTAAT
4981  CATGGTCATA GCTGTTTCCT GTGTGAAATT GTTATCCGCT CACAATTCCA CACAACATAC
5041  GAGCCGCGGA AGCATAAAGT GTAAAGCCTG GGGTGCCTAA TGAGTGAGCT AACTCACATT
5101  AATTGCGTTG CGCTCACTGC CCGCTTTCCA GTCGGGAAAC CTGTCGTGCC AGCTGCATTA
5161  ATGAATCGGC CAACGCGCGG GGAGAGGCGG TTTGCGTATT GGGCGCTCTT CCGCTTCCTC
5221  GCTCACTGAC TCGCTGCGCT CGGTCGTTCG GCTGCGGCGA GCGGTATCAG CTCACTCAAA
5281  GGCGGTAATA CGGTTATCCA CAGAATCAGG GGATAACGCA GGAAAGAACA TGTGAGCAAA
5341  AGGCCAGCAA AAGGCCAGGA ACCGTAAAAA GGCCGCGTTG CTGGCGTTTT TCCATAGGCT
5401  CCGCCCCCCT GACGAGCATC ACAAAAATCG ACGCTCAAGT CAGAGGTGGC GAAACCCGAC
5461  AGGACTATAA AGATACCAGG CGTTTCCCCC TGGAAGCTCC CTCGTGCGCT CTCCTGTTCC
5521  GACCCTGCCG CTTACCGGAT ACCTGTCCGC CTTTCTCCCT TCGGGAAGCG TGGCGCTTTC
5581  TCATAGCTCA CGCTGTAGGT ATCTCAGTTC GGTGTAGGTC GTTCGCTCCA AGCTGGGCTG
5641  TGTGCACGAA CCCCCCGTTC AGCCCGACCG CTGCGCCTTA TCCGGTAACT ATCGTCTTGA
5701  GTCCAACCCG GTAAGACACG ACTTATCGCC ACTGGCAGCA GCCACTGGTA ACAGGATTAG
5761  CAGAGCGAGG TATGTAGGCG GTGCTACAGA GTTCTTGAAG TGGTGGCCTA ACTACGGCTA
5821  CACTAGAAGA ACAGTATTTG GTATCTGCGC TCTGCTGAAG CCAGTTACCT TCGGAAAAAG
5881  AGTTGGTAGC TCTTGATCCG GCAAACAAAC CACCGCTGGT AGCGGTGGTT TTTTGTTTG
```

FIGURE 7 (continued)

```
5941  CAAGCAGCAG ATTACGCGCA GAAAAAAAGG ATCTCAAGAA GATCCTTTGA TCTTTTCTAC
6001  GGGGTCTGAC GCTCAGTGGA ACGAAAACTC ACGTTAAGGG ATTTTGGTCA TGAGCTTGCG
6061  CCGTCCCGTC AAGTCAGCGT AATGCTCTGC CAGTGTTACA ACCAATTAAC CAATTCTGAT
6121  TAGAAAAACT CATCGAGCAT CAAATGAAAC TGCAATTTAT TCATATCAGG ATTATCAATA
6181  CCATATTTTT GAAAAAGCCG TTTCTGTAAT GAAGGAGAAA ACTCACCGAG GCAGTTCCAT
6241  AGGATGGCAA GATCCTGGTA TCGGTCTGCG ATTCCGACTC GTCCAACATC AATACAACCT
6301  ATTAATTTCC CCTCGTCAAA AATAAGGTTA TCAAGTGAGA AATCACCATG AGTGACGACT
6361  GAATCCGGTG AGAATGGCAA AAGTTTATGC ATTTCTTTCC AGACTTGTTC AACAGGCCAG
6421  CCATTACGCT CGTCATCAAA ATCACTCGCA TCAACCAAAC CGTTATTCAT TCGTGATTGC
6481  GCCTGAGCGA GACGAAATAC GCGATCGCTG TTAAAAGGAC AATTACAAAC AGGAATCGAA
6541  TGCAACCGGC GCAGGAACAC TGCCAGCGCA TCAACAATAT TTTCACCTGA ATCAGGATAT
6601  TCTTCTAATA CCTGGAATGC TGTTTTTCCG GGGATCGCAG TGGTGAGTAA CCATGCATCA
6661  TCAGGAGTAC GGATAAAATG CTTGATGGTC GGAAGAGGCA TAAATTCCGT CAGCCAGTTT
6721  AGTCTGACCA TCTCATCTGT AACATCATTG GCAACGCTAC CTTTGCCATG TTTCAGAAAC
6781  AACTCTGGCG CATCGGGCTT CCCATACAAG CGATAGATTG TCGCACCTGA TTGCCCGACA
6841  TTATCGCGAG CCCATTTATA CCCATATAAA TCAGCATCCA TGTTGGAATT TAATCGCGGC
6901  CTCGACGTTT CCCGTTGAAT ATGGCTCATA ACACCCCTTG TATTACTGTT TATGTAAGCA
6961  GACAGTTTTA TTGTTCATGA TGATATATTT TTATCTTGTG CAATGTAACA TCAGAGATTT
7021  TGAGACACAA CGTGGCTTTC CCCCCCCCCC CCATGACATT AACCTATAAA AATAGGCGTA
7081  TCACGAGGCC CTTTCGTCTC GCGCGTTTCG GTGATGACGG TGAAAACCTC TGACACATGC
7141  AGCTCCCGGA GACGGTCACA GCTTGTCTGT AAGCGGATGC CGGGAGCAGA CAAGCCCGTC
7201  AGGGCGCGTC AGCGGGTGTT GGCGGGTGTC GGGGCTGGCT TAACTATGCG GCATCAGAGC
7261  AGATTGTACT GAGAGTGCAC CATAAAATTG TAAACGTTAA TATTTTGTTA AAATTCGCGT
7321  TAAATTTTTG TTAAATCAGC TCATTTTTTA ACCAATAGAC CGAAATCGGC AAAATCCCTT
7381  ATAAATCAAA AGAATAGCCC GAGATAGAGT TGAGTGTTGT TCCAGTTTGG AACAAGAGTC
7441  CACTATTAAA GAACGTGGAC TCCAACGTCA AAGGGCGAAA AACCGTCTAT CAGGGCGATG
7501  GCCCACCCCG ATTTAGAGCT TGACGGGGAA AGCCGGCGAA CGTGGCGAGA AAGGAAGGGA
7561  AGAAAGCGAA AGGAGCGGGC GCTAAGGCGC TGGCAAGTGT AGCGGTCACG CTGCGCGTAA
7621  CCACCACACC CGCCGCGCTT AATGCGCCGC TACAGGGCGC GTACTATGGT TGCTTTGACG
7681  TATGCGGTGT GAAATACCGC ACAGATGCGT AAGGAGAAAA TACCGCATCA GGCGCCATTC
7741  GCCATTCAGG CTGCGCAACT GTTGGGAAGG GCGATCGGTG CGGGCCTCTT CGCTATTACG
7801  CCAGCTGGCG AAAGGGGGAT GTGCTGCAAG GCGATTAAGT TGGGTAACGC CAGGGTTTTC
7861  CCAGTCACGA CGTTGTAAAA CGACGGCCAG TGAATTGTAA TACGACTCAC TATAGGGCGA
7921  ATTGGGGATC GATCCACTAG TT (SEQ ID NO.: 3)
```

FIGURE 8

Polyprotein with His tag

MHHHHHHMFPMQFTNSAYRQMEPMFAPASRGQVQFYRPRTKRRQEPQVGNAAIAALANQMSALQLQVAGLA
GQARVDRRGPRRVQKNKQKKKNSSNGEKPKEKKKKQKQQEKKGSGGEKVKKPRNRPGKEVRISVKRARQST
FPVYHDGAISGYAVLIGSRVFKPAHVKGKIDHPELADIKFQVAEDMDLEAAAYPKSMRDQAAEPATMTDGV
YNWEYGTIRVEDNVVIDASGRGKPGDSGRAITDNSGKVVGIVLGGGPDGRRTRLSVIGFDKKLKAREIAYS
EAIPWTRAPALLLLPMVIACTYNSNTFDCSKPSCQDCCITAEPKKAMTMLKDNLNDPNYWDLLIAVTTCSS
ARKKRAVSTSPAAAYDTQILAAHAAASPYRAYCPDCDGTACISPIAIDEVVSSGSDHVLRIRVGSQSGVTA
KGGAAGETSLRYLGRDGKVHAADNTRLVVRTTAKCDVLQATGHYILANCPVGQSLTVAATLDGTRHQCTTV
FEHQVTEKFTRERSKGHHHLSDLTKKCTRFSTTPKKSALYLVDVYDALPISVEISTVVTCNESQCTVRVPPG
TTVKFDKKCKSAAQATVTFTSGSQTFTCEEPVLTAASITQGKPHLRSSMLPSGGKEVKARIPFPFPPETAT
CRVSVAPLPSITYEESDVLLAGTAKYPVLLTTRNLGFHSNATSEWIQGKYLRRIPVTPQGIELMWGNNAPL
HFWSSVRYASGDADAYPWELLVHHIKHHPEYAWAFVGVACGLLAVAACVFACACNRVRYSLLANTFNPNPP
PLTALTAALCCIPGARADQPYLDIIAYLWTNSKVAFGLQCAAPVACMLIVTYALRHCRLCCKSFLGVRGWS
ALLVILAYVQSCKSYEHTVVVPMDPRAPSYEAVINRNGYDPLKLTIAVNFTVISPTTALEYWTCAGVPVVE
PPHVGCCTSVSCPTDLSTLHAFTGKAVSDVHCDVHTNVYPLLWGAAHCFCSTENTQVSAVAATVSEFCAQD
AERAEAFSVHSSSVTAEILVTLGEVVTAVHVYVDGVTSARGTDLKIVAGPITTDYSPFDRKVVRISEEVYN
YDWPPYGAGRPGTFGDIQARSTNYVKPNDLYGDIGIEVLQPTNDHVHVAYTYTTSGLLRWLQDAPKPLSVT
APHGCKISANPLLALDCGVGAVPMSINIPDAKFTRKLKDPKPSALKCVVDSCEYGVDYGGAATITYEGHEA
GKCGIHSLTPGVPLRTSVVEVVAGANTVKTTFSSPTPEVTLEVEICSAIVKCASECTPPKEHVVAARPRHG
SDTGGYISGPAMRWAGGIVGTLVVLFLILAVTYCVVKKCRSKRIRIVKS (SEQ ID NO.: 4)

FIGURE 9: Polyprotein

MFPMQFTNSAYRQMEPMFAPASRGQVQFYRPRTKRRQEPQVGNAAIAALANQMSALQLQVAGLAGQARVDR
RGPRRVQKNKQKKKNSSNGEKPKEKKKKQKQQEKKGSGGEKVKKPRNRPGKEVRISVKRARQSTFPVYHDG
AISGYAVLIGSRVFKPAHVKGKIDHPELADIKFQVAEDMDLEAAAYPKSMRDQAAEPATMTDGVYNWEYGT
IRVEDNVVIDASGRGKPGDSGRAITDNSGKVVGIVLGGGPDGRRTRLSVIGFDKKLKAREIAYSEAIPWTR
APALLLLPMVIACTYNSNTFDCSKPSCQDCCITAEPKKAMTMLKDNLNDPNYWDLLIAVTTCSSARKKRAV
STSPAAAYDTQILAAHAAASPYRAYCPDCDGTACISPIAIDEVVSSGSDHVLRIRVGSQSGVTAKGGAAGE
TSLRYLGRDGKVHAADNTRLVVRTTAKCDVLQATGHYILANCPVGQSLTVAATLDGTRHQCTTVFEHQVTE
KFTRERSKGHHHLSDLTKKCTRFSTTPKKSALYLVDVYDALPISVEISTVVTCNESQCTVRVPPGTTVKFDK
KCKSAAQATVTFTSGSQTFTCEEPVLTAASITQGKPHLRSSMLPSGGKEVKARIPFPFPPETATCRVSVAP
LPSITYEESDVLLAGTAKYPVLLTTRNLGFHSNATSEWIQGKYLRRIPVTPQGIELMWGNNAPLHFWSSVR
YASGDADAYPWELLVHHIKHHPEYAWAFVGVACGLLAVAACVFACACNRVRYSLLANTFNPNPPPLTALTA
ALCCIPGARADQPYLDIIAYLWTNSKVAFGLQCAAPVACMLIVTYALRHCRLCCKSFLGVRGWSALLVILA
YVQSCKSYEHTVVVPMDPRAPSYEAVINRNGYDPLKLTIAVNFTVISPTTALEYWTCAGVPVVEPPHVGCC
TSVSCPTDLSTLHAFTGKAVSDVHCDVHTNVYPLLWGAAHCFCSTENTQVSAVAATVSEFCAQDAERAEAF
SVHSSSVTAEILVTLGEVVTAVHVYVDGVTSARGTDLKIVAGPITTDYSPFDRKVVRISEEVYNYDWPPYG
AGRPGTFGDIQARSTNYVKPNDLYGDIGIEVLQPTNDHVHVAYTYTTSGLLRWLQDAPKPLSVTAPHGCKI
SANPLLALDCGVGAVPMSINIPDAKFTRKLKDPKPSALKCVVDSCEYGVDYGGAATITYEGHEAGKCGIHS
LTPGVPLRTSVVEVVAGANTVKTTFSSPTPEVTLEVEICSAIVKCASECTPPKEHVVAARPRHGSDTGGYI
SGPAMRWAGGIVGTLVVLFLILAVTYCVVKKCRSKRIRIVKS (SEQ ID NO.: 5)

FIGURE 10: Capsid

MFPMQFTNSAYRQMEPMFAPASRGQVQFYRPRTKRRQEPQVGNAAIAALANQMSALQLQVAGLAGQARVDR
RGPRRVQKNKQKKKNSSNGEKPKEKKKKQKQQEKKGSGGEKVKKPRNRPGKEVRISVKRARQSTFPVYHDG
AISGYAVLIGSRVFKPAHVKGKIDHPELADIKFQVAEDMDLEAAAYPKSMRDQAAEPATMTDGVYNWEYGT
IRVEDNVVIDASGRGKPGDSGRAITDNSGKVVGIVLGGGPDGRRTRLSVIGFDKKLKAREIAYSEAIPW
(SEQ ID NO.: 6 )

Figure 11: E3

TRAPALLLLPMVIACTYNSNTFDCSKPSCQDCCITASPKKAMTMLKDNLNDPNYWDLLIAVTTCSSARKKR
(SEQ ID NO.: 7)

Figure 12: E2

AVSTSPAAAYDTQILAAHAAASPYRAYCPDCDGTACISPIAIDEVVSSGSDEVLRIRVGSQSGVTAKGGAA
GETSLRYLGRDGKVHAADNTRLVVRTTAKCDVLQATGHYILANCPVGQSLTVAATLDGTRHQCTTVFEHQV
TEKFTRERSKGHHLSDLTKKCTRFSTTPKKSALYLVDVYDALPISVEISTVVTCNESQCIVRVPPGTTVKF
DKKCKSAAQATVTFTSGSQTFTCEEPVLTAASITQGKPHLRSSMLPSGGKEVKARIPFPFPPETATCRVSV
APLFSITYEESDVLLAGTAKYPVLTTRNLGFHSNATSEWIQGKYLRRIPVTPQGIELMWGNNAPLHFWSS
VRYASGDADAYPWELLVHHIKHHPEYAWAFVGVACGLLAVAACVFACACNRVRYSLLANTFNPNPPPLTAL
IAALCCIPGARA (SEQ ID NO.: 8)

Figure 13: 6K

DQPYLDIIAYLWTNSKVAFGLQCAAPVACMLIVTYALRHCRLCCKS (SEQ ID NO.: 9)

Figure 14: E1

FLGVRGWSALLVILAYVQSCKSYEHTVVVPMDPRAPSYEAVINRNGYDPLKLTIAVNFTVISPTTALEYWT
CAGVPVVEPPHVGCCTSVSCPTDLSTLHAFTGKAVSDVHCDVHTNVYPLLWGAAHCFCSTENTQVSAVAAT
VSEFCAQDAFRARAFSVHSSSVTAEILVTLGEVVTAVHVYVDGVTSARGTDLKIVAGPITTDYSPFDRKVV
RISEEVYNYDWPPYGAGRPGTFGDIQARSTNYVKPNDLYGDIGIEVLQPTNDHVHVAYTYTTSGLLRWLQD
APKPLSVTAPHGCKISANPLLALDCGVGAVPMSINIPDAKFTRKLKDPKPSALKCVVDSCEYGVDYGGAAT
ITYEGHEAGKCGIHSLTPGVPLRTSVVEVVAGANTVKTTFSSPTPEVTLEVEICSAIVKCASECTPPKEHV
VAARPRHGSDTGGYISGPAMRWAGGIVGTLVVLFLILAVTYCVVKKCRSKRIRIVKS (SEQ ID NO.:
10)

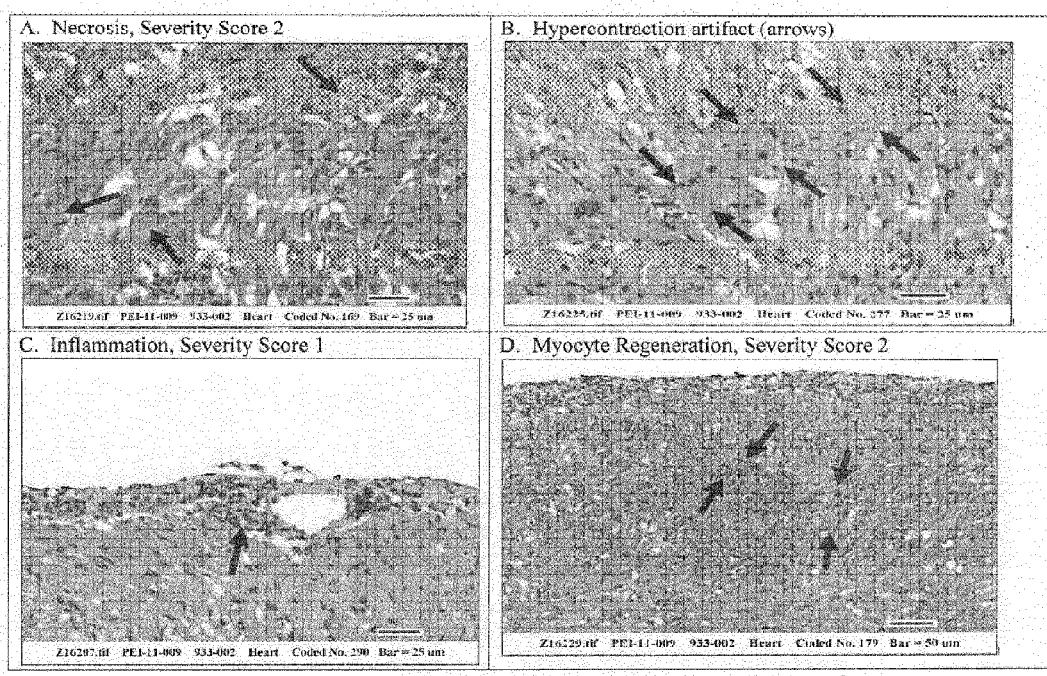

Eosinophilic Granulocyte infiltration*

Necrosis Scores

A. Score 0 (normal):
→ Absence of necrosis and signs of inflammation

B. Score 3 (highly necrotic):
→ Abundant necrotic myocytes:
dull, pale pink, individualized myocytes with rounded irregular margins and inapparent or ghost nuclei FIGURE 18
A. Histopathology Index (day 26)
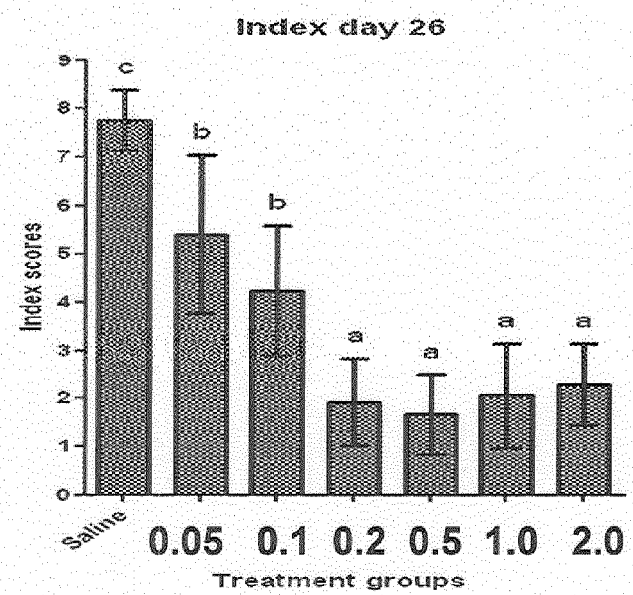
B. qPCR (day 26)
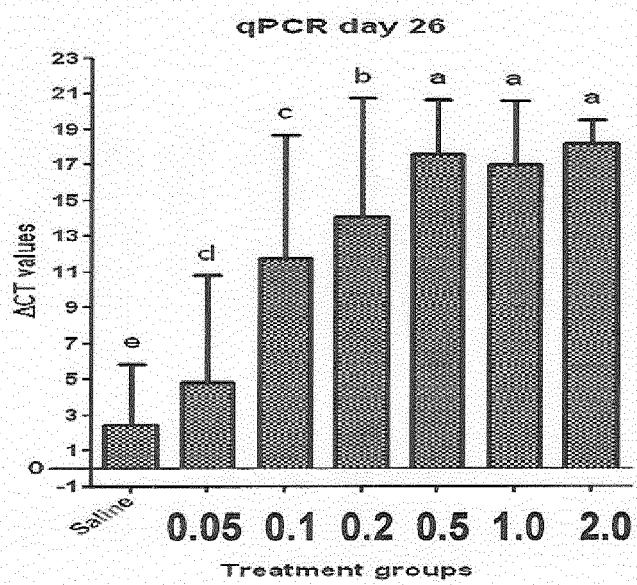

SALMONID ALPHAVIRUS AND USES THEREOF

The present application is a national phase entry under 35 U.S.C. § 371 of International Patent Application PCT/EP2013/069241, filed on Sep. 17, 2013 and published in English as International Patent Publication W02014/041189 A1 on Mar. 20, 2014, which claims benefit of priority to European Patent Application Ser. No. 12184758.6, filed Sep. 17, 2012; all of which are incorporated by reference in their entirety.

FIELD OF THE DISCLOSURE

This disclosure generally relates to nucleic acid reagents, methods for preventing, diagnosing, and tracking diseases associated with salmon alphaviruses.

BACKGROUND OF THE DISCLOSURE

Pancreas Disease (PD), is a viral disease affecting salmon (Atlantic salmon: *Salmo salar*) and rainbow trout (*Oncorhynchus mykiss*). It is also known as Salmon Pancreas Disease (SPD). Pancreas disease has caused extensive production losses within the Irish, Scottish and Norwegian salmonid aquaculture industries. The causative agent of PD in salmon and rainbow trout is Salmon Pancreas Disease Virus (SPDV), commonly known as salmonid alphavirus (SAV). Based on sequence data of the SAV E2 structural protein and the non-structural protein 3 (nsP3), SAV strains can be assigned to six different subtypes: SAV-1, SAV-2, SAV-3, SAV-4, SAV-5 and SAV-6). The subtype SAV-2 includes isolates which, until recently, were primarily responsible for sleeping disease (SD) outbreaks in freshwater rainbow trout (*Oncorhynchus mykiss*) in Europe. While all outbreaks of SD examined to date have been as a result of infection with SAV2, outbreaks of PD have been attributed to SAV-1, -2, -3, -4, -5 and -6. Interestingly, Norwegian SPD outbreaks have been mainly caused by SAV-3, with the remaining subtypes occurring in the British Isles. However, SAV-2 outbreaks have also recently been detected in Norwegian salmon populations. Horizontal transmission of SPD has been demonstrated and is believed to be the predominant transmission route, supported by the extended survival of virus in seawater. The virus is likely endemic in historically infected areas, based on evidence that outbreaks have been shown to recur in successive generations of salmon introduced on sites despite extensive fallow periods. In support of speculations that a substantial infection reservoir might exist in the seawater environment, a recent study has presented evidence of the detection of SPDV RNA in wild marine fish both in areas of salmon farming and at locations remote from aquaculture activity. Clinical signs associated with SPD include abnormal swimming behavior and lack of appetite, while characteristic histopathological signs include severe degeneration of exocrine pancreas, cardiomyopathy and skeletal myopathy. In Ireland, outbreaks have been shown to occur at all stages of the marine production cycle and involve mortality rates of up to 48%. In Norway alone, losses due to SPD have been estimated at GBP 100 million (USD 162 million) per year with an increase in production costs of NOK 6.0 (USD 1.0) per kg or NOK 14.4 million (USD 2.5 million) per 500,000 fish. Similarly in Scotland, SPD was recently estimated to account for a 10% loss of total production. Given its increasing significance and the apparent ubiquity of the causative agent, there is a clear need for enhanced controls against SPD. To date, focus has been placed on improving husbandry conditions and reducing stress in an effort to minimize losses. This approach has been complemented by the use of a commercial inactivated whole virus vaccine of the SAV-1 subtype in Ireland and Norway. However despite the commercial availability and use of this vaccine, SPD has continued to be a major problem for the Norwegian fishing industry.

Xu et al., have recently disclosed the testing of vaccines based on SAV-3: a vaccine comprising the E2 protein, a vaccine comprising the E1 protein, a DNA vaccine encoding the E2 protein, a DNA vaccine encoding the E1 protein and an inactivated whole virus vaccine. The DNA vaccines were found to be completely ineffective. In fact the onset of mortality for the groups given a primary and then boost vaccination with the DNA vaccines was 2 days earlier than the control group. Moreover this vaccination schedule with the DNA vaccines did not induce protection different from the non-vaccinated controls. The groups given a primary vaccination with the E1 DNA or E2 DNA, followed by boost with the respective protein antigen, did not show a result significantly different from controls. It was found that the inactivated vaccine induced the best protection in comparison to the sub-unit and DNA vaccines tested (Xu, et al. Superior protection conferred by inactivated whole virus vaccine over subunit and DNA vaccines against salmonid alphavirus infection in Atlantic salmon (*Salmo salar* L.) Vaccine 30, pp. 3918-3928 (2012)).

However it has surprisingly been found that a DNA vaccine according to the invention is not only effective, but gives far superior results compared to an inactivated whole virus PD vaccine. Thus, the disclosure herein provides the first effective nucleic acid vaccine against PD.

BRIEF DESCRIPTION OF THE DRAWINGS

FIG. 1. Plasmid pUK21-A2.

FIG. 2. Construction of plasmid pUK-SPDV-poly2#57.

FIG. 3. Construction of plasmid pUK-SPDV-poly2#1.

FIG. 4. Map of plasmid pUK-SPDV-poly2#1.

FIG. 5. Nucleotide sequence encoding His-tagged SPDV structural polyprotein

FIG. 6. Nucleotide sequence encoding SPDV structural polyprotein

FIG. 7. Nucleotide sequence encoding His-tagged SPDV structural polyprotein plus vector sequence.

FIG. 8. Amino acid sequence of His-tagged SPDV polyprotein

FIG. 9. Amino acid sequence of SPDV polyprotein

FIG. 10. Amino acid sequence of capsid polypeptide

FIG. 11. Amino acid sequence of E3 polypeptide

FIG. 12. Amino acid sequence of E2 polypeptide

FIG. 13. Amino acid sequence of 6K polypeptide

FIG. 14. Amino acid sequence of E1 polypeptide

FIG. 15A-E. Histopathology studies illustrating selected parameters of heart histopathology index.

FIG. 16. Heart histopathology index corresponding to different vaccine batches.

FIG. 17A-B. Necrosis measurements.

FIG. 18A. Histopathology Index.

FIG. 18B. qPCR analysis.

FIG. 19. Safety of a 10× vaccine composition.

FIG. 20. Study showing persistence of plasmid at the site of injection.

FIG. 21-23 Dose effects.

SUMMARY OF THE DISCLOSURE

This disclosure generally relates to nucleic acids, as well as vaccines comprising said nucleic acids, wherein the vaccines are directed against the causative agent of Pancreas Disease (PD) in fish, a salmon alphavirus (SAV).

This disclosure relates to reagents and methods for protecting a host from infection by and/or tissue damage associated with infection by a salmon alphavirus (e.g., the causative agent of pancreas disease such as salmon alphavirus-1 (SAV-1), salmon alphavirus-2 (SAV-2), salmon alphavirus-3 (SAV-3), salmon alphavirus-4 (SAV-4), salmon alphavirus-5 (SAV-5), or salmon alphavirus-6 (SAV-6) or related variants thereof; preferably salmon alphavirus-1 (SAV-1), salmon alphavirus-2 (SAV-2) or salmon alphavirus-3 (SAV-3) or related variants thereof; more preferably salmon alphavirus-3 (SAV-3) or related variants thereof, more particularly preferably salmon alphavirus-3 (SAV-3)). The method for protecting a host from infection by and/or tissue damage associated with infection by a salmon alphavirus may comprise administering to the host (e.g., a salmon or rainbow trout and/or a salmon or rainbow trout infected by a salmon alphavirus) a nucleic acid molecule sharing identity with SEQ ID NO.: 2 and/or a fragment thereof and/or derivative thereof (e.g., one or more (including all of the) nucleic acid molecules encoding a protein sharing identity with at least one or all of SEQ ID NO.: 6 (capsid), SEQ ID NO.: 7 (E3), SEQ ID NO.: 8 (E2), SEQ ID NO.: 9 (6K), and/or SEQ ID NO.: 10 (E1)).

In a preferred embodiment the nucleic acid molecule according to the invention shares at least 95% identity with SEQ ID NO.: 1 or SEQ ID No. 2 (preferably SEQ ID No. 2) and/or at least 95% identity with a fragment thereof (fragment thereof being the nucleic acid encoding the polypeptide of SEQ ID No. 8 (E2) plus at least one, but not all, of the sequences selected from the group consisting of SEQ ID NO.: 6 (capsid), SEQ ID NO.: 7 (E3), SEQ ID NO.: 9 (6K), and SEQ ID NO.: 10 (E1)). Preferably a fragment thereof comprises the nucleic acid encoding the polypeptide of SEQ ID No. 8 (E2) and SEQ ID NO.: 6 (capsid), SEQ ID NO. 7 (E3) and SEQ ID NO.: 10 (E1).

In a preferred embodiment the vaccine according to the invention comprises a nucleic acid molecule sharing at least 99% identity with SEQ ID NO.: 1 or SEQ ID No. 2 (preferably SEQ ID No. 2) and/or at least 99% identity with a fragment thereof (fragment thereof being the nucleic acid encoding the polypeptide of the SEQ ID No. 8 (E2) plus at least one, but not all, of the sequences selected from the group consisting of SEQ ID NO.: 6 (capsid), SEQ ID NO.: 7 (E3), SEQ ID NO.: 9 (6K), and SEQ ID NO.: 10 (E1)).

In a more preferred embodiment the vaccine according to the invention comprises a nucleic acid molecule sharing at least 95% identity with SEQ ID NO.: 1 or SEQ ID No. 2; preferably SEQ ID No. 2.

In a particularly preferred embodiment the vaccine of the invention comprises a nucleic acid molecule sharing at least 98% identity, more preferably 99% identity with SEQ ID NO.: 1 or SEQ ID No. 2, more preferably at least 98% identity with SEQ ID No. 2, even more preferably at least 99% identity with SEQ ID No. 2.

Particularly preferably, the vaccine of the invention comprises the nucleic acid molecule of SEQ ID NO.: 2.

In another preferred embodiment the vaccine according to the invention comprises a nucleic acid molecule sharing at least 99% identity with SEQ ID NO. 3 and/or at least 99% identity with a fragment thereof (fragment thereof being the nucleic acid encoding the polypeptide of the SEQ ID No. 8 (E2) plus at least one, but not all, of the sequences selected from the group consisting of SEQ ID NO.: 6 (capsid), SEQ ID NO.: 7 (E3), SEQ ID NO.: 9 (6K), and SEQ ID NO.: 10 (E1)).

In a particularly preferred embodiment, the vaccine of the invention comprises the nucleic acid molecule of SEQ ID NO.: 3.

In certain embodiments, the nucleic acid molecule may be a plasmid. Compositions comprising such nucleic acids and/or peptides, and/or polypeptides corresponding thereto salmon alphaviruses are also disclosed. Other embodiments are also provided, as described herein.

Methods for administering a vaccine and measuring any parameter known by those of skill in the art to indicate tissue damage has occurred after exposure to an infectious agent to which the vaccine is meant to control (e.g., prophylactically or therapeutically), and comparing that one or more parameter to the same in an unvaccinated host exposed to the infectious agent to determine differences in that parameter, where a difference indicates that the vaccine is effective, are disclosed.

Other embodiments will be clear to one of ordinary skill in the art from this disclosure.

DETAILED DESCRIPTION

This disclosure relates to solutions to the current and unmet need for the treatment of diseases in fish caused by salmon alphavirus ("SAV") (e.g., pancreatic disease). Nucleic acid sequences and amino acid sequences representing the same are also provided. Nucleic acid molecules comprising such nucleic acid sequences and/or encoding such amino acid sequences are also provided. SAV polypeptides, peptides, fragments and derivatives thereof are also provided. Methods for treating and/or preventing such diseases, inducing and/or enhancing an immune response against SAV, detecting and isolating SAV are also provided.

In a preferred embodiment the invention relates to the vaccine according to the invention for use against one or more subtypes of salmon pancreatic disease virus, wherein this is selected from the group consisting of SAV-1, SAV-2, SAV-3, SAV-4, SAV-5 and SAV-6. Preferably the vaccine according to the invention is for use against SAV-1, SAV-2 or SAV-3, more preferably for use against SAV-3.

Salmon pancreatic disease virus subtype 3 is represented for example by the isolates Nor PD97-N3, Nor SavH20/03, Nor SavH10/02, Nor SavSF21/03, NOR 04 170 and NOR 07 170. These are of illustrative nature only and the invention is not limited to use against these isolates.

Methods for protecting a host from infection by and/or tissue damage associated with infection by a salmon alphavirus (e.g., the causative agent of pancreas disease such as salmon alphavirus-1 (SAV-1), salmon alphavirus-2 (SAV-2), salmon alphavirus-3 (SAV-3) or related variants thereof) may comprise administering to the host (e.g., a salmon or rainbow trout and/or a salmon or rainbow trout infected by a salmon alphavirus) a nucleic acid molecule encoding a polypeptide sharing identity with a SPDV polypeptide (e.g., SEQ ID NO.: 4 or 5, (polyprotein) preferably SEQ ID NO. 5). A SPDV polypeptide may also comprise and/or be SEQ ID No. 8 (E2) plus at least one of the sequences selected from the group consisting of SEQ ID NO.: 6 (capsid), SEQ ID NO.: 7 (E3), SEQ ID NO.: 9 (6K) and SEQ ID NO.: 10 (E1). Preferably a SPDV polypeptide comprises SEQ ID NO.: 8 (E2), SEQ ID NO 6 (capsid), SEQ ID NO.: 7 (E3), and SEQ ID NO.: 10 (E1). More preferably a SPDV polypeptide comprises SEQ ID No. 8 (E2), SEQ ID NO.: 6 (capsid), SEQ ID NO.: 7 (E3), SEQ ID NO.: 9 (6K), and SEQ ID NO.: 10 (E1).

Derivative thereof relates to substitutions to the sequence of represented by SEQ ID No. 5, which may include, for example, at least one substitution at any one or more amino acids selected from the group consisting of 21, 47, 116, 130, 141, 203, 205, 221, 269, 278, 321, 347, 351, 362, 409, 512, 550, 551, 574, 575, 583, 609, 696, 703, 726, 748, 752, 758, 765, 771, 838, 839, 840, 841, 842, 843, 844, 845, 846, 847, 848, 849, 850, 851, 852, 853, 854, 855, 856, 857, 858, 859, 892, 914, 930, 988, 1005, 1053, 1240, 1254, 1266, 1274, and/or 1303 of sequence ID NO. 5 (each combination of substitutions and non-substitutions at these positions constitutes a SPDV polypeptide) see underlined amino acids of FIGS. 8 to 14).

An exemplary SPDV polyprotein (e.g., similar to SEQ ID NO.: 4 or 5, preferably SEQ ID NO.4) or subprotein thereof (e.g., capsid, E3, E2, 6K, and/or E1 similar to any of SEQ ID NOS. 6-10) may also comprise an amino acid sequence corresponding to any one of amino acids 21, 47, 116, 130, 141, 203, 221, 269, 278, 321, 347, 351, 362, 409, 512, 550, 551, 574, 575, 583, 609, 696, 703, 726, 748, 752, 758, 765, 771, 838, 839, 840, 841, 842, 843, 844, 845, 846, 847, 848, 849, 850, 851, 852, 853, 854, 855, 856, 587, 858, 859, 892, 914, 930, 988, 1005, 1053, 1240, 1254, 1266, 1274, and/or 1303 of SEQ ID NO.: 5; e.g. underlined amino acids of FIGS. 8 to 14).

In certain embodiments, the nucleic acid molecule may be a plasmid.

In a preferred embodiment the invention relates to an isolated nucleic acid molecule encoding at least one of a polypeptide with SEQ ID NO.: 5, SEQ ID NO.: 6, SEQ ID NO.: 7, SEQ ID NO.: 8, SEQ ID NO.: 9, or SEQ ID NO.: 10.

The isolated nucleic acid molecule may comprise a sequence selected from the group consisting of SEQ ID NO.: 1, SEQ ID NO.: 2 and SEQ ID NO.: 3.

Preferably the isolated nucleic acid molecule encodes a polypeptide sequence which is at least 98% identical with SEQ ID NO.: 5, more preferably which encodes the polypeptide sequence of SEQ ID NO.: 5.

Also preferably the isolated nucleic acid molecule encodes SEQ ID NO.: 5 comprising at least one substitution at amino acid selected from the group consisting of 21, 47, 116, 130, 141, 203, 221, 269, 278, 321, 347, 351, 362, 409, 512, 550, 551, 574, 575, 583, 609, 696, 703, 726, 748, 752, 758, 765, 771, 838-859, 892, 914, 930, 988, 1005, 1053, 1240, 1254, 1266, 1274, and 1303.

In another preferred embodiment the invention relates to an isolated polypeptide comprising SEQ ID NO.: 5, SEQ ID NO.: 6, SEQ ID NO.: 7, SEQ ID NO.: 8, SEQ ID NO.: 9 or SEQ ID NO.: 10.

The isolated polypeptide may have the amino acid sequence of SEQ ID NO.: 5 comprising at least one substitution at amino acid selected from the group consisting of 21, 47, 116, 130, 141, 203, 221, 269, 278, 321, 347, 351, 362, 409, 512, 550, 551, 574, 575, 583, 609, 696, 703, 726, 748, 752, 758, 765, 771, 838-859, 892, 914, 930, 988, 1005, 1053, 1240, 1254, 1266, 1274, and 1303.

More preferably the isolated polypeptide has the amino acid sequence of SEQ ID NO.: 4.

In yet another preferred embodiment the invention relates to an isolated polypeptide sharing at least 98% identity with at any one of SEQ ID NO.: 5, SEQ ID NO.: 6, SEQ ID NO.: 7, SEQ ID NO.: 8, or SEQ ID NO.: 10.

The isolated polypeptide or peptide may share identity with a fragment of SEQ ID NO.: 5, the fragment comprising at least one of amino acids 21, 47, 116, 130, 141, 203, 221, 269, 278, 321, 347, 351, 362, 409, 512, 550, 551, 574, 575, 583, 609, 696, 703, 726, 748, 752, 758, 765, 771, 838, 839, 840, 841, 842, 843, 844, 845, 846, 847, 848, 849, 850, 851, 852, 853, 854, 855, 856, 587, 858, 859, 892, 914, 930, 988, 1005, 1053, 1240, 1254, 1266, 1274, and/or 1303 of SEQ ID NO.: 5.

In further preferred embodiment the invention relates to a method for inducing an immune response in a host against a salmon alphavirus comprising administering to the host a nucleic acid molecule as described above. In said method the nucleic acid may be a plasmid which is administered by injection into muscle tissue and is not detectable in any non-muscle tissue after 36 days. In said method preferably two to 20 micrograms of nucleic acid molecule is administered to the host, more preferably five to 10 micrograms of nucleic acid molecule is administered to the host.

In yet a further preferred embodiment the invention relates to a method for inducing an immune response in a host against a salmon alphavirus comprising administering to the host a polypeptide or peptide as described above.

In another preferred embodiment the invention relates to a vaccine comprising the nucleic acid as described above.

In another preferred embodiment the invention relates to a vaccine for use against salmon alphavirus comprising the nucleic acid as described above.

References to a percentage sequence identity between two sequences means that, when aligned, that percentage of monomers are the same in comparing the two sequences. This alignment and the percent homology or sequence identity can be determined using software programs known in the art, for example BLAST algorithm (nucleotide program: blastn, megablast, or tblastx, protein program: blastp) or by using the Smith-Waterman homology search algorithm.

Nucleic acids according to the invention are preferably provided in purified or substantially purified form i.e. substantially free from other nucleic acids. Nucleic acids of the invention may be prepared in many ways e.g. by chemical synthesis (e.g. phosphoramidite synthesis of DNA) in whole or in part, by digesting longer nucleic acids using nucleases (e.g. restriction enzymes), by joining shorter nucleic acids or nucleotides (e.g. using ligases or polymerases) from genomic or cDNA libraries etc.

The examples show that estimated standard (10 μg) and double doses (20 μg) of a PD NAV vaccine caused no mortality in vaccinated individuals for 18 days post-vaccination. Vaccine efficacy was evaluated based on severity of pancreas and heart necrosis by histopathology and presence and load of viral RNA as determined by reverse transcription quantitative real-time PCR (RT-qPCR). Evaluation of protection levels at 10 weeks (731 degree days) and 28 weeks (2050 degree days) post-vaccination revealed a strong and lasting protective response against SAV infection in both cases, with no significant increase in protection achieved by increasing vaccine dose. The PD nucleic acid vaccine was significantly superior in preventing the development of tissue necrosis in target organs and in reducing propagation of the virus in heart tissue when compared to a commercially available inactivated and adjuvanted PD vaccine. These results suggest an important role for the vaccine according to the invention against PD in supporting control policies targeting this significant disease.

These and other embodiments, as well as the advantages thereof, may be derived from this disclosure.

Tissue damage may be determined by measuring any parameter known by those of skill in the art to indicate damage has occurred. In certain embodiments, the tissue may be skeletal or cardiac muscle, for instance. The parameters measured may include, for example, any one or more of necrosis, inflammation, infiltration of tissue by mononuclear cells, infiltration of tissue by neutrophilic granulocytes, infiltration of tissue by non-lymphocytic mononuclear cells, infiltration by lymphocytes, fibrosis, myocyte regeneration, and infiltration by eosinophilic granulocytes. These parameters may be compared between, for example, a non-vaccinated and a vaccinated host or a non-infected and an infected host or combinations thereof. For instance, an exemplary method may comprise:
   a) measuring at least one parameter selected from the group consisting of necrosis, inflammation, infiltration of tissue by mononuclear cells, infiltration of tissue by neutrophilic granulocytes, infiltration of tissue by non-lymphocytic mononuclear cells, infiltration by lymphocytes, fibrosis, myocyte regeneration, and infiltration by eosinophilic granulocytes in a host;
   b) subsequently administering the vaccine against salmon alphavirus to the host; and,
   c) subsequently measuring at least one parameter selected from the group consisting of necrosis, inflammation, infiltration of tissue by mononuclear cells, infiltration of tissue by neutrophilic granulocytes, infiltration of tissue by non-lymphocytic mononuclear cells, infiltration by lymphocytes, fibrosis, myocyte regeneration, and infiltration by eosinophilic granulocytes in the host.

The host may be (e.g., by design) or may have been exposed to a salmon alphavirus before or after step a) and/or step b). A significant change in the at least one parameter measured in step a) and c) typically indicates the vaccine is effective. As the presence and/or increase of any one or more of these parameters may be associated with tissue damage, the change will typically be from the absence of one or more of these parameters (e.g., a "score" of 0) to the presence of one or more of these parameters (e.g., a "score" of 1, 2 or 3 (see the Examples)) following infection. For example, SAV3 infection has been shown to induce an early, acute, and recovery phases of infection and that tissue damage changes through the different phases. Symptoms of tissue damage are typically observed beginning at the acute stage that may be, for example, about 15-36 days after infection, with a typical maximum effect on tissue damage observed at about day 26 after infection. Thus, for example, while one or more of such parameters may be measured at a particular level (e.g., a "score" of 1, 2 or 3, for instance) in a non-vaccinated host at a particular time (e.g., 26 days) after exposure to salmon alphavirus, that parameter would typically be decreased in a vaccinated host (e.g., "scored" at 0) at the same (or similar) timepoint. Within a population of hosts, the average score of the members of the vaccinated population would typically be lower than the average score of the members of the non-vaccinated population at that timepoint. These methods may also be used to follow the progress of disease caused by or associated with the presence of salmon alphavirus in the host.

These parameters may be measured by any method available to one of ordinary skill in the art. These parameters may be compared as "scores" (e.g., as 0, 1, 2, or 3), as mentioned above. For instance, tissue damage is often observed in cardiac tissue. Accordingly, salmon hearts may be embedded in paraffin according to routine histologic procedures, cut with a microtome, stained with hematoxylin and eosin, and mounted on a glass slide with a coverslip. The heart sections may then be evaluated using brightfield microscopy where microscopic changes are regarded for severity as follows:

1) Necrosis may be characterized by the presence of dull, pale pink, individualized myocytes with rounded irregular margins and inapparent or ghost nuclei, and/or present as individual myocytes with apoptotic-like bodies or karyorrhectic nuclear material. Diagnoses of necrosis typically ranges from Grade 1 to Grade 3 as follows: Grade 1 (mild) when a single affected myocyte is visualized in one or more high power (40× objective) microscopic fields; Grade 2 (moderate) necrosis where approximately 2 to 4 necrotic cells appear in multiple high power fields (hpf); and Grade 3 (severe) where greater than four necrotic cells are observed in multiple hpf. Necrotic myocytes should also be distinguished from hypercontraction artifact, which was visualized as slightly hypereosinophilic, glassy fibers with condensed, shrunken nuclei (e.g., often located near the ventricular margins).

2) Inflammation may be characterized by the presence of lymphocytic and non-lymphocytic mononuclear cell (histiocytic) infiltrates along the epicardial surface of the heart (primarily the ventricle) and less frequently within the ventricular or atrial myocardium. Diagnoses of inflammation is typically ranged Grade 1, 2 or 3. Grade 1 (mild) inflammation typically consists of focal or multifocal mononuclear cell infiltrates, which may be epicardial. Grade 2 (moderate) inflammation is scored when epicardial infiltrates are generalized (i.e., the entire circumference of the heart was more or less affected). Grade 3 (severe) inflammation typically includes a generalized, densely cellular pattern of myocardial and epicardial infiltrates.

3) Neutrophilic Granulocyte infiltration may be scored as follows: 0: unremarkable granulocyte infiltrate; 1: mild granulocyte infiltrate; 2: moderate granulocyte infiltrate; and, 3: severe granulocyte infiltrate.

4) Non-lymphocytic mononuclear cell infiltration may be scored as follows: 0: Unremarkable histiocyte infiltrate; 1, mild histiocyte infiltrate; 2, moderate histiocyte infiltrate; and, 3, severe histiocyte infiltrate.

5) Lymphocyte infiltration may be scored as follows: 0, unremarkable lymphocyte infiltrate; 1, mild lymphocyte infiltrate; 2, moderate lymphocyte infiltrate; and, 3, severe lymphocyte infiltrate;

6) Fibrosis may be scored as follows: 0, unremarkable fibrosis; 1, mild fibrosis; 2, moderate fibrosis; and, 3, severe fibrosis.

7) Myocyte Regeneration may be characterized by the presence of streaming, pyramidal or stellate myocytes with enlarged single or multiple nuclei and slightly basophilic cytoplasm. Nuclei of affected cells may exhibit clumped, marginated chromatin and prominent nucleoli, and mitotic figures may also be observed. Myocyte regeneration, which in the majority of cases co-occurred spatially with myocyte necrosis, was generally most prominent at or near the junction of the stratum compactum and the stratum spongiosum. Diagnoses of myocyte regeneration ranged from Grade 1, 2 or 3. Grade 1 (mild) regeneration may be exemplified by a single small cluster of affected myocytes in one or more hpf. A larger, patchy area of myocyte regeneration may be scored as Grade 2 (moderate). When such areas become contiguous, the finding may be recorded as Grade 3 (severe).
8) Eosinophilic Granulocyte are typically located almost exclusively at the bulboventricular junction, typically within the base of the bulbus arteriosus itself, at the bulboventricular interface, and/or within the walls of small arteries in that region. Eosinophilic granulocytes may be characterized by obvious spherical or globular, red cytoplasmic granules and/or may be clumped, and less frequently, in the process of degranulation. Diagnoses of eosinophilic granulocytic infiltrates may be scored as Grade 1 or 2. Grade 1 (mild) eosinophilic granulocytic infiltrates are typically observed as individual scattered cells or small foci of cells, whereas a Grade 2 (moderate) diagnosis may be found when the infiltrates occupy a larger, patchy area.

The significance of these measurements may be performed using appropriate software (e.g., SAS/STAT® software). Frequencies of the ordinal histopathology scores may be obtained and weighted using the scores from the control fish using the following formula:

$$Weight_y = \left(\frac{\bar{x}}{s_x}\right) * \left(\frac{\sum x}{T}\right),$$

where
- x=the score of each variable, y, calculated separately, where
- y=Eosinophilic Granulocyte, Fibrosis, Granulocyte, Inflammation, Lymphocyte, Myocyte Regeneration, Necrosis, and Non-Lymphocytic Mononuclear Cell,
- $\bar{x}$=mean of scores for each variable, y
- $s_x$=standard deviation of scores for each variable, y, and
- T=is the grand sum of all scores.

The weights obtained may then be used as coefficients in an index to calculate a score for each sample and these scores are analyzed using analysis of variance techniques (ANOVA, SAS PROC MIXED) to determine if differences exist among treatment/batches. Descriptive statistics (mean, standard deviation, minimum, and maximum) are presented for the index score for all treatment/batches. All hypotheses are typically tested at a two-sided 0.05 level of significance, unless otherwise stated. These techniques are merely exemplary and others may also be suitable as would be understood by one of ordinary skill in the art.

The polypeptides described herein may be modified to contain substitutions that may be considered, for instance, conservative or non-conservative. A conservative substitution may be, for example, the substitution of one type of amino acid residue with a similar type of amino acid residue. A non-conservative substitution may be, for example, the substitution of one type of amino acid residue with a different type of amino acid residue. Amino acids may be similar to one another if, for example, based on size, hydrophobicity, polarity, aliphaticity (or not), aromaticity (or lack thereof), charge (positive or negative), or other attributes. Non-limiting, exemplary and preferred substitutions are shown in Table 1:

TABLE 1

| Original Residues | Exemplary Substitutions | Preferred Substitutions |
|---|---|---|
| Ala | Val, Leu, Ile | Val |
| Arg | Lys, Gln, Asn, His | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

For example, in some embodiments, substitutions may be made at any one or more of amino acids 21, 47, 116, 130, 141, 203, 221, 269, 278, 321, 347, 351, 362, 409, 512, 550, 551, 574, 575, 583, 609, 696, 703, 726, 748, 752, 758, 765, 771, 838, 839, 840, 841, 842, 843, 844, 845, 846, 847, 848, 849, 850, 851, 852, 853, 854, 855, 856, 587, 858, 859, 892, 914, 930, 988, 1005, 1053, 1240, 1254, 1266, 1274, and/or 1303 of SEQ ID NO.: 5 (including, for example, the corresponding amino acids of any of SEQ ID NOS. 6, 7, 8, 9 or 10). Alternatively, substitutions may be made at any amino acid except any one or more of residues 21, 47, 116, 130, 141, 203, 221, 269, 278, 321, 347, 351, 362, 409, 512, 550, 551, 574, 575, 583, 609, 696, 703, 726, 748, 752, 758, 765, 771, 838, 839, 840, 841, 842, 843, 844, 845, 846, 847, 848, 849, 850, 851, 852, 853, 854, 855, 856, 587, 858, 859, 892, 914, 930, 988, 1005, 1053, 1240, 1254, 1266, 1274, and/or 1303 of SEQ ID NO.: 5 (including, for example, the corresponding amino acids of any of SEQ ID NOS. 6, 7, 8, 9 or 10). Corresponding substitutions may also be made to nucleic acid sequences encoding SEQ ID NO.: 5 (e.g., any of SEQ ID NOS. 1, 2, or 3) such that the substitutions are encoded thereby. As described above, the substitutions may be conservative or non-conservative.

Nucleic acid molecules corresponding to and/or derived from and/or encoding salmon alphavirus proteins (e.g., SPDV polypeptide(s)) and/or one or more antigens (and/or immunogens) thereof may also be contained within a vector (e.g., a recombinant vector) such as one or more non-viral and/or viral vectors. "Non-viral" vectors may include, for instance, plasmid vectors (e.g., compatible with bacterial, insect, and/or mammalian host cells). Exemplary vectors may include, for example, PCR-ii, PCR3, and pcDNA3.1 (Invitrogen, San Diego, Calif.), pBSii (Stratagene, La Jolla, Calif.), pet15 (Novagen, Madison, Wis.), pGEX (Pharmacia Biotech, Piscataway, N.J.), pEGFp-n2 (Clontech, Palo Alto, Calif.), pET1 (Bluebacii, Invitrogen), pDSR-alpha (PCT pub. No. WO 90/14363) and pFASTBACdual (Gibco-BRL, Grand island, NY) as well as Bluescript plasmid derivatives (a high copy number COLe1-based phagemid, Stratagene Cloning Systems, La Jolla, Calif.), PCR cloning plasmids designed for cloning TAQ-amplified PCR products (e.g., TOPO™ TA Cloning® kit, PCR2.1® plasmid derivatives, Invitrogen, Carlsbad, Calif.). Bacterial vectors may also be used including, for instance, Shigella, Salmonella (e.g., for mucosal delivery), Vibrio cholerae, Lactobacillus, Bacille Calmette Guerin (BCG), and Streptococcus (see for example, WO 88/6626; WO 90/0594; WO 91/13157; WO 92/1796; and WO 92/21376). The vectors may be constructed using standard recombinant techniques widely available to one skilled in the art. Many other non-viral plasmid expression vectors and systems are known in the art and may be used. Various viral vectors that have been successfully utilized for introducing a nucleic acid to a host include retrovirus, adenovirus, adeno-associated virus (AAV), herpes virus, and poxvirus, among others. Viral vectors may be constructed using standard recombinant techniques widely available to one skilled in the art.

In one embodiment, such a vector may be utilized to deliver such nucleic acid molecules (e.g., to a cell in vitro or in vivo). Where such vectors are used to induce and/or enhance an immune response, the vector may also encode other proteins (e.g., co-stimulatory molecules, cytokines or chemokines) and/or be combined with other factors (e.g., exogenous cytokines) (Xiang et al., *Immunity*, 2:129-135, 1995; Kim et al., *Eur. J. Immunol.*, 28:1089-1103, 1998; Iwasaki et al., *J. Immunol.* 158:4591-3601, 1997; Sheerlinck et al., *Vaccine*, 19:2647-2656, 2001). Other strategies may also be utilized to improve the efficiency of such delivery systems including, for example, the use of self-replicating viral replicons (Caley et al., *Vaccine,* 17:3124-2135, 1999; Dubensky et al., *Mol. Med.* 6:723-732, 2000; Leitner et al., *Cancer Res.* 60: 51-55, 2000), codon optimization (Liu et al., *Mol. Ther.,* 1:497-500, 2000; Dubensky, supra; Huang, et al., *J. Virol.* 75:4947-4951, 2001), in vivo electroporation (Widera et al., *J. Immunol.* 164:4635-3640, 2000), incorporation of stimulatory motifs such as CpG (Gurunathan, supra; Leitner, supra), sequences for targeting of the endocytic or ubiquitin-processing pathways (Thomson et al., *J. Virol.* 72:2246-2252, 1998; Velders et al., *J. Immunol.* 166:5366-5373, 2001), prime-boost regimens (Gurunathan supra; Sullivan et al., *Nature* 408:605-609, 2000; Hanke et al., *Vaccine,* 16:439-445, 1998; Amara et al., *Science* 292:69-74, 2001), proteasome-sensitive cleavage sites, and the mucosal delivery systems.

Delivery techniques may include, for example, DNA-ligand complexes, adenovirus-ligand-DNA complexes, direct injection of DNA, $CaPO_4$ precipitation, gene gun techniques, electroporation, and colloidal dispersion systems. Colloidal dispersion systems include macromolecule complexes, nanocapsules, microspheres, beads, and lipid-based systems including oil-in-water emulsions, micelles, mixed micelles, and liposomes. The preferred colloidal system is a liposome, which are artificial membrane vesicles useful as delivery vehicles in vitro and in vivo. RNA, DNA and intact virions can be encapsulated within the aqueous interior and be delivered to cells in a biologically active form (Fraley, R. et al. *Trends Biochem. Sci.,* 6:77, 1981). The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Examples of lipids useful in liposomes include, for instance, phosphatidyl compounds, such as phosphatidylglycerol, phosphatidylcholine, phosphatidylserine, phosphatidyletha-nolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

As would be understood by those of ordinary skill in the art, methods for preparing and using such non-viral vectors, viral vectors, and variations thereof are available in the art. For instance, useful techniques may be found in common molecular biology references such as *Molecular Cloning: A Laboratory Manual* (Sambrook et al., Cold Spring Harbor Laboratory Press, 1989), Gene Expression Technology (Methods in Enzymology, Vol. 185, edited by D. Goeddel, 1991. Academic Press, San Diego, Calif.), and *PCR Protocols: A Guide to Methods and Applications* (Innis et al., 1990. Academic Press, San Diego, Calif.), for instance.

A cultured cell comprising nucleic acid molecules corresponding to and/or derived from and/or encoding SPDV polypeptide(s) and/or an antigen (or immunogen) thereof may also be provided. The cultured cell may be transfected and/or infected by a vector or progeny thereof such that it may express a polypeptide (e.g., an antigen). Suitable cell lines are known to those of skill in the art and are commercially available, for example, through established cell culture collections. Such cells may then be used to produce viral particles, polypeptides, reagents for detecting and/or isolating SPDV, or for other uses. An exemplary method may comprise culturing a cell comprising the nucleic acid molecule (e.g., optionally under the control of an expression sequence) under conditions that allow for the production of viral particles or expression a polypeptide. The viral particle, polypeptide and/or other reagent may then be isolated from the cell or the cell culture medium using standard techniques.

Binding agents reactive with antigens of the salmon alphaviruses described herein are also provided. For example, an antigen may include any minimum number of contiguous amino acid residues of the SPDV polypeptide(s), or any subsequence thereof. The binding agent may therefore be utilized to identify, isolate and/or remove salmon alphavirus from a sample (e.g., a biological sample). As described above, in some embodiments, binding agents may be antibodies. The term "antibody" or "antibodies" may refer to whole or fragmented antibodies in unpurified or partially purified form (e.g., hybridoma supernatant, ascites, polyclonal antisera) or in purified form, or to derivatives of antibodies. A purified antibody may be one that is separated from at least about 50%, 60%, 75%, 90%, or 95% of the proteins with which it is initially found (e.g., as part of a hybridoma supernatant or ascites preparation). The antibodies may be of any suitable origin or form including, for example, murine (e.g., produced by murine hybridoma cells), or expressed as humanized antibodies, chimeric antibodies, human antibodies, and the like. For instance, antibodies may be of any suitable type including, for example, human (e.g., IgG (IgG1, IgG2, IgG3, IgG4), IgM, IgA (IgA1 and IgA2), IgD, and IgE), canine (e.g., IgGA, IgGB, IgGC, IgGD), chicken (e.g., IgA, IgD, IgE, IgG, IgM, IgY), goat (e.g., IgG), mouse (e.g., IgG, IgD, IgE, IgG, IgM), pig (e.g., IgG, IgD, IgE, IgG, IgM), rat (e.g., IgG, IgD, IgE, IgG, IgM) and/or a fragment and/or derivative thereof (e.g., as chimeric antibodies). Suitable derivatives may include, for example, an Fab, $F(ab')_2$, Fab' single chain antibody, Fv, single domain antibody, mono-specific antibody, bi-specific antibody, tri-specific antibody, multi-valent antibody, chimeric antibody, canine-human chimeric antibody, canine-mouse chimeric antibody, antibody comprising a canine Fc, humanized antibody, human antibody, caninized, CDR-grafted antibody, shark antibody, nanobody (e.g., antibody consisting of a single monomeric variable domain), camelid antibody (e.g., antibodies of members of the Camelidae family), microbody, intrabody (e.g., intracellular antibody), or mimetic. Mimetics may also include, for example, organic compounds that specifically bind salmon alphavirus or an antigen thereof such as, for example, an affibody (Nygren, et al., *FEBS J.* 275(11):2668-76, 2008), affilin (Ebersbach, et al., J. Mol. Biol. 372 (1):172-85, 2007), affitin (Krehenbrink et al., *J. Mol. Biol.* 383(5):1058-68, 2008), anticalin (Skerra, A., *FEBS J.* 275(11):2677-83, 2008), avimer (Silverman et al., Nat. Biotechnol. 23(12): 1556-61, 2005), DARPin (Stumpp et al., *Drug Discov. Today* 13(15-16):695-701, 2008), Fynomer (Grabulovski et al., *J. Biol. Chem.* 282(5): 3196-3204, 2007), Kunitz domain peptide (Nixon et al., *Curr. Opin. Drug Discov. Devel.* 9(2):261-8, 2006), and/or a monobody (Koide et al., *Methods Mol. Biol.* 352:95-109, 2007). Other binding agents are also provided herein as would be understood by one of ordinary skill in the art.

Methods of preparing and utilizing various types of antibodies are well-known to those of skill in the art and would be suitable in practicing the present invention (see, for example, Harlow, et al. *Antibodies: A Laboratory Manual*, Cold Spring Harbor Laboratory, 1988; Harlow, et al., *Using Antibodies: A Laboratory Manual, Portable Protocol No.* 1, 1998; Kohler and Milstein, *Nature,* 256:495, 1975; Jones et al., *Nature,* 321:522-525, 1986; Riechmann et al., *Nature,* 332:323-329, 1988; Presta, *Curr. Op. Struct. Biol.,* 2:593-596, 1992; Verhoeyen et al., *Science,* 239:1534-1536, 1988; Hoogenboom et al., *J. Mol. Biol.*, 227:381, 1991; Marks et al., *J. Mol. Biol.*, 222:581, 1991; Cole et al., *Monoclonal Antibodies and Cancer Therapy*, Alan R. Liss, p. 77, 1985; Boerner et al., *J. Immunol.*, 147(1):86-95, 1991; Marks et al., Bio/Technology 10, 779-783, 1992; Lonberg et al., *Nature* 368:856-859, 1994; Morrison, *Nature* 368:812-13, 1994; Fishwild et al., *Nature Biotechnology* 14, 845-51, 1996; Neuberger, *Nature Biotechnology* 14, 826, 1996; Lonberg and Huszar, *Intern. Rev. Immunol.* 13:65-93, 1995; as well as U.S. Pat. Nos. 4,816,567, 5,545,807, 5,545,806, 5,569,825, 5,625,126, 5,633,425, and 5,661,016). In certain applications, the antibodies may be contained within hybridoma supernatant or ascites and utilized either directly as such or following concentration using standard techniques. In other applications, the antibodies may be further purified using, for example, salt fractionation and ion exchange chromatography, or affinity chromatography using Protein A, Protein G, Protein A/G, and/or Protein L ligands covalently coupled to a solid support such as agarose beads, or combinations of these techniques. The antibodies may be stored in any suitable format, including as a frozen preparation (e.g., $-20°$ C. or $-70°$ C.), in lyophilized form, or under normal refrigeration conditions (e.g., $4°$ C.). When stored in liquid form, a suitable buffer such as Tris-buffered saline (TBS) or phosphate buffered saline (PBS) may be utilized.

Where the binding agent is an antibody, it may be identified with reference to the nucleotide and/or amino acid sequence corresponding to the variable and/or complementarity determining regions ("CDRs") thereof. For instance, an exemplary binding agent that is, is derived from, or is related to the monoclonal antibody that binds SPDV or antigen thereof may comprise a heavy and/or a light chain that each comprise one or more constant and/or variable regions. The variable regions typically comprise one or more CDRs that in large part determine the binding specificity of the antibody. These monoclonal antibodies may be identified by analysis of the nucleotide sequences encoding the variable regions. The monoclonal antibodies may also be identified by analysis of the amino acid sequences of (e.g., which may be encoded by the nucleotide sequences) the variable regions. The binding agent may also be a derivative of an antibody 0 such as, for example, an Fab, $F(ab')_2$, Fab' single chain antibody, Fv, single chain, mono-specific antibody, bi-specific antibody, tri-specific antibody, multi-valent antibody, chimeric antibody, canine-human chimeric antibody, canine-mouse chimeric antibody, antibody comprising a canine $F_c$, humanized antibody, human antibody, caninized, CDR-grafted antibody, shark antibody, nanobody (e.g., antibody consisting of a single monomeric variable domain), camelid antibody (e.g., antibodies members of the Camelidae family) microbody, intrabody (e.g., intracellular antibody), and/or de-fucosylated antibody and/or derivative thereof. Mimetics of binding agents and/or antibodies are also provided. The binding agent may also comprise a detectable label and/or function/effector moiety fixably attached thereto. Functional/effector moieties may include, for example, cytotoxic drugs or toxins, or active fragments thereof such as diphtheria A chain, exotoxin A chain, ricin A chain, abrin A chain, curcin, crotin, phenomycin, enomycin, among others. Functional moieties may also include radiochemicals. In one embodiment, the effector moieties may be fixably attached to the binding agents. In one example, the detectable labels are fixably attached to the binding agents by chemical bonds. In one example, the chemical bonds are covalent chemical bonds. In one example, the effector moieties are conjugated to the binding agents.

The skilled artisan has many suitable techniques available for using the binding agents (e.g., antibodies) described herein to identify biological samples containing proteins that bind thereto. For instance, antibodies may be utilized to isolate salmon alphavirus and/or an antigen thereof using, for example, immunoprecipitation or other capture-type assay. This well-known technique may be performed by attaching the antibody to a solid support or chromatographic material (e.g., a bead coated with Protein A, Protein G and/or Protein L), contacting a sample (e.g., a solution) either containing or believed to contain the salmon alphavirus and/or an antigen thereof (e.g., a biological sample such as blood) with the material such that the salmon alphavirus and/or an antigen thereof binds to the antibody, thereby separating it from other components in the sample. The bound salmon alphavirus and/or an antigen thereof may then be separated from the antibody and analyzed as desired. Similar methods for isolating salmon alphavirus and/or an antigen thereof using a binding agent are well-known in the art. The binding agents (e.g., antibodies) may also be utilized to detect, isolate, and/or remove salmon alphavirus and/or an antigen thereof within or from a biological sample. Assays such as, for example, flow cytometric analysis, ELISA, immunoblotting (e.g., western blot), in situ detection, immunocytochemistry, and/or immunohistochemistry may be utilized in such methods. Other uses for the binding agents described herein may also be suitable, as would many other methods and/or assay systems.

In certain embodiments, preparations and/or compositions comprising the nucleic acids according to the invention are also provided. For example, a preparation or composition may comprise, for example, a salmon alphavirus, nucleic acid, as a partially purified (e.g., about any of 50%, 60%, 75%, 90%, 95% purity (e.g., w/w)) or purified (e.g., about 98-100% (w/w)) preparation or composition. Typically, such preparations include a buffer such as phosphate- or tris-buffered saline (PBS or TBS, respectively). The preparations may also be formulated to contain excipients, like stabilizers, for example. The nucleic acids according to the invention may also be combined with one or more pharmaceutically acceptable carriers prior to use (e.g., administration to a host). A pharmaceutically acceptable carrier may be a material that is not biologically or otherwise undesirable, e.g., the material may be administered to a cell and/or subject, without causing significant undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Suitable pharmaceutical carriers and their formulations that may be suitable are available to those of ordinary skill in the art as described in, for example, *Remington's: The Science and Practice of Pharmacy*, $21^{st}$ *Edition*, David B. Troy, ed., Lippicott Williams & Wilkins (2005). Typically, an appropriate amount of a pharmaceutically-acceptable salt is used in the formulation to render the formulation isotonic. Examples of the pharmaceutically-acceptable carriers include, but are not limited to, sterile water, saline, buffered solutions like Ringer's solution, and dextrose solution. The pH of the solution is generally from about 5 to about 8 or from about 7 to about 7.5. Other carriers include sustained-release preparations such as semipermeable matrices of solid hydrophobic polymers containing polypeptides or fragments thereof. Matrices may be in the form of shaped articles, e.g., films, liposomes or microparticles. It will be apparent to those persons skilled in the art that certain carriers may be more preferable depending upon, for instance, the route of administration and concentration of composition being administered. Pharmaceutical compositions may also include carriers, thickeners, diluents, buffers, preservatives, surface active agents, adjuvants, immunostimulants, in addition to the binding agent and/or nucleic acid. Pharmaceutical compositions may also include one or more active ingredients such as antimicrobial agents, antiinflammatory agents and anesthetics. Adjuvants may also be included in the immunuostimulatory compositions to stimulate or enhance the immune response. Non-limiting examples of suitable classes of adjuvants include those of the gel-type (e.g., aluminum hydroxide/phosphate ("alum adjuvants"), calcium phosphate, microbial origin (muramyl dipeptide (MDP)), bacterial exotoxins (cholera toxin (CT), native cholera toxin subunit B (CTB), *E. coli* labile toxin (LT), pertussis toxin (PT), CpG oligonucleotides, BCG sequences, tetanus toxoid, monophosphoryl lipid A (MPL) of, for example, *E. coli, Salmonella minnesota, Salmonella typhimurium*, or *Shigella exseri*), particulate adjuvants (biodegradable, polymer microspheres), immunostimulatory complexes (ISCOMs)), oil-emulsion and surfactant-based adjuvants (Freund's incomplete adjuvant (FIA), microfluidized emulsions (MF59, SAF), saponins (QS-21)), synthetic (muramyl peptide derivatives (murabutide, threony-MDP), nonionic block copolymers (L121), polyphosphazene (PCPP), synthetic polynucleotides (poly A:U, poly I:C), thalidomide derivatives (CC-4407/ACTIMID), RH3-ligand, or polylactide glycolide (PLGA) microspheres, among others. Metallic salt adjuvants such as alum adjuvants are well-known in the art as providing a safe excipient with adjuvant activity. The mechanism of action of these adjuvants are thought to include the formation of an antigen depot such that antigen may stay at the site of injection for up to 3 weeks after administration, and also the formation of antigen/metallic salt complexes which are more easily taken up by antigen presenting cells. In addition to aluminium, other metallic salts have been used to adsorb antigens, including salts of zinc, calcium, cerium, chromium, iron, and berilium. The hydroxide and phosphate salts of aluminium are the most common. Formulations or compositions containing aluminium salts, antigen, and an additional immunostimulant are known in the art. An example of an immunostimulant is 3-de-O-acylated monophosphoryl lipid A (3D-MPL). Other homologs and/or derivatives of any of these toxins may also suitable, provided that they retain adjuvant activity.

The salmon alphavirus, nucleic acids corresponding thereto (e.g., contained within a vector), polypeptides and/or peptides corresponding thereto, and/or binding agents may be used, for example, to stimulate an immune response against salmon alphavirus described herein in a host. In some embodiments, immunogenic compositions and vaccines comprising SPDV polypeptide(s) (e.g., SEQ ID NO.: 4 or a fragment thereof), and/or nucleic acid corresponding thereto (e.g., SEQ ID NO.: 1 or a fragment thereof) may be used to treat diseases caused by or associated with the presence of salmon alphavirus in salmon). An immunological composition is one that, upon administration to a host such as salmon induces or enhances an immune response directed against the antigen or immunogen (e.g., SPDV polypeptide(s)) contained within the composition. This response may include the generation of antibodies (e.g, through the stimulation of B cells) or a T cell-based response (e.g., a cytolytic response). These responses may or may not be protective or neutralizing. A protective or neutralizing immune response is one that may be detrimental to the cell containing or expressing the antigen (e.g., from which the antigen was derived) and beneficial to the host (e.g., by reducing or preventing tumor growth). As used herein, protective or neutralizing antibodies and/or cellular responses may be reactive to SPDV polypeptide(s) and/or an antigen thereof. An immunological composition that, upon administration to a host, results in a protective or neutralizing immune response may be considered a vaccine Immunological compositions comprising at least one SPDV polypeptide, SPDV nucleic acid molecule, and/or antigen thereof or encoded thereby may also include one or more additional antigens.

Methods for treating disease caused by or associated with salmon alphavirus in a host by administering to the host at least one or more effective doses of one or more nucleic acids, polypeptides, peptides, and/or binding agents described herein are also provided. For instance, a salmon alphavirus (e.g., inactivated) and/or SPDV polypeptide and/or nucleic acid molecule corresponding thereto (e.g., encoding a SPDV polypeptide), may be administered to a host in a suitable dose (e.g., about $10^4$, $10^5$, $10^6$, $10^7$ or $10^8$ viral particles) and dosing schedule (e.g., once, twice, or three times a day/week/month), as may be determined by one of ordinary skill in the art. A polypeptide and/or peptide may be administered to a host in a suitable dose (e.g., about 1-100 mg/kg body weight or 1-40 micrograms) and dosing schedule (e.g., once, twice, or three times a day/week/month), as may be determined by one of ordinary skill in the art. A SPDV polypeptide and/or binding agent may be administered in a suitable dosage (e.g., about 1-50 mg/kg of body weight), about 1 to about 30 mg/kg, or about 1 to about 40 mg/kg (e.g., about any of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, or 40 mg/kg). A SPDV polypeptide and/or binding agent may also be administered in a suitable dosage (e.g., about 1-50 micrograms), about 1 to about 40 micrograms, or about 2 to about 30 micrograms (e.g., about any of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, or 40 micrograms). Preferably the SPDV polypeptide and/or binding agent may be administered in a dosage between 5 and 20 micrograms, more preferably between 5 and 10 micrograms. In certain embodiments, these reagents may be administered via any route (e.g., bath immersion, intraperitoneally, intradermally, intravenously, orally, or intramuscularly) at one or more times. Preferably the dose is administered intramuscularly. When multiple doses are administered, the doses may comprise about the same or different types and or amounts of reagent (e.g., in a prime-boost format). The doses may also be separated in time from one another by the same or different intervals. For instance, the doses may be separated by about any of 6, 12, 24, 36, 48, 60, 72, 84, or 96 hours, one week, 1.5 weeks, two weeks, 2.5 weeks, three weeks, 3.5 weeks, one month, 1.5 months, two months, 2.5 months, three months, 3.5 months, four months, 4.5 months, five months, 5.5 months, six months, 6.5 months, seven months, 7.5 months, eight months, 8.5 months, nine months, 9.5 months, 10 months, 10.5 months, 11 months, 11.5 months, 12 months, 1.5 years, 2 years, or any time period before, after, and/or between any of these time periods. Preferably these reagents are administered in a single administration. In in a preferred embodiment, in the case of salmon, the administration should be once or twice, given at a young age, for example when the fish weigh 10-30 g.

some embodiments, the binding agents may be administered in conjunction with other agents (e.g., chemotherapeutic agents), as described above. Such other agents may be administered about simultaneously with the binding agents, or at a different time and/or frequency. Other embodiments of such methods may also be appropriate as could be readily determined by one of ordinary skill in the art. Generally, a dose has the effect of decreasing the number of salmon alphaviruses, or the effects of infection by salmon alphaviruses (e.g., tissue damage), in a fish is called an effective dose. Methods for preparing and/or using such preparations are well-known in the art.

In some embodiments, methods for detecting salmon alphavirus and/or antigens thereof using binding agents are provided. In certain embodiments, cells expressing SPDV polypeptide antigen(s) a fish, may be detected by contacting a test biological sample with a binding agent and detecting the same bound to the cells (e.g., using flow cytometry). In certain embodiments, the method may comprise comparing the amount of binding to the test biological sample or components thereof to the amount of binding to a control biological sample or components thereof, wherein increased binding to the test biological sample or components thereof relative to the control biological sample or components thereof indicates the presence of a SPDV in the test biological sample. Such methods are also provided in an in vivo and/or in vitro format. In some embodiments, methods for decreasing the viability and/or number of salmon alphavirus in a host using such the nucleic acids and/or binding agents described herein are also provided.

To assist the skilled artisan in using the nucleic acids and/or binding agents described herein, the same may be provided in kit format. A kit including such nucleic acids and/or binding agents (e.g., antibodies) and optionally other components necessary for using the same to detect, isolate and/or remove salmon alphavirus and/or antigen in and/or from a biological sample (e.g., cell or fluid) thereof is also provided herein. The nucleic acids and/or binding agents of the kit may be provided in any suitable form, including frozen, lyophilized, or in a pharmaceutically acceptable buffer such as TBS or PBS. The kit may also include other reagents required for utilization of the antibodies in vitro or in vivo such as buffers (e.g., TBS, PBS), blocking agents (solutions including nonfat dry milk, normal sera, Tween-20 Detergent, BSA, or casein), and/or detection reagents (e.g., goat anti-mouse IgG biotin, streptavidin-HRP conjugates, allophycocyanin, B-phycoerythrin, R-phycoerythrin, peroxidase, and/or detectable label) and other labels and/or staining kits (e.g., ABC Staining Kit, Pierce). The kits may also include other reagents and/or instructions for using the antibodies in commonly utilized assays described above such as, for example, flow cytometric analysis, ELISA, immunoblotting (e.g., western blot), in situ detection, immunocytochemistry, immunhistochemistry. In one embodiment, the detectable labels may be fixably attached to the binding agents. In one example, the detectable labels are fixably attached to the binding agents by chemical bonds. In one example, the chemical bonds are covalent chemical bonds. In one example, the detectable labels are conjugated to the binding agents.

In one embodiment, the kit provides a monoclonal antibody against SPDV polypeptide(s) and/or an antigen thereof in purified form. The monoclonal antibody may be provided in biotinylated form either alone or along with an avidin-conjugated detection reagent (e.g., antibody). The kit may include fluorescently-labelled antibodies that may be used to directly detect salmon alphaviruses and/or an antigen thereof. Buffers and the like required for using any of these systems are well-known in the art and may be prepared by the end-user or provided as a component of the kit. The kit may also include a solid support containing positive- and negative-control protein and/or tissue samples. For example, kits for performing spotting or western blot-type assays may include control cell or tissue lysates for use in SDS-PAGE or nylon or other membranes containing pre-fixed control samples with additional space for experimental samples. Kits for visualization of salmon alphaviruses and/or an antigen thereof on slides may include pre-formatted slides containing control cell or tissue samples with additional space for experimental samples. As mentioned above, the binding agents described herein and/or derivatives thereof may also be incorporated into compositions for use in vitro or in vivo. Other embodiments are also provided as would be understood by one of ordinary skill in the art.

Thus, this disclosure provides, for example: an isolated nucleic acid sequence encoding a polypeptide having the amino acid sequence of an "SPDV polypeptide" including but not limited to SEQ ID NO.: 4; SEQ ID NO.: 5; a polypeptide having the amino acid sequence of SEQ ID NO.: 6, SEQ ID NO.: 7, SEQ ID NO.: 8, SEQ ID NO.:9, and SEQ ID NO.: 10; a polypeptide having the amino acid sequence of SEQ ID NO.: 6, SEQ ID NO.: 7, SEQ ID NO.: 8, and SEQ ID NO.: 10; a polypeptide having the amino acid sequence of at least two of SEQ ID NO.: 6, SEQ ID NO.: 7, SEQ ID NO.: 8, SEQ ID NO.: 9, and/or SEQ ID NO.: 10; a polypeptide having the amino acid sequence of SEQ ID NO.: 8 and at least one of SEQ ID NO.: 6, SEQ ID NO.: 7, SEQ ID NO.: 9, and SEQ ID NO.: 10; a polypeptide having the amino acid sequence of SEQ ID NO.: 5 comprising at least one substitution at amino acid selected from the group consisting of 21, 47, 116, 130, 141, 203, 221, 269, 278, 321, 347, 351, 362, 409, 512, 550, 551, 574, 575, 583, 609, 696, 703, 726, 748, 752, 758, 765, 771, 838-859, 892, 914, 930, 988, 1005, 1053, 1240, 1254, 1266, 1274, and 1303; and/or, a polypeptide having the amino acid sequence of SEQ ID NO.: 5 comprising at least one substitution at amino acid other than at least one of amino acid 21, 47, 116, 130, 141, 203, 221, 269, 278, 321, 347, 351, 362, 409, 512, 550, 551, 574, 575, 583, 609, 696, 703, 726, 748, 752, 758, 765, 771, 838-859, 892, 914, 930, 988, 1005, 1053, 1240, 1254, 1266, 1274, or 1303; including but not limited to fragments and/or derivatives thereof. A suitable fragment may include, for example, a polypeptide or peptide sharing identity with SEQ ID NO.: 6, SEQ ID NO.: 7, SEQ ID NO.: 8, and/or SEQ ID NO.: 10, the fragment comprising at least one of amino acids 21, 47, 116, 130, 141, 203, 221, 269, 278, 321, 347, 351, 362, 409, 512, 550, 551, 574, 575, 583, 609, 696, 703, 726, 748, 752, 758, 765, 771, 838, 839, 840, 841, 842, 843, 844, 845, 846, 847, 848, 849, 850, 851, 852, 853, 854, 855, 856, 587, 858, 859, 892, 914, 930, 988, 1005, 1053, 1240, 1254, 1266, 1274, and/or 1303 of SEQ ID NO.: 5. An isolated polypeptide may, for example, share identity with SEQ ID NO.: 9 (e.g., be identical to) and at least 98% identity with at any one of SEQ ID NO.: 5, SEQ ID NO.: 6, SEQ ID NO.: 7, SEQ ID NO.: 8, and/or SEQ ID NO.: 10. To share identity, one polypeptide and/or nucleotide sequence may share any of, for instance, about 60%, about 70%, about 75%, about 80%, about 85%, about 90%, about 95%, or about 99% of the same or similar amino acids and/or nucleotides. The polypeptides, peptides, fragments and/or derivatives encoded by such nucleic acid sequences are also provided. The nucleic acids, polypeptides, peptides, fragments and/or derivatives provided herein may also be combined in any manner.

Also provided are expression vectors comprising or encoding the SPDV polypeptides, and/or a complementary or similar nucleic acid sequence, and/or a similar amino acid sequence; a host cell comprising or encoding a nucleic acid encoding an SPDV polypeptide and/or a complementary or similar nucleic acid sequence, and/or a similar amino acid sequence; an oligonucleotide having a nucleic acid sequence corresponding to a fragment of at least nine contiguous nucleotides of any of SEQ ID NOS.: 1-3, complementary to a fragment of at least nine contiguous nucleotides of any of SEQ ID NOS.: 1-3, corresponding to a nucleic acid sequence encoding a fragment of at least three contiguous amino acids of a SPDV polypeptide, or complementary to a nucleic acid sequence encoding a fragment of at least three contiguous amino acids of a SPDV polypeptide; an oligonucleotide corresponding to or complementary to at least nine contiguous nucleotides of any of SEQ ID NOS.: 1-3; two or more oligonucleotides for amplifying a nucleic acid sequence, each oligonucleotide comprising a nucleic acid sequence corresponding to a fragment of a SPDV polypeptide (e.g., at least nine contiguous nucleotides of any of SEQ ID NOS.: 1-3 or a complement thereof, or encoding a fragment of at least three contiguous amino acids of a SPDV polypeptide; methods for detecting and/or identifying and/or quantifying a virus in a sample (e.g., a biological sample such as serum) using such reagents; a kit for the detection of nucleic acid of a virus in a sample, the kit comprising an oligonucleotide, oligonucleotides, and/or primer pair for detecting and/or identifying and/or quantifying an SPDV polypeptide, the kit further optionally comprising a solid support, and/or one or more amplification reagents; a composition comprising a pharmaceutically acceptable carrier and a nucleic acid or complement thereof and/or a peptide and/or polypeptide corresponding to a SPDV polypeptide (which may be an immunogenic composition and/or a vaccine); a method of producing a nucleic acid molecule, peptide and/or polypeptide corresponding to a SPDV polypeptide, the method comprising transfecting a host cell with an expression vector encoding the peptide or polypeptide, culturing the host cell such that nucleic acid molecule, peptide and/or polypeptide is expressed, and isolating the peptide or polypeptide; a method of eliciting an immune response in a mammal by administering to the mammal a pharmaceutical composition comprising a nucleic acid molecule, peptide, and/or polypeptide corresponding to SPDV polypeptide(s), and/or host cell comprising or expressing the same; a method of generating a binding agent (e.g., antibody) against a nucleic acid, peptide and/or polypeptide corresponding to SPDV polypeptide(s) and the binding agent(s) produced thereby (e.g., reactive with a polypeptide encoded by any of SEQ ID NOS. 1-3, such as a fragment of at least 9 nucleotides thereof). Other embodiments are also provided by this disclosure as would be recognized by one of ordinary skill in the art.

Any indication that a feature is optional is intended to provide adequate support for claims that include closed or exclusive or negative language with reference to the optional feature. Exclusive language specifically excludes the particular recited feature from including any additional subject matter. For example, if it is indicated that A can only be drug X, such language is intended to provide support for a claim that explicitly specifies that A consists of X alone, or that A does not include any other drugs besides X. "Negative" language explicitly excludes the optional feature itself from the scope of the claims. For example, if it is indicated that element A can include X, such language is intended to provide support for a claim that explicitly specifies that A does not include X. Non-limiting examples of exclusive or negative terms include "only," "solely," "consisting of," "consisting essentially of," "alone," "without", "in the absence of (e.g., other items of the same type, structure and/or function)" "excluding," "not including", "not", "cannot," or any combination and/or variation of such language.

All publications and patents cited in this specification are herein incorporated by reference as if each individual publication or patent were specifically and individually indicated to be incorporated by reference. Genbank records referenced by GID or accession number, particularly any polypeptide sequence, polynucleotide sequences or annotation thereof, are incorporated by reference herein. The citation of any publication is for its disclosure prior to the filing date and should not be construed as an admission that the present invention is not entitled to antedate such publication by virtue of prior invention.

Certain embodiments are further described in the following examples. These examples are provided as examples only and are not intended to limit the scope of the claims in any way.

EXAMPLES

Example 1

Following translation and cleavage, the polyprotein sequence of alphaviruses produces at least six distinct proteins, including capsid protein, spike glycoproteins E3 and E1, envelope glycoprotein E2, a 6K protein, and p62 protein, an uncleaved combination of glycoproteins E2 and E3 (Strauss and Strauss, 1994; Weston et al., 1999; Villoing et al., 2000). The capsid protein possesses a protease activity that results in its autocatalytic cleavage from the nascent polyprotein during translation. The capsid protein then associates with viral RNA and self-assembles into icosahedral core particles. The E1 glycoprotein is a class II viral fusion protein, and the E2 glycoprotein is responsible for viral attachment to target host cells. The 6K protein is a constitutive membrane protein involved in glycoprotein processing, membrane permeabilization, and budding of viral particles. The function of the E3 glycoprotein is currently unknown. As described below, an expression vector encoding each of these proteins of salmon alphavirus (SPDV) was constructed.

The original parental plasmid (pUK21) is a synthetic plasmid obtained from Qiagen GmbH (Max-Volmer Straβe 4, Hilden, Germany) as a cloning vector carrying the kanamycin resistance gene. It was modified in the laboratory of Dr. Heather L. Davis (Loeb Health Research Institute, Ottawa, ON, Canada) to become an eukaryotic expression vector called pUK21-A2 by insertion of the human cytomegalovirus (CMV) major intermediate-early promoter and the bovine growth hormone polyadenylation signal (BGH pA) (Krieg et al., 2004). Deoxyribonucleic acid (DNA) fragments encoding the CMV promoter and the BGH pA were obtained from the pcDNA3 vector (Invitrogen Corporation, Carlsbad, Calif., USA), and were amplified from the original vector by polymerase chain reaction (PCR) for insertion in the pUK21 vector. The only phenotype conferred to host bacterial cells by the pUK21-A2 vector (FIG. 1) is kanamycin (Kan) resistance. There are no sequences for plasmid transfer to other bacteria by conjugation. The pUK21-A2 plasmid contains the ColE1 replicon (Bolivar et al., 1977a, 1977b). Under normal conditions of growth, a minimum of 15-20 copies of plasmids carrying this replicon are maintained in each bacterial cell (Covarrubias et al., 1981). However, introduction of mutations in the replicon have increased the plasmid copy number (Scott 1984). The ColE1 replicon requires host enzymes for replication, but not plasmid encoded functions (Tomizawa et al., 1975). The CMV promoter and the BGH pA signal allow expression of the gene inserted in the multiple cloning site once the plasmid is introduced in eukaryotic cells. The pUK21-A2 vector is a synthetic plasmid and therefore it has no natural host. Under laboratory conditions, *Escherichia coli* is the only known and tested host. The pUK21-A2 plasmid has the modified ColE1 origin of replication to allow high copy number replication in bacterial cells. In addition to the bacterial promoter used for expression of the kanamycin resistance gene, the vector also contains the lac promoter located immediately upstream of the first 12 nucleotides encoding the lac Z fragment for α-complementation. The full lac Z-α fragment, present in the parental pUK21 plasmid, was disrupted by insertion of the CMV promoter and BGH pA signal, and is no longer functional. The plasmid contains a region, located between the CMV promoter and Kan resistance gene that has high homology to the origin of replication of bacteriophage M13. However, the origin is non-functional due to a 72 bp deletion within the region. The T7 promoter is present and found upstream of the CMV promoter. It will only be active in the presence of T7 polymerase, and all bacterial seeds were tested and clean of bacteriophage. The pUK21-A2 vector contains the human CMV major intermediate-early promoter/enhancer region for expression of the recombinant proteins. It also contains the BGH pA signal for efficient transcription termination and polyadenylation of messenger Ribonucleic acid (mRNA). No other known control elements for eukaryotes are located in the vector.

The recombinant pUK-SPDV-poly2#1 plasmid (FIG. 3) contains the entire open reading frame (ORF) of the structural polyprotein of SPDV (FIGS. 5-14). To construct the recombinant plasmid, viral RNA was first isolated from partially purified SPDV, isolated from Atlantic salmon tissues collected during an outbreak in Scotland, and grown in tissue culture. This isolate showed high homology to SAV-2 reference sequences in Genbank (98% identity at the nucleotide level and 96% identity at the amino acid level with the sequence with GenBank ref AJ238578; also 97% identity at the nucleotide level and 92% identity at the amino acid level with the sequence with the GenBank ref AJ316246).

The gene encoding the structural polyprotein was then reverse transcribed and amplified by PCR using specific primers designed from nucleotide sequences published in GenBank. The nucleotide sequence of the forward primer, SPDV-CAP-NotI-His(F2) is shown below:

```
                                        (SEQ ID NO.: 11)
GGGCGGCCGC*ATG*CATCATCACCATCACCATATGTTTCCCATGC

AATTCACCAACTC.
```

The primer included a NotI restriction site (underlined), the coding sequence for six histidines or His tag epitope (double underlined), an ATG, start codon for the ORF (bold italic), as well as the original ATG of the viral polyprotein start codon (bold only). The nucleotide sequence of the reverse primer, SPDV-EI-EcoRI(R2) is shown below:

```
                                        (SEQ ID NO.: 12)
AT<u>GAATTC</u>GCAATTTGTATACCGGAAT***TTA***GCTCTTGA
```

This primer includes an EcoRI restriction site (underlined) as well as the complement of the stop codon TTA (bold italic) defining the end of the ORF. The 4018 bp amplicon (including primers) was cloned into the expression vector pUK21-A2. Both the PCR product and the pUK21-A2 vector were digested with restriction enzymes NotI and EcoRI. The digested products were ligated together using T4 DNA ligase then transformed in *E. coli* DH5-α competent host. One clone, pUK-SPDV-poly2#57 (FIG. 2), was selected and submitted to sequencing analysis. Alignment of the resulting nucleotide sequence to the reference indicated that the amplicon was integral except for a 150 bp deletion within the E1 glycoprotein sequence (nucleotide position 3434-3584 of the ORF). The deletion was rectified by subcloning a PCR fragment created from viral complementary DNA (cDNA) using the forward primer SPDV-E1-EcoRV (AACTATGTCAAAC-CCAATGATCTGTACG (SEQ ID NO.: 13)), designed to anneal 2 bp upstream of a naturally occurring EcoRV site, and the reverse primer SPDV-EcoRI(R2) as described above. The PCR amplicon and plasmid pUK-SPDV-poly2#57 were individually digested with EcoRV and EcoRI, ligated, and transformed into competent *E. coli* DH5-α cells. Resulting clones were screened and sequenced to ensure that the full-length nucleotide sequence (SEQ ID NO.:1; FIG. 5) encoding the SPDV polyprotein (SEQ ID NOS.: 4, 5; FIGS. 8 and 9) was present, and the plasmid pUK21-SPDV-poly2#1 (FIG. 3) was selected as the final DNA vaccine prototype. It is noted that a nucleotide sequence coding a span of six histidine residues was introduced in-frame at the 5' end of the viral polyprotein sequence to facilitate identification of the fusion protein using immunodetection and purification using nickel-agarose affinity resins or spin columns. In addition, CpG motifs are present (three murine (GA/AA) CGTT motifs and two human/primate GTCGTT motifs (e.g., envelope glycoprotein E2 contains 1 GACGTT motif in the pUK-SPDV-poly2#1 plasmid) (Jorgensen et al., 2003; Strandskog et al., 2007). During the cloning process, restriction enzyme sites located between the NotI and EcoRI sites within the multiple cloning site (MCS) were lost due to the introduction of the structural polyprotein sequence. No other restriction sites were lost or gained elsewhere in the plasmid backbone or within the ORF of the polyprotein. The ORF of the polyprotein was inserted under control of the human CMV major intermediate-early enhancer/promoter and the BGH pA signal for efficient expression in eukaryotic cells. No alphavirus control sequences were cloned along with the structural polyprotein gene based on current knowledge of this type of virus.

Example 2

A well-known symptom of infection by salmon alphavirus is tissue damage (e.g., necrosis of cardiac tissue). While previous attempts to vaccinate salmon using recombinant protein or nucleic acids may have provided some measure of protection against infection, those vaccines were not able to ameliorate tissue damage. As described below, it was surprisingly found that the expression vectors described herein (e.g., encoding SEQ ID NO.: 3; pUK-SPDV-poly2#1 plasmid (also referred to as "PD-NAV")) provide both a protection against and a reduction in tissue damage associated with infection by SAV. In addition, a method for measuring vaccine efficacy by associating the same with the measurement of one or more specific parameters is also described. A study was performed to demonstrate the efficacy of the PD-NAV when administered intramuscularly (i.m.) to Atlantic salmon (*Salmo salar*) at a particular dose using a fresh water cohabitation challenge model and to demonstrate consistency of efficacy amongst conformance lots using heart histopathological scores. Fish with an average bulk weight 16.9 g (15.97-19.14 g) were used. A single dose (0.05 mL) of the vaccine containing between 10.5 and 12.5 μg total DNA in 0.05 mL in PBS, was administered via intramuscular (i.m.) injection.

The study consisted of one tank with fish randomized into one of four treatment/batches (one control (saline) group and three batches of PD-NAV) (100 fish/group). 396 degree days elapsed before challenge with SAV3. Fish were challenged with SAV3 by introducing trojan salmon intraperitoneally (i.p.) injected with SAV3 (0.1 mL, 1.33×10$^8$ TCID50/mL) at 20% of tank population. Vaccinated fish were kept at 11.0±0.9° C. After challenge the temperature was raised to the permissive temperature for PD, 14±2° C. 24 days post-challenge histopathogical samples were taken.

Figure 15E:
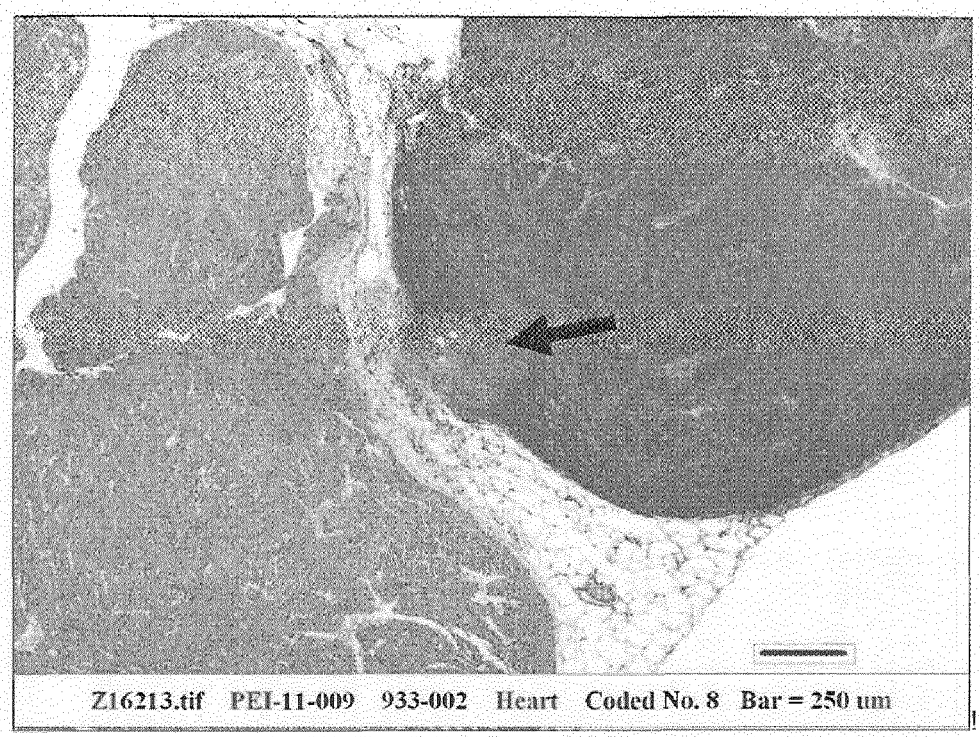
Figure 16:
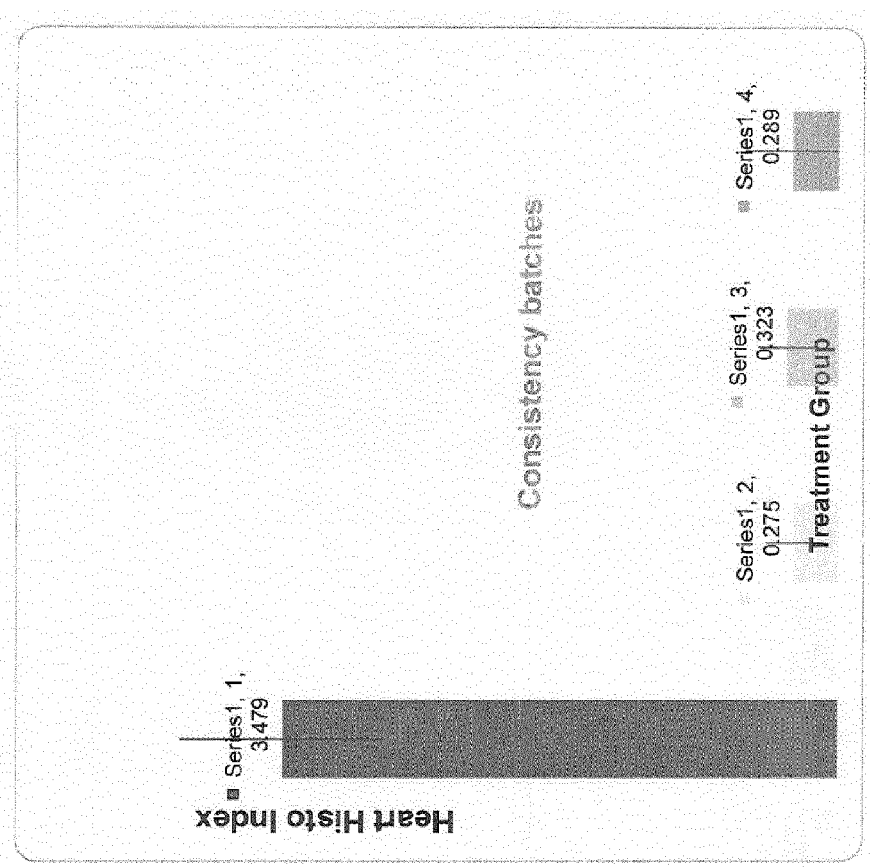

Preserved bisected salmon hearts were submitted by Novartis Animal Health (NAH) Canada, Inc., Victoria, PE, and received by Experimental Pathology Laboratories, Inc. (EPL®), Sterling, Va., for histopathologic processing and evaluation. The heart samples, which were preserved originally in 10% NBF, were transferred to individually labelled fresh containers of 10% NBF upon arrival at EPL. No further trimming of the specimens was required. Each bisected heart was oriented in a tissue cassette for longitudinal sectioning, and was embedded in paraffin according to routine histologic procedures. A single 4-6 mm section was microtomed from each heart, stained with hematoxylin and eosin, and mounted on a glass slide with a coverslip. The heart sections were evaluated using brightfield microscopy, and during these assessments, the pathologist was unaware of the treatment group status of individual fish ("blinded"). According to the protocol, microscopic changes were graded for severity as follows:

1) Necrosis occurred predominately within the ventricular myocardium, was characterized by the presence of dull, pale pink, individualized myocytes with rounded irregular margins and inapparent or ghost nuclei. Less commonly, necrosis presented as individual myocytes with apoptotic-like bodies or karyorrhectic nuclear material. Diagnoses of necrosis ranged from Grade 1 to Grade 3. Necrosis was recorded as Grade 1 (mild) when a single affected myocyte was visualized in one or more high power (40× objective) microscopic fields. Grade 2 (moderate) necrosis consisted of approximately 2 to 4 necrotic cells in multiple high power fields (hpf) (FIG. 15A (arrows=necrotic myocytes)). In Grade 3 (severe) necrosis, greater than 4 necrotic cells were observed in multiple hpf. It was necessary in this study to distinguish necrotic myocytes from hypercontraction artifact, which was visualized as slightly hypereosinophilic, glassy fibers with condensed, shrunken nuclei. Hypercontraction artifact was often located near the ventricular margins (FIG. 15B), and frequently present at any cut edge, but it was not uncommon to additionally find small patches of hypercontraction artifact in mid myocardial regions. By convention, such tissue collection artifacts were not recorded as diagnostic findings.

2) Inflammation was characterized by the presence of lymphocytic and non-lymphocytic mononuclear cell (histiocytic) infiltrates along the epicardial surface of the heart (primarily the ventricle) and less frequently within the ventricular or atrial myocardium. As per the study protocol, separate diagnoses of lymphocytic and non-lymphocytic mononuclear cell infiltration were recorded independent of, and in addition to, diagnoses of inflammation; however, both cell types were virtually always evident in relatively comparable proportions in hearts with epicardial or myocardial inflammation. Conversely, activated (epithelioid) macrophages were never observed as a component of the inflammation. Diagnoses of inflammation (FIG. 15C) ranged from Grade 1 to Grade 2, but Grade 2 inflammation was observed almost exclusively in control fish. Grade 1 (mild) inflammation consisted of focal or multifocal mononuclear cell infiltrates, which were most frequently epicardial. Inflammation was considered Grade 2 (moderate) when epicardial infiltrates were generalized (i.e., the entire circumference of the heart was more or less affected). Grade 3 (severe) inflammation was not diagnosed during this study, but would have been recorded if a generalized, densely cellular pattern of myocardial and epicardial infiltrates had been observed.

3) Neutrophilic Granulocyte infiltration was scored as follows: 0 Not remarkable granulocyte infiltrate, 1 Mild granulocyte infiltrate, 2 Moderate granulocyte infiltrate, 3 Severe granulocyte infiltrate;

4) Non-lymphocytic Mononuclear Cell infiltration was scored as follows: 0 Not remarkable histiocyte infiltrate, 1 Mild histiocyte infiltrate, 2 Moderate histiocyte infiltrate, 3 Severe histiocyte infiltrate;

5) Lymphocyte infiltration was scored as follows: 0 Not remarkable lymphocyte infiltrate, 1 Mild lymphocyte infiltrate, 2 Moderate lymphocyte infiltrate, 3 Severe lymphocyte infiltrate;

6) Fibrosis was scored as follows: 0 Not remarkable fibrosis, 1 Mild fibrosis, 2 Moderate fibrosis, 3 Severe fibrosis;

7) Myocyte Regeneration was characterized by the presence of streaming, pyramidal or stellate myocytes with enlarged single or multiple nuclei and slightly basophilic cytoplasm (FIG. 15D). Nuclei of affected cells frequently had clumped, marginated chromatin and prominent nucleoli, and mitotic figures were especially common at higher severity grades of regeneration. Myocyte regeneration, which in the majority of cases co-occurred spatially with myocyte necrosis, was generally most prominent at or near the junction of the stratum compactum and the stratum spongiosum. Myocyte regeneration was diagnosed in 89% of control fish, and only rarely in the other color groups. Diagnoses of myocyte regeneration ranged from Grade 1 to Grade 3, and Grade 3 regeneration. Grade 1 (mild) regeneration was exemplified by a single small cluster of affected myocytes in one or more hpf. A larger, patchy area of myocyte regeneration was recorded as Grade 2 (moderate), and when such areas became contiguous, the finding was recorded as Grade 3 (severe).

8) Eosinophilic Granulocyte infiltration was not included under the umbrella diagnosis of inflammation, but their presence was instead documented separately, because there did not appear to be any spatial or coincidental relationship between the occurrence of eosinophilic granulocytes and mononuclear cell inflammation. Eosinophilic granulocytic infiltrates were located almost exclusively at the bulboventricular junction, typically within the base of the bulbus arteriosus itself (FIG. 15E), at the bulboventricular interface, and/or within the walls of small arteries in that region. Eosinophilic granulocytes were characterized by obvious spherical or globular, red cytoplasmic granules. Occasional eosinophilic granulocytes had granules that were clumped, and less frequently, cells appeared to be in the process of degranulation. Diagnoses of eosinophilic granulocytic infiltrates ranged from Grade 1 to Grade 2. Grade 1 (mild) eosinophilic granulocytic infiltrates were observed as individual scattered cells or small foci of cells, whereas a Grade 2 (moderate) diagnosis was recorded when the infiltrates occupied a larger, patchy area. It should be noted that because eosinophilic granulocytes were observed primarily in histologic sections in which the base of the bulbus arteriosus was present in the section, the presence or absence of this structural element would tend to influence the groupwise incidence of eosinophilic granulocytic infiltrates.

A subset of the initial pathologist's findings were peer-reviewed (in blinded form) by a second pathologist. As in the initial evaluation, the peer review pathologist was blinded (i.e., unaware of the treatment group status of individual fish), although the reviewing pathologist had access to the original diagnoses made by the initial pathologist.

All analyses were performed using SAS/STAT® software (Version 9 of the SAS System for Windows, Copyright© 2002-2008 by SAS Institute Inc., Cary, N.C., USA). Frequencies of the ordinal histopathology scores were calculated for Eosinophilic Granulocyte, Fibrosis, Granulocyte, Inflammation, Lymphocyte, Myocyte Regeneration, Necrosis, and Non-Lymphocytic Mononuclear Cell for all treatment/batches. An index was constructed using ordinal scores from Eosinophilic Granulocyte, Fibrosis, Granulocyte, Inflammation, Lymphocyte, Myocyte Regeneration, Necrosis, and Non-Lymphocytic Mononuclear Cell data obtained from every fish within every treatment/batch. Weights for each variable were obtained using the scores from the control fish using the following formula:

$$Weight_y = \left(\frac{\bar{x}}{s_x}\right) * \left(\frac{\sum x}{T}\right),$$

where
x = the score of each variable, y, calculated separately, where
y = Eosinophilic Granulocyte infiltration, Fibrosis, Granulocyte infiltration, Inflammation, Lymphocyte infiltration, Myocyte Regeneration, Necrosis, and Non-Lymphocytic Mononuclear Cell infiltration,
$\bar{x}$ = mean of scores for each variable, y
$s_x$ = standard deviation of scores for each variable, y, and
T = is the grand sum of all scores.

The weights obtained were used as coefficients in an index to calculate a score for every fish and these scores were analyzed using analysis of variance techniques (ANOVA, SAS PROC MIXED) to determine if differences exist among treatment/batches. Descriptive statistics (mean, standard deviation, minimum, and maximum) are presented for the index score for all treatment/batches. All hypotheses were tested at a 2-sided 0.05 level of significance, unless otherwise stated. The results are of these studies are demonstrated in Tables 1-4:

TABLE 1

Frequency Distribution: Histological Scores

| Description | Severity Score | Treatment/Batch Frequency | | | |
|---|---|---|---|---|---|
| | | CONTROL/ J80421 (n = 99) | PD NAV/ 608148-00001 (n = 100) | PD NAV/ 608148-00002 (n = 100) | PD NAV/ 608148-00003 (n = 100) |
| Eosinophilic Granulocyte | Incidence: +/− | 49/50 | 35/65 | 51/49 | 52/48 |
| | 0[2] | 50 | 65 | 49 | 48 |
| | 1 | 39 | 28 | 43 | 47 |

TABLE 1-continued

Frequency Distribution: Histological Scores

| Description | Severity Score | Treatment/Batch Frequency | | | |
|---|---|---|---|---|---|
| | | CONTROL/ J80421 (n = 99) | PD NAV/ 608148-00001 (n = 100) | PD NAV/ 608148-00002 (n = 100) | PD NAV/ 608148-00003 (n = 100) |
| | 2 | 10 | 7 | 8 | 5 |
| | 3 | 0 | 0 | 0 | 0 |
| Fibrosis | Incidence: +/− | 0/99 | 1/99 | 0/100 | 0/100 |
| | 0 | 99 | 99 | 100 | 100 |
| | 1 | 0 | 1 | 0 | 0 |
| | 2 | 0 | 0 | 0 | 0 |
| | 3 | 0 | 0 | 0 | 0 |
| Granulocyte | Incidence: +/− | 0/99 | 1/99 | 2/98 | 1/99 |
| | 0 | 99 | 99 | 98 | 99 |
| | 1 | 0 | 1 | 2 | 1 |
| | 2 | 0 | 0 | 0 | 0 |
| | 3 | 0 | 0 | 0 | 0 |
| Inflammation | Incidence: +/− | 96/3 | 40/60 | 47/53 | 35/65 |
| | 0 | 3 | 60 | 53 | 65 |
| | 1 | 16 | 40 | 47 | 34 |
| | 2 | 80 | 0 | 0 | 1 |
| | 3 | 0 | 0 | 0 | 0 |
| Lymphocyte | Incidence: +/− | 96/3 | 39/61 | 48/52 | 35/65 |
| | 0 | 3 | 61 | 52 | 65 |
| | 1 | 17 | 39 | 48 | 34 |
| | 2 | 79 | 0 | 0 | 1 |
| | 3 | 0 | 0 | 0 | 0 |
| Myocyte Regeneration | Incidence: +/− | 88/11 | 1/99 | 1/99 | 2/98 |
| | 0 | 11 | 99 | 99 | 98 |
| | 1 | 47 | 1 | 1 | 1 |
| | 2 | 34 | 0 | 0 | 1 |
| | 3 | 7 | 0 | 0 | 0 |
| Necrosis | Incidence: +/− | 85/14 | 1/99 | 0/100 | 2/98 |
| | 0 | 14 | 99 | 100 | 98 |
| | 1 | 45 | 1 | 0 | 1 |
| | 2 | 22 | 0 | 0 | 0 |
| | 3 | 18 | 0 | 0 | 1 |
| Non-Lymphocytic Mononuclear Cell | Incidence: +/− | 96/3 | 40/60 | 48/52 | 35/65 |
| | 0 | 3 | 60 | 52 | 65 |
| | 1 | 17 | 40 | 48 | 34 |
| | 2 | 79 | 0 | 0 | 1 |
| | 3 | 0 | 0 | 0 | 0 |

1 − + = Scores of 1, 2, or 3 indicating severity of histopathological scoring positive; − = score of 0, indicating normal or not affected histological effect.
2 − Frequency of each of the graded score obtained from pathologist (see protocol for description of scoring regime).

TABLE 2

Summary Statistics for Histological Scores by Treatment/Batch

| Treatment/Batch | Histological Score | N | Mean | SD | Minimum | Maximum |
|---|---|---|---|---|---|---|
| CONTROL/J80421 | Eosinophilic Granulocyte | 99 | 0.60 | 0.67 | 0.00 | 2.00 |
| | Fibrosis | 99 | 0.00 | 0.00 | 0.00 | 0.00 |
| | Granulocyte | 99 | 0.00 | 0.00 | 0.00 | 0.00 |
| | Inflammation | 99 | 1.78 | 0.49 | 0.00 | 2.00 |
| | Lymphocyte | 99 | 1.77 | 0.49 | 0.00 | 2.00 |
| | Myocyte Regeneration | 99 | 1.37 | 0.78 | 0.00 | 3.00 |
| | Necrosis | 99 | 1.44 | 0.95 | 0.00 | 3.00 |
| | Non-Lymphocytic Mononuclear Cell | 99 | 1.77 | 0.49 | 0.00 | 2.00 |

TABLE 2-continued

Summary Statistics for Histological Scores by Treatment/Batch

| Treatment/Batch | Histological Score | N | Mean | SD | Minimum | Maximum |
|---|---|---|---|---|---|---|
| PD NAV/608148-00001 | Eosinophilic Granulocyte | 100 | 0.42 | 0.62 | 0.00 | 2.00 |
| | Fibrosis | 100 | 0.01 | 0.10 | 0.00 | 1.00 |
| | Granulocyte | 100 | 0.01 | 0.10 | 0.00 | 1.00 |
| | Inflammation | 100 | 0.40 | 0.49 | 0.00 | 1.00 |
| | Lymphocyte | 100 | 0.39 | 0.49 | 0.00 | 1.00 |
| | Myocyte Regeneration | 100 | 0.01 | 0.10 | 0.00 | 1.00 |
| | Necrosis | 100 | 0.01 | 0.10 | 0.00 | 1.00 |
| | Non-Lymphocytic Mononuclear Cell | 100 | 0.40 | 0.49 | 0.00 | 1.00 |
| PD NAV/608148-00002 | Eosinophilic Granulocyte | 100 | 0.59 | 0.64 | 0.00 | 2.00 |
| | Fibrosis | 100 | 0.00 | 0.00 | 0.00 | 0.00 |
| | Granulocyte | 100 | 0.02 | 0.14 | 0.00 | 1.00 |
| | Inflammation | 100 | 0.47 | 0.50 | 0.00 | 1.00 |
| | Lymphocyte | 100 | 0.48 | 0.50 | 0.00 | 1.00 |
| | Myocyte Regeneration | 100 | 0.01 | 0.10 | 0.00 | 1.00 |
| | Necrosis | 100 | 0.00 | 0.00 | 0.00 | 0.00 |
| | Non-Lymphocytic Mononuclear Cell | 100 | 0.48 | 0.50 | 0.00 | 1.00 |
| PD NAV/608148-00003 | Eosinophilic Granulocyte | 100 | 0.57 | 0.59 | 0.00 | 2.00 |
| | Fibrosis | 100 | 0.00 | 0.00 | 0.00 | 0.00 |
| | Granulocyte | 100 | 0.01 | 0.10 | 0.00 | 1.00 |
| | Inflammation | 100 | 0.36 | 0.50 | 0.00 | 2.00 |
| | Lymphocyte | 100 | 0.36 | 0.50 | 0.00 | 2.00 |
| | Myocyte Regeneration | 100 | 0.03 | 0.22 | 0.00 | 2.00 |
| | Necrosis | 100 | 0.04 | 0.32 | 0.00 | 3.00 |
| | Non-Lymphocytic Mononuclear Cell | 100 | 0.36 | 0.50 | 0.00 | 2.00 |

TABLE 3

Summary Statistics for the Index Score by Treatment/Batch

| Batch | N | Mean | SD | 95% Confidence Interval Lower Bound | 95% Confidence Interval Upper Bound | Minimum | Median | Maximum |
|---|---|---|---|---|---|---|---|---|
| CONTROL/J80421 | 99 | 4.397 | 1.372 | 4.123 | 4.671 | 0.000 | 4.520 | 6.786 |
| PO NAV/608148-00001 | 100 | 0.628 | 0.753 | 0.478 | 0.777 | 0.000 | 0.061 | 2.603 |
| PO NAV/608148-00002 | 100 | 0.746 | 0.758 | 0.596 | 0.897 | 0.000 | 0.122 | 2.481 |
| PO NAV/608148-00003 | 100 | 0.606 | 0.868 | 0.434 | 0.778 | 0.000 | 0.061 | 4.711 |

TABLE 4

LSMEAN Differences: Index Score Among Treatment/Breaches

| Batch | vs. Batch | LSMEAN[1] Difference | p-value |
|---|---|---|---|
| CONTROL/J80421 | PD NAV/608148-00001 | 3.769 | <.0001** |
| | PD NAV/608148-00002 | 3.651 | <.0001** |
| | PD NAV/608148-00003 | 3.791 | <.0001** |
| PD NAV/608148-00001 | PD NAV/608148-00002 | −0.118 | 0.3891 |
| | PD NAV/608148-00003 | 0.022 | 0.8718 |
| PD NAV/608148-00002 | PD NAV/608148-00003 | 0.140 | 0.3066 |

[1]-LSMEAN-Least squares mean
**Statistically significant at $p \leq 0.01$

A statistically significant difference in mean histological index score existed between the CONTROL/J80421 and all PD NAV batches (p<0.0001). No statistically significant differences existed in mean histological index scores among the PD NAV batches. Results of the analysis of the data from the PD-NAV efficacy trial indicate that statistically significant decreases in heart tissue abnormalities were observed in each of the vaccinated groups when compared to the control group of salmon. In addition, the trial showed no significant differences among the conformance batches, confirming consistency of vaccine production.

Example 3

Figure 17:
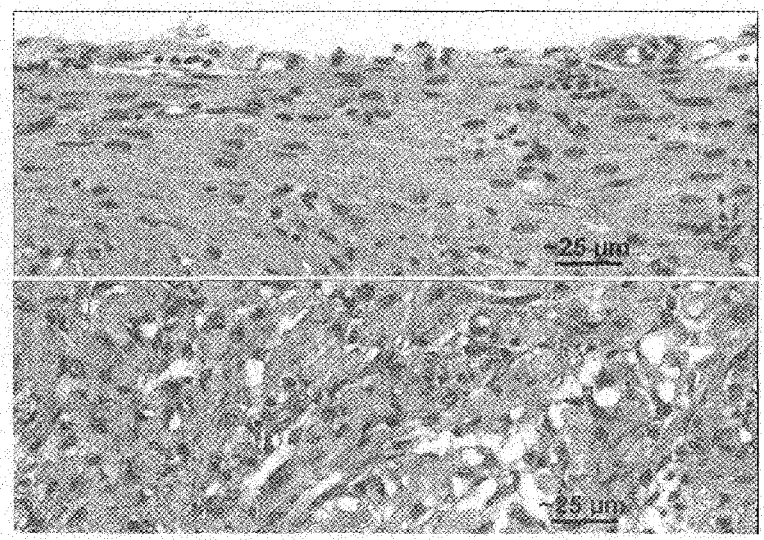

Another challenge study was also performed to further demonstrate vaccine efficacy using the heart histopathology index. The PD NAV vaccine described herein (pUK-SPDV-poly2#1 plasmid) was tested in 110 naïve Atlantic salmon assigned to each of three treatment groups (each receiving 0.05 ml intramuscular injection containing from 5 to 10 µg PD-NAV). 330 fish were maintained in a non-vaccinated control group. The different groups were tagged for identification purposes. The fish were of a bulk weight of 10-20 g (13 g average) and were maintained at 12±2° C. (400 dd immunization period). Challenge was carried out in a cohabitation model in FW (14±2° C.) in which 20% of the fish were injected intraperitoneally with SAV3 (e.g., acting as "Trojan" fish to infect others that were not injected with SAV3). Sampling (100 hearts of each group via histopathology (blinded)) was performed at 24 days post-challenge, a time known to exhibit significant damage to cardiac tissue. The heart histopathology index provides measures of up to eight parameters including Eosinophilic Granulocyte infiltration, Fibrosis, Granulocyte infiltration, Inflammation, Lymphocyte infiltration, Myocyte Regeneration, Necrosis, and Non-Lymphocytic Mononuclear Cell infiltration. Summaries of these results are shown in FIGS. 16-23. As shown therein, saline-vaccinated control fish (FIG. 16, group 1) exhibited significantly increased heart histopathology index measurements as compared to fish vaccinated with pUK-SPDV-poly2#1 plasmid (FIG. 16, groups 2-4, error bars indicate standard deviation of mean p<0.0001). Similarly, FIG. 17 provides images comparing non-necrotic (FIG. 17A) vs. necrotic tissues (FIG. 17B). FIGS. 18A and 18B illustrate the histopathology index and qPCR results, respectively, following SAV challenge in fish vaccinated with saline or pUK-SPDV-poly2#1 plasmid (at a 0.05, 0.1, 0.2, 0.5, 1.0 or 2.0 normalized dose). The data presented in FIGS. 18A and 18B show that the pUK-SPDV-poly2#1 plasmid both decreases the histopathology index and the amount of circulating SAV (the challenge virus).

Example 4

Figure 19:
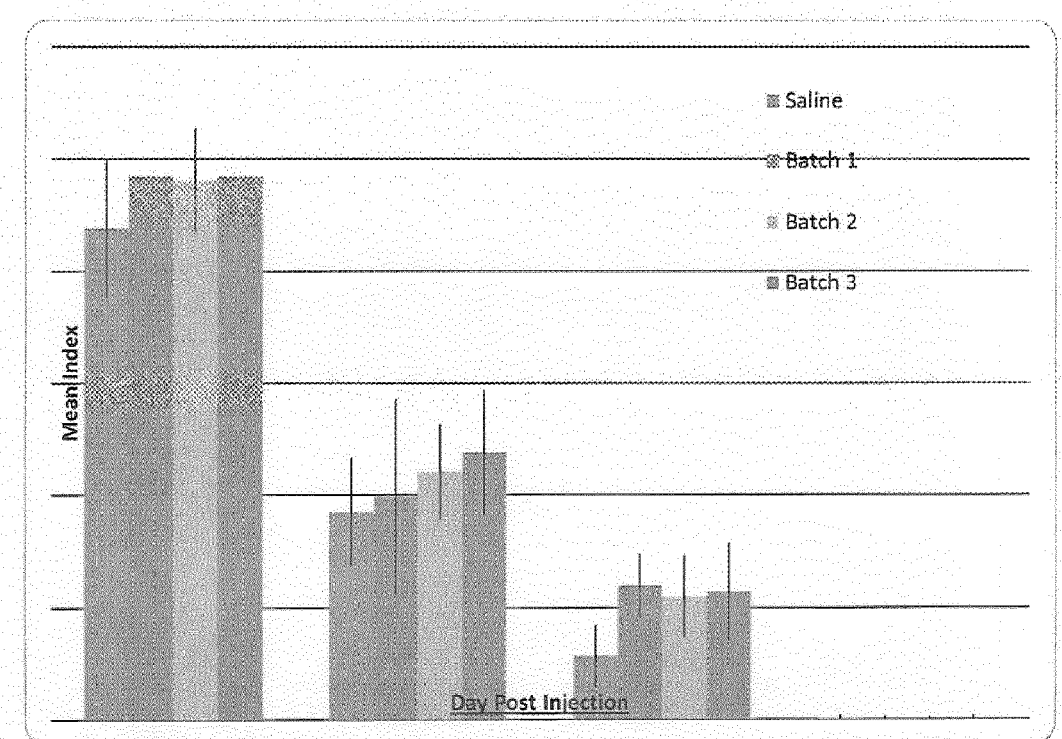

Another study was performed using 150 naïve Atlantic salmon assigned to each of three treatment groups (0.05 ml injection of a 10× concentrated pUK-SPDV-poly2#1 vaccine or saline) and observed over a 90-day period of time. The fish were of a bulk weight of 10-20 g (13 g average) and were maintained at 12±2° C. Ten to 20 samples were prepared at days 4, 8, 21 and 90 followed by macroscopic and microscopic examination of the injection site (muscle). An objective of this study was to demonstrate the safety of a 10× concentrated vaccine composition by measuring histopathology relative to saline control. As illustrated in FIG. 19, marginal increases in local reactions at the site of injection between Investigational Product and saline controls were observed on Days 4 and 21, which resolved entirely by Day 90. (FIG. 19: column in each group in order of presentation from left to right: saline, batch 1, batch 2, batch 3). Minor treatment-related local reactions were also observed at the site of injection but were transient in nature. It was also observed that 75% of pUK-SPDV-poly2#1 plasmid-vaccinated fish resumed feeding within one day after vaccination (100% returning to full feeding after 7 days). Histopathology image analysis indicated moderate inflammation (score 2) after administration of the 10× concentrated vaccine.

Example 5

Figure 20:
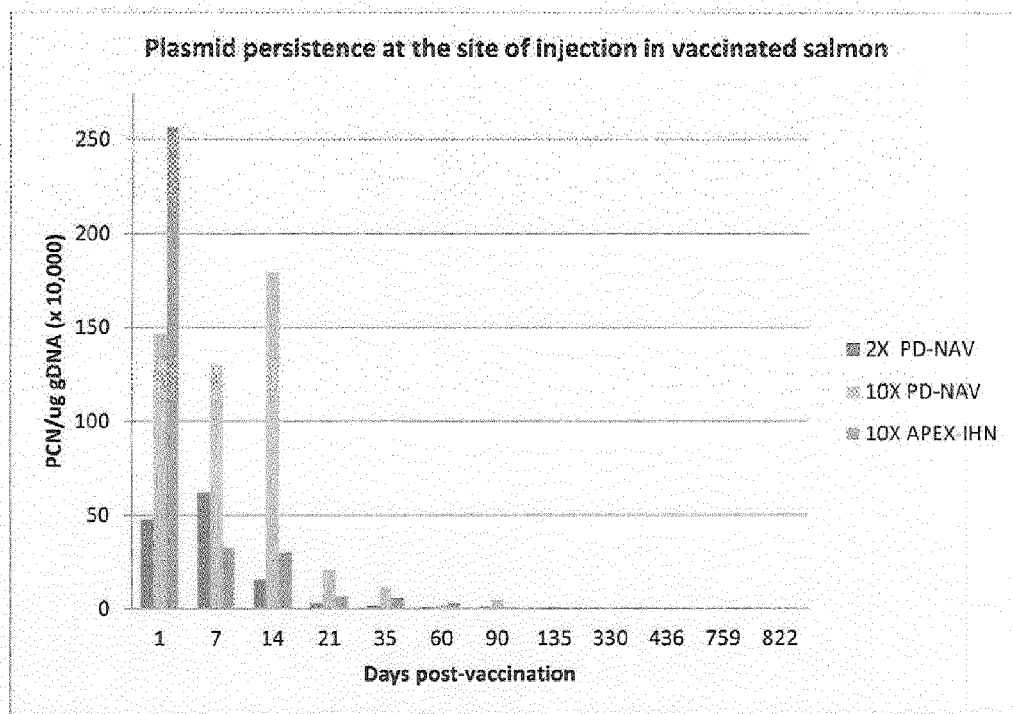

The pharmacokinetics of PD NAV was also studied. In this study, 200 naïve Atlantic salmon were assigned to one of three treatment groups (2× pUK-SPDV-poly2#1, 10× pUK-SPDV-poly2#1, or 10× APEX-IHN) and 200 to a saline-vaccinated control group (tagged appropriately). The bulk weight of these fish was 9.0±1.4 g and these were held in fresh water at 10-12° C. Fish were vaccinated by a 0.05 ml intramuscular injection. Twelve samples were taken at various time points (ten fish/sample) over a 27-month period. Various organs and muscle at the injection site were analyzed for plasmid using qPCR. As shown in FIG. 20, plasmid was rapidly cleared from the injection site (e.g., within 21 days the level of plasmid at the injection site (2× concentrated vaccine)) dropped to below 10% of the original amount). Plasmid was detectable at least until day 759 (<0.11% of original levels).

Example 6

Figure 21:
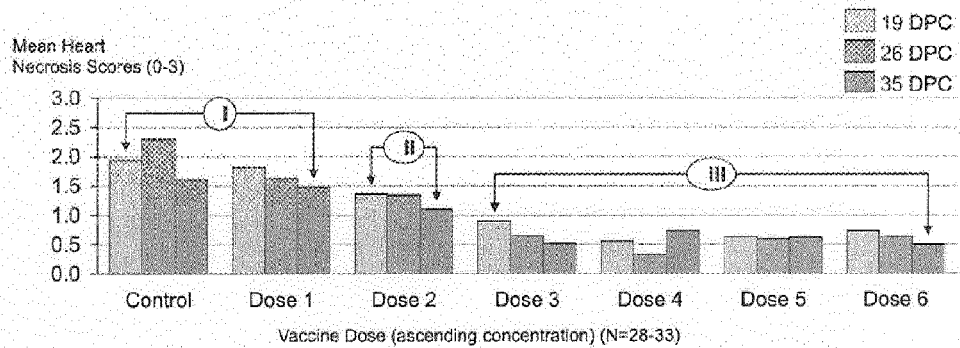
Figure 22:
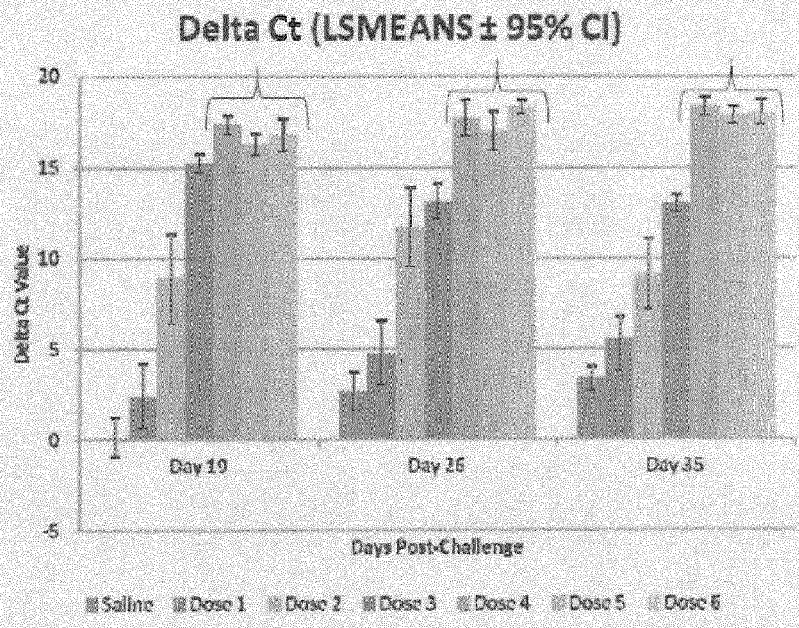
Figure 23:
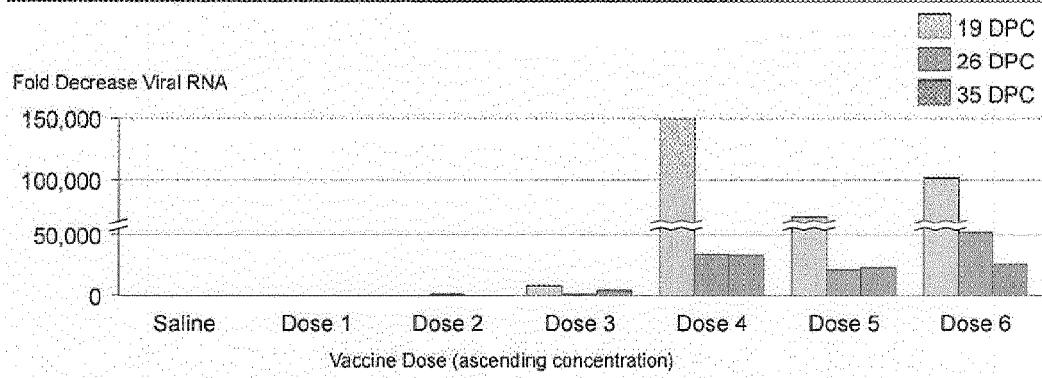

Studies were also conducted to determine optimal dose concentration of pUK-SPDV-poly2#1 with respect to necrosis (e.g., measured by the heart histopathology index of heart apex in 10% buffered formalin; analyzed by the GLIMMIX procedure (SAS/STAT® software)) and the amount of virus present in heart tissue (e.g., measured by RT-qPCR of RNA of heart apex (target gene=nsP1 (96.22% efficiency), reference gene=EF1-alpha (95.52% efficiency); analyzed by two-way ANOVA (0.05 significance level), SAS/STAT® software). Samples were procured from the fish for testing at 19, 26 and 35 days post-challenge with SAV-3 (DPC). Dosing groups (compared to saline control) were 0.5 µg/dose (Dose 1), 1 µg/dose (Dose 2), 2 µg/dose (Dose 3), 5 µg/dose (Dose 4), 10 µg/dose (Dose 5), and 20 µg/dose (Dose 6). As shown in FIGS. 21-23, the highest doses resulted in the lowest mean heart necrosis scores (FIG. 21) and the lowest concentration of SAV3 RNA detected in samples (FIGS. 22, 23), respectively. For instance, FIG. 23C shows that Dose 4 had the highest fold decrease at both 19 DPC (>149000) and 35 DPC (>32000) sampling time point while Dose 6 exceeded a 51000 fold reduction at 26 DPC, and Dose 5 was the third most effective treatment for all three sampling days. Additional data is presented in Tables 5-23:

TABLE 5

Frequency Distribution of Histological Scores for Day 19

| | | Treatment Frequency | | | | | | |
|---|---|---|---|---|---|---|---|---|
| | | | pUK-SPDV-poly2#1 | | | | | |
| Description | Severity Score[1] | Saline (Control) (n = 20) | 0.5 ug/dose (n = 20) | 1 ug/dose (n = 20) | 2 ug/dose (n = 20) | 5 ug/dose (n = 20) | 10 ug/dose (n = 20) | 20 ug/dose (n = 20) |
| Fibrosis | Incidence: +/− | 0/20 | 0/20 | 0/20 | 0/20 | 0/20 | 0/20 | 0/20 |
| | 0[2] | 20 | 20 | 20 | 20 | 20 | 20 | 20 |
| | 1 | 0 | 0 | 0 | 0 | 0 | 0 | 0 |
| | 2 | 0 | 0 | 0 | 0 | 0 | 0 | 0 |
| | 3 | 0 | 0 | 0 | 0 | 0 | 0 | 0 |
| Granulocyte | Incidence: +/− | 5/15 | 4/16 | 4/16 | 5/15 | 1/19 | 2/18 | 0/20 |
| | 0 | 15 | 16 | 16 | 15 | 19 | 18 | 20 |
| | 1 | 5 | 3 | 4 | 5 | 1 | 2 | 0 |
| | 2 | 0 | 1 | 0 | 0 | 0 | 0 | 0 |
| | 3 | 0 | 0 | 0 | 0 | 0 | 0 | 0 |

TABLE 5-continued

Frequency Distribution of Histological Scores for Day 19

| | | Treatment Frequency | | | | | | |
|---|---|---|---|---|---|---|---|---|
| | | | pUK-SPDV-poly2#1 | | | | | |
| Description | Severity Score[1] | Saline (Control) (n = 20) | 0.5 ug/ dose (n = 20) | 1 ug/ dose (n = 20) | 2 ug/ dose (n = 20) | 5 ug/ dose (n = 20) | 10 ug/ dose (n = 20) | 20 ug/ dose (n = 20) |
| Histiocyte | Incidence: +/− | 4/16 | 6/14 | 5/15 | 2/18 | 1/19 | 1/19 | 1/19 |
| | 0 | 16 | 14 | 15 | 18 | 19 | 19 | 19 |
| | 1 | 4 | 6 | 4 | 2 | 1 | 1 | 1 |
| | 2 | 0 | 0 | 1 | 0 | 0 | 0 | 0 |
| | 3 | 0 | 0 | 0 | 0 | 0 | 0 | 0 |
| Inflammation | Incidence: +/− | 18/2 | 16/4 | 14/6 | 13/7 | 13/7 | 12/8 | 14/6 |
| | 0 | 2 | 4 | 6 | 7 | 7 | 8 | 6 |
| | 1 | 16 | 13 | 11 | 12 | 12 | 11 | 12 |
| | 2 | 2 | 3 | 3 | 1 | 1 | 1 | 2 |
| | 3 | 0 | 0 | 0 | 0 | 0 | 0 | 0 |
| Lymphocyte | Incidence: +/− | 15/5 | 14/6 | 12/8 | 11/9 | 12/8 | 12/8 | 14/6 |
| | 0 | 5 | 6 | 8 | 9 | 8 | 8 | 6 |
| | 1 | 13 | 13 | 12 | 11 | 10 | 10 | 11 |
| | 2 | 2 | 1 | 0 | 0 | 2 | 2 | 3 |
| | 3 | 0 | 0 | 0 | 0 | 0 | 0 | 0 |
| Necrosis | Incidence: +/− | 18/2 | 16/4 | 14/6 | 12/8 | 9/11 | 8/12 | 8/12 |
| | 0 | 2 | 4 | 6 | 8 | 11 | 12 | 12 |
| | 1 | 4 | 0 | 5 | 8 | 9 | 5 | 6 |
| | 2 | 9 | 5 | 3 | 2 | 0 | 3 | 2 |
| | 3 | 5 | 11 | 6 | 2 | 0 | 0 | 0 |

[1] + = Scores of 1, 2, or 3 indicating severity of histopathological scoring positive; − = score of 0, indicating normal or not affected histological effect.
[2]Frequency of each of the graded score obtained from pathologist (see protocol for description of scoring regime).

TABLE 6

| Frequency Distribution of Histological Scores for Day 26 | | | | | | | | |
|---|---|---|---|---|---|---|---|---|
| | | Treatment Frequency | | | | | | |
| | | | pUK-SPDV-poly2#1 | | | | | |
| Description | Severity Score[1] | Saline (Control) (n = 20) | 0.5 ug/ dose (n = 20) | 1 ug/ dose (n = 20) | 2 ug/ dose (n = 20) | 5 ug/ dose (n = 20) | 10 ug/ dose (n = 20) | 20 ug/ dose (n = 20) |
| Fibrosis | Incidence: +/− | 4/16 | 2/18 | 0/20 | 1/19 | 0/20 | 0/20 | 0/20 |
| | 0[2] | 16 | 18 | 20 | 19 | 20 | 20 | 20 |
| | 1 | 4 | 2 | 0 | 1 | 0 | 0 | 0 |
| | 2 | 0 | 0 | 0 | 0 | 0 | 0 | 0 |
| | 3 | 0 | 0 | 0 | 0 | 0 | 0 | 0 |
| Granulocyte | Incidence: +/− | 3/17 | 4/16 | 3/17 | 0/20 | 1/19 | 1/19 | 1/19 |
| | 0 | 17 | 16 | 17 | 20 | 19 | 19 | 19 |
| | 1 | 3 | 4 | 3 | 0 | 1 | 1 | 1 |
| | 2 | 0 | 0 | 0 | 0 | 0 | 0 | 0 |
| | 3 | 0 | 0 | 0 | 0 | 0 | 0 | 0 |
| Histiocyte | Incidence: +/− | 5/15 | 7/13 | 9/11 | 6/14 | 5/15 | 7/13 | 2/18 |
| | 0 | 5 | 7 | 11 | 14 | 15 | 13 | 18 |
| | 1 | 12 | 11 | 8 | 5 | 5 | 7 | 2 |
| | 2 | 3 | 2 | 1 | 1 | 0 | 0 | 0 |
| | 3 | 0 | 0 | 0 | 0 | 0 | 0 | 0 |
| Inflammation | Incidence: +/− | 19/1 | 18/2 | 17/3 | 17/3 | 15/5 | 14/6 | 11/9 |
| | 0 | 1 | 2 | 3 | 3 | 5 | 6 | 9 |
| | 1 | 12 | 13 | 16 | 15 | 14 | 14 | 10 |
| | 2 | 7 | 4 | 1 | 2 | 1 | 0 | 1 |
| | 3 | 0 | 1 | 0 | 0 | 0 | 0 | 0 |
| Lymphocyte | Incidence: +/− | 15/5 | 14/6 | 12/8 | 11/9 | 12/8 | 12/8 | 14/6 |
| | 0 | 5 | 6 | 8 | 9 | 8 | 8 | 6 |
| | 1 | 13 | 13 | 12 | 11 | 10 | 10 | 11 |

TABLE 6-continued Frequency Distribution of Histological Scores for Day 26

| Description | Severity Score[1] | Treatment Frequency Saline (Control) (n = 20) | pUK-SPDV-poly2#1 0.5 ug/dose (n = 20) | 1 ug/dose (n = 20) | 2 ug/dose (n = 20) | 5 ug/dose (n = 20) | 10 ug/dose (n = 20) | 20 ug/dose (n = 20) |
|---|---|---|---|---|---|---|---|---|
| | 2 | 2 | 1 | 0 | 0 | 2 | 2 | 3 |
| | 3 | 0 | 0 | 0 | 0 | 0 | 0 | 0 |
| Necrosis | Incidence: +/− | 20/0 | 16/4 | 14/6 | 6/14 | 6/14 | 7/13 | 11/9 |
| | 0 | 0 | 4 | 6 | 14 | 14 | 13 | 9 |
| | 1 | 0 | 6 | 3 | 3 | 4 | 2 | 7 |
| | 2 | 6 | 0 | 7 | 3 | 2 | 5 | 4 |
| | 3 | 14 | 10 | 4 | 0 | 0 | 0 | 0 |

[1]+ = Scores of 1, 2, or 3 indicating severity of histopathological scoring positive; − = score of 0, indicating normal or not affected histological effect.

[2]Frequency of each of the graded score obtained from pathologist (see protocol for description of scoring regime).

TABLE 7

Frequency Distribution of Histological Scores for Day 35

| Description | Severity Score[1] | Treatment Frequency Saline (Control) (n = 20) | pUK-SPDV-poly2#1 0.5 ug/dose (n = 20) | 1 ug/dose (n = 20) | 2 ug/dose (n = 20) | 5 ug/dose (n = 20) | 10 ug/dose (n = 20) | 20 ug/dose (n = 20) |
|---|---|---|---|---|---|---|---|---|
| Fibrosis | Incidence: +/− | 3/17 | 2/18 | 0/20 | 0/20 | 0/20 | 0/20 | 0/20 |
| | 0[2] | 17 | 18 | 20 | 20 | 20 | 20 | 20 |
| | 1 | 3 | 2 | 0 | 0 | 0 | 0 | 0 |
| | 2 | 0 | 0 | 0 | 0 | 0 | 0 | 0 |
| | 3 | 0 | 0 | 0 | 0 | 0 | 0 | 0 |
| Granulocyte | Incidence: +/− | 3/17 | 2/18 | 2/18 | 0/20 | 0/20 | 0/20 | 0/20 |
| | 0 | 17 | 18 | 18 | 20 | 20 | 20 | 20 |
| | 1 | 2 | 1 | 2 | 0 | 0 | 0 | 0 |
| | 2 | 1 | 1 | 0 | 0 | 0 | 0 | 0 |
| | 3 | 0 | 0 | 0 | 0 | 0 | 0 | 0 |
| Histiocyte | Incidence: +/− | 12/8 | 15/5 | 9/11 | 6/14 | 8/12 | 7/13 | 3/17 |
| | 0 | 8 | 5 | 11 | 14 | 12 | 13 | 17 |
| | 1 | 8 | 11 | 9 | 5 | 8 | 6 | 3 |
| | 2 | 4 | 3 | 0 | 1 | 0 | 1 | 0 |
| | 3 | 0 | 1 | 0 | 0 | 0 | 0 | 0 |
| Inflammation | Incidence: +/− | 19/1 | 18/2 | 13/7 | 12/8 | 14/6 | 12/8 | 14/6 |
| | 0 | 1 | 2 | 7 | 8 | 6 | 8 | 6 |
| | 1 | 12 | 12 | 12 | 8 | 12 | 10 | 13 |
| | 2 | 6 | 5 | 1 | 4 | 2 | 2 | 1 |
| | 3 | 1 | 1 | 0 | 0 | 0 | 0 | 0 |
| Lymphocyte | Incidence: +/− | 16/4 | 11/9 | 12/8 | 12/8 | 12/8 | 11/9 | 13/7 |
| | 0 | 4 | 9 | 8 | 8 | 12 | 9 | 7 |
| | 1 | 12 | 8 | 11 | 9 | 6 | 9 | 12 |
| | 2 | 4 | 3 | 1 | 3 | 2 | 2 | 1 |
| | 3 | 0 | 0 | 0 | 0 | 0 | 0 | 0 |
| Necrosis | Incidence: +/− | 13/7 | 16/4 | 10/10 | 7/13 | 9/11 | 10/10 | 10/10 |
| | 0 | 7 | 4 | 10 | 13 | 9 | 10 | 10 |
| | 1 | 2 | 3 | 2 | 5 | 6 | 8 | 7 |
| | 2 | 5 | 10 | 5 | 2 | 5 | 2 | 3 |
| | 3 | 6 | 3 | 3 | 0 | 0 | 0 | 0 |

[1]+ = Scores of 1, 2, or 3 indicating severity of histopathological scoring positive; − = score of 0, indicating normal or not affected histological effect.

[2]Frequency of each of the graded score obtained from pathologist (see protocol for description of scoring regime).

TABLE 8

Summary Statistics for Histological Scores by Treatment within Day 19

| Treatment | Variable | N | Mean | SD | Minimum | Maximum |
|---|---|---|---|---|---|---|
| Saline (Control) | Fibrosis | 20 | 0.00 | 0.00 | 0.00 | 0.00 |
| | Granulocytes | 20 | 0.25 | 0.44 | 0.00 | 1.00 |
| | Histiocytes | 20 | 0.20 | 0.41 | 0.00 | 1.00 |
| | Inflammation | 20 | 1.00 | 0.46 | 0.00 | 2.00 |
| | Lymphocytes | 20 | 0.85 | 0.59 | 0.00 | 2.00 |
| | Necrosis | 20 | 1.85 | 0.93 | 0.00 | 3.00 |
| pUK-SPDV-poly2#1 (0.5 ug/dose) | Fibrosis | 20 | 0.00 | 0.00 | 0.00 | 0.00 |
| | Granulocytes | 20 | 0.25 | 0.55 | 0.00 | 2.00 |
| | Histiocytes | 20 | 0.30 | 0.47 | 0.00 | 1.00 |
| | Inflammation | 20 | 0.95 | 0.60 | 0.00 | 2.00 |
| | Lymphocytes | 20 | 0.75 | 0.55 | 0.00 | 2.00 |
| | Necrosis | 20 | 2.15 | 1.18 | 0.00 | 3.00 |
| pUK-SPDV-poly2#1 (1 ug/dose) | Fibrosis | 20 | 0.00 | 0.00 | 0.00 | 0.00 |
| | Granulocytes | 20 | 0.20 | 0.41 | 0.00 | 1.00 |
| | Histiocytes | 20 | 0.30 | 0.57 | 0.00 | 2.00 |
| | Inflammation | 20 | 0.85 | 0.67 | 0.00 | 2.00 |
| | Lymphocytes | 20 | 0.60 | 0.50 | 0.00 | 1.00 |
| | Necrosis | 20 | 1.45 | 1.23 | 0.00 | 3.00 |
| pUK-SPDV-poly2#1 (2 ug/dose) | Fibrosis | 20 | 0.00 | 0.00 | 0.00 | 0.00 |
| | Granulocytes | 20 | 0.25 | 0.44 | 0.00 | 1.00 |
| | Histiocytes | 20 | 0.10 | 0.31 | 0.00 | 1.00 |
| | Inflammation | 20 | 0.70 | 0.57 | 0.00 | 2.00 |
| | Lymphocytes | 20 | 0.55 | 0.51 | 0.00 | 1.00 |
| | Necrosis | 20 | 0.90 | 0.97 | 0.00 | 3.00 |
| pUK-SPDV-poly2#1 (5 ug/dose) | Fibrosis | 20 | 0.00 | 0.00 | 0.00 | 0.00 |
| | Granulocytes | 20 | 0.05 | 0.22 | 0.00 | 1.00 |
| | Histiocytes | 20 | 0.05 | 0.22 | 0.00 | 1.00 |
| | Inflammation | 20 | 0.70 | 0.57 | 0.00 | 2.00 |
| | Lymphocytes | 20 | 0.70 | 0.66 | 0.00 | 2.00 |
| | Necrosis | 20 | 0.45 | 0.51 | 0.00 | 1.00 |
| pUK-SPDV-poly2#1 (10 ug/dose) | Fibrosis | 20 | 0.00 | 0.00 | 0.00 | 0.00 |
| | Granulocytes | 20 | 0.10 | 0.31 | 0.00 | 1.00 |
| | Histiocytes | 20 | 0.05 | 0.22 | 0.00 | 1.00 |
| | Inflammation | 20 | 0.65 | 0.59 | 0.00 | 2.00 |
| | Lymphocytes | 20 | 0.70 | 0.66 | 0.00 | 2.00 |
| | Necrosis | 20 | 0.55 | 0.76 | 0.00 | 2.00 |
| pUK-SPDV-poly2#1 (20 ug/dose) | Fibrosis | 20 | 0.00 | 0.00 | 0.00 | 0.00 |
| | Granulocytes | 20 | 0.00 | 0.00 | 0.00 | 0.00 |
| | Histiocytes | 20 | 0.05 | 0.22 | 0.00 | 1.00 |
| | Inflammation | 20 | 0.80 | 0.62 | 0.00 | 2.00 |
| | Lymphocytes | 20 | 0.85 | 0.67 | 0.00 | 2.00 |
| | Necrosis | 20 | 0.50 | 0.69 | 0.00 | 2.00 |

TABLE 9

Summary Statistics for Histological Scores by Treatment within Day 26

| Treatment | Variable | N | Mean | SD | Minimum | Maximum |
|---|---|---|---|---|---|---|
| Saline (Control) | Fibrosis | 20 | 0.20 | 0.41 | 0.00 | 1.00 |
| | Granulocytes | 20 | 0.15 | 0.37 | 0.00 | 1.00 |
| | Histiocytes | 20 | 0.90 | 0.64 | 0.00 | 2.00 |
| | Inflammation | 20 | 1.30 | 0.57 | 0.00 | 2.00 |
| | Lymphocytes | 20 | 1.10 | 0.55 | 0.00 | 2.00 |
| | Necrosis | 20 | 2.70 | 0.47 | 2.00 | 3.00 |
| pUK-SPDV-poly2#1 (0.5 ug/dose) | Fibrosis | 20 | 0.10 | 0.31 | 0.00 | 1.00 |
| | Granulocytes | 20 | 0.20 | 0.41 | 0.00 | 1.00 |
| | Histiocytes | 20 | 0.75 | 0.64 | 0.00 | 2.00 |
| | Inflammation | 20 | 1.20 | 0.70 | 0.00 | 3.00 |
| | Lymphocytes | 20 | 0.90 | 0.72 | 0.00 | 2.00 |
| | Necrosis | 20 | 1.80 | 1.28 | 0.00 | 3.00 |
| pUK-SPDV-poly2#1 (1 ug/dose) | Fibrosis | 20 | 0.00 | 0.00 | 0.00 | 0.00 |
| | Granulocytes | 20 | 0.15 | 0.37 | 0.00 | 1.00 |
| | Histiocytes | 20 | 0.50 | 0.61 | 0.00 | 2.00 |
| | Inflammation | 20 | 0.90 | 0.45 | 0.00 | 2.00 |
| | Lymphocytes | 20 | 0.55 | 0.60 | 0.00 | 2.00 |
| | Necrosis | 20 | 1.45 | 1.15 | 0.00 | 3.00 |
| pUK-SPDV-poly2#1 (2 ug/dose) | Fibrosis | 20 | 0.05 | 0.22 | 0.00 | 1.00 |
| | Granulocytes | 20 | 0.00 | 0.00 | 0.00 | 0.00 |
| | Histiocytes | 20 | 0.35 | 0.59 | 0.00 | 2.00 |
| | Inflammation | 20 | 0.95 | 0.51 | 0.00 | 2.00 |
| | Lymphocytes | 20 | 0.90 | 0.45 | 0.00 | 2.00 |
| | Necrosis | 20 | 0.45 | 0.76 | 0.00 | 2.00 |

TABLE 9-continued

| Summary Statistics for Histological Scores by Treatment within Day 26 | | | | | | |
|---|---|---|---|---|---|---|
| Treatment | Variable | N | Mean | SD | Minimum | Maximum |
| pUK-SPDV-poly2#1 (5 ug/dose) | Fibrosis | 20 | 0.00 | 0.00 | 0.00 | 0.00 |
| | Granulocytes | 20 | 0.05 | 0.22 | 0.00 | 1.00 |
| | Histiocytes | 20 | 0.25 | 0.44 | 0.00 | 1.00 |
| | Inflammation | 20 | 0.80 | 0.52 | 0.00 | 2.00 |
| | Lymphocytes | 20 | 0.80 | 0.52 | 0.00 | 2.00 |
| | Necrosis | 20 | 0.40 | 0.68 | 0.00 | 2.00 |
| pUK-SPDV-poly2#1 (10 ug/dose) | Fibrosis | 20 | 0.00 | 0.00 | 0.00 | 0.00 |
| | Granulocytes | 20 | 0.05 | 0.22 | 0.00 | 1.00 |
| | Histiocytes | 20 | 0.35 | 0.49 | 0.00 | 1.00 |
| | Inflammation | 20 | 0.70 | 0.47 | 0.00 | 1.00 |
| | Lymphocytes | 20 | 0.60 | 0.50 | 0.00 | 1.00 |
| | Necrosis | 20 | 0.60 | 0.88 | 0.00 | 2.00 |
| pUK-SPDV-poly2#1 (20 ug/dose) | Fibrosis | 20 | 0.00 | 0.00 | 0.00 | 0.00 |
| | Granulocytes | 20 | 0.05 | 0.22 | 0.00 | 1.00 |
| | Histiocytes | 20 | 0.10 | 0.31 | 0.00 | 1.00 |
| | Inflammation | 20 | 0.60 | 0.60 | 0.00 | 2.00 |
| | Lymphocytes | 20 | 0.50 | 0.61 | 0.00 | 2.00 |
| | Necrosis | 20 | 0.75 | 0.79 | 0.00 | 2.00 |

TABLE 10

| Summary Statistics for Histological Scores by Treatment within Day 35 | | | | | | |
|---|---|---|---|---|---|---|
| Treatment | Variable | N | Mean | SD | Minimum | Maximum |
| Saline (Control) | Fibrosis | 20 | 0.15 | 0.37 | 0.00 | 1.00 |
| | Granulocytes | 20 | 0.20 | 0.52 | 0.00 | 2.00 |
| | Histiocytes | 20 | 0.80 | 0.77 | 0.00 | 2.00 |
| | Inflammation | 20 | 1.35 | 0.67 | 0.00 | 3.00 |
| | Lymphocytes | 20 | 1.00 | 0.65 | 0.00 | 2.00 |
| | Necrosis | 20 | 1.50 | 1.28 | 0.00 | 3.00 |
| pUK-SPDV-poly2#1 (0.5 ug/dose) | Fibrosis | 20 | 0.10 | 0.31 | 0.00 | 1.00 |
| | Granulocytes | 20 | 0.15 | 0.49 | 0.00 | 2.00 |
| | Histiocytes | 20 | 1.00 | 0.79 | 0.00 | 3.00 |
| | Inflammation | 20 | 1.25 | 0.72 | 0.00 | 3.00 |
| | Lymphocytes | 20 | 0.70 | 0.73 | 0.00 | 2.00 |
| | Necrosis | 20 | 1.60 | 0.99 | 0.00 | 3.00 |
| pUK-SPDV-poly2#1 (1 ug/dose) | Fibrosis | 20 | 0.00 | 0.00 | 0.00 | 0.00 |
| | Granulocytes | 20 | 0.10 | 0.31 | 0.00 | 1.00 |
| | Histiocytes | 20 | 0.45 | 0.51 | 0.00 | 1.00 |
| | Inflammation | 20 | 0.70 | 0.57 | 0.00 | 2.00 |
| | Lymphocytes | 20 | 0.65 | 0.59 | 0.00 | 2.00 |
| | Necrosis | 20 | 1.05 | 1.19 | 0.00 | 3.00 |
| pUK-SPDV-poly2#1 (2 ug/dose) | Fibrosis | 20 | 0.00 | 0.00 | 0.00 | 0.00 |
| | Granulocytes | 20 | 0.00 | 0.00 | 0.00 | 0.00 |
| | Histiocytes | 20 | 0.35 | 0.59 | 0.00 | 2.00 |
| | Inflammation | 20 | 0.80 | 0.77 | 0.00 | 2.00 |
| | Lymphocytes | 20 | 0.75 | 0.72 | 0.00 | 2.00 |
| | Necrosis | 20 | 0.45 | 0.69 | 0.00 | 2.00 |
| pUK-SPDV-poly2#1 (5 ug/dose) | Fibrosis | 20 | 0.00 | 0.00 | 0.00 | 0.00 |
| | Granulocytes | 20 | 0.00 | 0.00 | 0.00 | 0.00 |
| | Histiocytes | 20 | 0.40 | 0.50 | 0.00 | 1.00 |
| | Inflammation | 20 | 0.80 | 0.62 | 0.00 | 2.00 |
| | Lymphocytes | 20 | 0.50 | 0.69 | 0.00 | 2.00 |
| | Necrosis | 20 | 0.80 | 0.83 | 0.00 | 2.00 |
| pUK-SPDV-poly2#1 (10 ug/dose) | Fibrosis | 20 | 0.00 | 0.00 | 0.00 | 0.00 |
| | Granulocytes | 20 | 0.00 | 0.00 | 0.00 | 0.00 |
| | Histiocytes | 20 | 0.40 | 0.60 | 0.00 | 2.00 |
| | Inflammation | 20 | 0.70 | 0.66 | 0.00 | 2.00 |
| | Lymphocytes | 20 | 0.65 | 0.67 | 0.00 | 2.00 |
| | Necrosis | 20 | 0.60 | 0.68 | 0.00 | 2.00 |
| pUK-SPDV-poly2#1 (20 ug/dose) | Fibrosis | 20 | 0.00 | 0.00 | 0.00 | 0.00 |
| | Granulocytes | 20 | 0.00 | 0.00 | 0.00 | 0.00 |
| | Histiocytes | 20 | 0.15 | 0.37 | 0.00 | 1.00 |
| | Inflammation | 20 | 0.75 | 0.55 | 0.00 | 2.00 |
| | Lymphocytes | 20 | 0.70 | 0.57 | 0.00 | 2.00 |
| | Necrosis | 20 | 0.65 | 0.75 | 0.00 | 2.00 |

TABLE 11

Summary Statistics for the Index Score by Treatment from Day 19 Histological Results

| Treatment | N | Mean | SD | 95% Confidence Interval Lower Bound | 95% Confidence Interval Upper Bound | Minimum | Median | Maximum |
|---|---|---|---|---|---|---|---|---|
| Saline (Control) | 20 | 2.425 | 0.792 | 2.054 | 2.796 | 0.822 | 2.589 | 4.055 |
| pUK-SPDV-poly2#1 (0.5 ug/dose) | 20 | 2.637 | 1.363 | 1.999 | 3.275 | 0.000 | 2.925 | 4.328 |
| pUK-SPDV-poly2#1 (1 ug/dose) | 20 | 1.919 | 1.346 | 1.290 | 2.549 | 0.000 | 1.705 | 4.055 |
| pUK-SPDV-poly2#1 (2 ug/dose) | 20 | 1.337 | 1.123 | 0.811 | 1.862 | 0.000 | 0.884 | 4.032 |
| pUK-SPDV-poly2#1 (5 ug/dose) | 20 | 0.976 | 0.581 | 0.704 | 1.248 | 0.000 | 0.853 | 2.002 |
| pUK-SPDV-poly2#1 (10 ug/dose) | 20 | 1.039 | 0.820 | 0.656 | 1.423 | 0.000 | 0.839 | 2.612 |
| pUK-SPDV-poly2#1 (20 ug/dose) | 20 | 1.115 | 0.684 | 0.795 | 1.435 | 0.000 | 0.884 | 2.589 |

TABLE 12

Summary Statistics for the Index Score by Treatment from Day 26 Histological Results

| Treatment | N | Mean | SD | 95% Confidence Interval Lower Bound | 95% Confidence Interval Upper Bound | Minimum | Median | Maximum |
|---|---|---|---|---|---|---|---|---|
| Saline (Control) | 20 | 7.762 | 1.341 | 7.134 | 8.389 | 5.694 | 8.335 | 9.161 |
| pUK-SPDV-poly2#1 (0.5 ug/dose) | 20 | 5.417 | 3.497 | 3.781 | 7.054 | 0.000 | 5.721 | 9.836 |
| pUK-SPDV-poly2#1 (1 ug/dose) | 20 | 4.251 | 2.867 | 2.809 | 5.592 | 0.000 | 4.884 | 9.000 |
| pUK-SPDV-poly2#1 (2 ug/dose) | 20 | 1.922 | 1.936 | 1.016 | 2.829 | 0.000 | 1.010 | 5.893 |
| pUK-SPDV-poly2#1 (5 ug/dose) | 20 | 1.676 | 1.758 | 0.853 | 2.498 | 0.000 | 1.010 | 5.893 |
| pUK-SPDV-poly2#1 (10 ug/dose) | 20 | 2.068 | 2.321 | 0.982 | 3.154 | 0.000 | 0.910 | 5.903 |
| pUK-SPDV-poly2#1 (20 ug/dose) | 20 | 2.304 | 1.808 | 1.457 | 3.150 | 0.000 | 2.442 | 5.549 |

TABLE 13

Summary Statistics for the Index Score by Treatment from Day 35 Histological Results

| Treatment | N | Mean | SD | 95% Confidence Interval Lower Bound | 95% Confidence Interval Upper Bound | Minimum | Median | Maximum |
|---|---|---|---|---|---|---|---|---|
| Saline (Control) | 20 | 1.708 | 0.743 | 1.361 | 2.056 | 0.710 | 1.630 | 3.109 |
| pUK-SPDV-poly2#1 (0.5 ug/dose) | 20 | 1.629 | 0.876 | 1.219 | 2.039 | 0.000 | 1.485 | 3.494 |
| pUK-SPDV-poly2#1 (1 ug/dose) | 20 | 1.027 | 0.619 | 0.738 | 1.317 | 0.000 | 0.943 | 2.090 |
| pUK-SPDV-poly2#1 (2 ug/dose) | 20 | 0.883 | 0.751 | 0.531 | 1.234 | 0.000 | 0.852 | 2.433 |
| pUK-SPDV-poly2#1 (5 ug/dose) | 20 | 0.937 | 0.706 | 0.607 | 1.268 | 0.000 | 0.935 | 2.408 |
| pUK-SPDV-poly2#1 (10 ug/dose) | 20 | 0.859 | 0.742 | 0.511 | 1.206 | 0.000 | 0.852 | 2.389 |
| pUK-SPDV-poly2#1 (20 ug/dose) | 20 | 0.877 | 0.538 | 0.626 | 1.129 | 0.000 | 0.852 | 2.055 |

TABLE 14

Results from an ANOVA on Histological Index Score among Treatments within Day 19

| Treatment | vs. Treatment | Least Squares Mean Difference | p-value |
|---|---|---|---|
| Saline (Control) | pUK-SPDV-poly2#1 (0.5 ug/dose) | −0.212 | 0.5058 |
| | pUK-SPDV-poly2#1 (1 ug/dose) | 0.506 | 0.1131 |
| | pUK-SPDV-poly2#1 (2 ug/dose) | 1.088 | 0.0008** |
| | pUK-SPDV-poly2#1 (5 ug/dose) | 1.449 | <.0001** |
| | pUK-SPDV-poly2#1 (10 ug/dose) | 1.386 | <.0001** |
| | pUK-SPDV-poly2#1 (20 ug/dose) | 1.310 | <.0001** |
| pUK-SPDV-poly2#1 (0.5 ug/dose) | pUK-SPDV-poly2#1 (1 ug/dose) | 0.717 | 0.0253* |
| | pUK-SPDV-poty2#1 (2 ug/dose) | 1.300 | <.0001** |
| | pUK-SPDV-poly2#1 (5 ug/dose) | 1.661 | <.0001** |
| | pUK-SPDV-poly2#1 (10 ug/dose) | 1.597 | <.0001** |
| | pUK-SPDV-poly2#1 (20 ug/dose) | 1.521 | <.0001** |

TABLE 14-continued

Results from an ANOVA on Histological Index Score among Treatments within Day 19

| Treatment | vs. Treatment | Least Squares Mean Difference | p-value |
|---|---|---|---|
| pUK-SPDV-poly2#1 (1 ug/dose) | pUK-SPDV-poly2#1 (2 ug/dose) | 0.583 | 0.0683 |
| | pUK-SPDV-poly2#1 (5 ug/dose) | 0.944 | 0.0035** |
| | pUK-SPDV-poly2#1 (10 ug/dose) | 0.880 | 0.0063** |
| | pUK-SPDV-poly2#1 (20 ug/dose) | 0.804 | 0.0123* |
| pUK-SPDV-poly2#1 (2 ug/dose) | pUK-SPDV-poly2#1 (5 ug/dose) | 0.361 | 0.2567 |
| | pUK-SPDV-poly2#1 (10 ug/dose) | 0.297 | 0.3500 |
| | pUK-SPDV-poly2#1 (20 ug /dose) | 0.222 | 0.4857 |
| pUK-SPDV-poly2#1 (5 ug/dose) | pUK-SPDV-poly2#1 (10 ug/dose) | −0.064 | 0.8408 |
| | pUK-SPDV-poly2#1 (20 ug/dose) | −0.139 | 0.6607 |
| pUK-SPDV-poly2#1 (10 ug/dose) | pUK-SPDV-poly2#1 (20 ug/dose) | −0.076 | 0.8117 |

1-Least Squares Mean
*Statistically significant at $p \leq 0.05$
**Statistically significant at $p \leq 0.01$ A statistically significant difference existed in mean histological index score within Day 19 between saline (control) and all vaccine groups with dosage levels higher than 1 µg/dose; between pUK-SPDV-poly2#1 (0.5 µg/dose) and all other treatments with higher dosage levels; and between pUK-SPDV-poly2#1 (1 µg/dose) and all other treatments with dosage levels higher than 2 µg/dose.

No statistically significant differences existed between the control and either the 0.5 or 1 µg/dose. No statistically significant differences existed between the 1 µg/dose and the 2 µg/dose. No statistically significant differences existed between the 2 µg/dose and all higher dose groups.

TABLE 15

Results from an ANOVA on Histological Index Score among Treatments within Day 26

| Treatment | vs. Treatment | Least Squares Mean Difference | p-value |
|---|---|---|---|
| Saline (Control) | pUK-SPDV-poly2#1 (0.5 ug/dose) | 2.344 | 0.0018** |
| | pUK-SPDV-poly2#1 (1 ug/dose) | 3.511 | <.0001** |
| | pUK-SPDV-poly2#1 (2 ug/dose) | 5.839 | <.0001** |
| | pUK-SPDV-poly2#1 (5 ug/dose) | 6.086 | <.0001** |
| | pUK-SPDV-poly2#1 (10 ug/dose) | 5.693 | <.0001** |
| | pUK-SPDV-poly2#1 (20 ug/dose) | 5.458 | <.0001** |
| pUK-SPDV-poly2#1 (0.5 ug/dose) | pUK-SPDV-poly2#1 (1 ug/dose) | 1.167 | 0.1144 |
| | pUK-SPDV-poly2#1 (2 ug/dose) | 3.495 | <.0001** |
| | pUK-SPDV-poly2#1 (5 ug/dose) | 3.742 | <.0001** |
| | pUK-SPDV-poly2#1 (10 ug/dose) | 3.349 | <.0001** |
| | pUK-SPDV-poly2#1 (20 ug/dose) | 3.114 | <.0001** |
| pUK-SPDV-poly2#1 (1 ug/dose) | pUK-SPDV-poly2#1 (2 ug/dose) | 2.328 | 0.0019** |
| | pUK-SPDV-poly2#1 (5 ug/dose) | 2.575 | 0.0006** |
| | pUK-SPDV-poly2#1 (10 ug/dose) | 2.182 | 0.0035** |
| | pUK-SPDV-poly2#1 (20 ug/dose) | 1.947 | 0.0090** |
| pUK-SPDV-poly2#1 (2 ug/dose) | pUK-SPDV-poly2#1 (5 ug/dose) | 0.247 | 0.7375 |
| | pUK-SPDV-poly2#1 (10 ug/dose) | −0.146 | 0.8426 |
| | pUK-SPDV-poly2#1 (20 ug/dose) | −0.381 | 0.6043 |
| pUK-SPDV-poly2#1 (5 ug/dose) | pUK-SPDV-poly2#1 (10 ug/dose) | −0.393 | 0.5937 |
| | pUK-SPDV-poly2#1 (20 ug/dose) | −0.628 | 0.3938 |
| pUK-SPDV-poly2#1 (10 ug/dose) | pUK-SPDV-poly2#1 (20 ug/dose) | −0.235 | 0.7490 |

*Statistically significant at $p \leq 0.05$
**Statistically significant at $p \leq 0.01$ A statistically significant difference existed in mean histological index score within Day 26 between the saline (control) and all vaccine groups; between pUK-SPDV-poly2#1 (0.5 µg/dose) and all other treatments with dosage levels higher than 1 µg/dose; and between pUK-SPDV-poly2#1 (1 µg/dose) and all other treatments with higher dosage levels. No statistically significant differences existed between the 0.5 µg/dose and the 1 µg/dose. No statistically significant differences existed between the 2 µg/dose and all higher dose groups.

TABLE 16

Results from an ANOVA on Histological Index Score among Treatments within Day 35

| Treatment | vs. Treatment | Least Squares Mean Difference | p-value |
|---|---|---|---|
| Saline (Control) | pUK-SPDV-poly2#1 (0.5 ug/dose) | 0.080 | 0.7263 |
| | pUK-SPDV-poly2#1 (1 ug/dose) | 0.681 | 0.0032** |
| | pUK-SPDV-poly2#1 (2 ug/dose) | 0.826 | 0.0004** |
| | pUK-SPDV-poly2#1 (5 ug/dose) | 0.771 | 0.0009** |
| | pUK-SPDV-poly2#1 (10 ug/dose) | 0.850 | 0.0003** |
| | pUK-SPDV-poly2#1 (20 ug/dose) | 0.831 | 0.0004** |
| pUK-SPDV-poly2#1 (0.5 ug/dose) | pUK-SPDV-poly2#1 (1 ug/dose) | 0.602 | 0.0090** |
| | pUK-SPDV-poly2#1 (2 ug/dose) | 0.746 | 0.0013** |
| | pUK-SPDV-poly2#1 (5 ug/dose) | 0.692 | 0.0028** |
| | pUK-SPDV-poly2#1 (10 ug/dose) | 0.770 | 0.0009** |
| | pUK-SPDV-poly2#1 (20 ug/dose) | 0.752 | 0.0012** |
| pUK-SPDV-poly2#1 (1 ug/dose) | pUK-SPDV-poly2#1 (2 ug/dose) | 0.144 | 0.5255 |
| | pUK-SPDV-poly2#1 (5 ug/dose) | 0.090 | 0.6928 |
| | pUK-SPDV-poly2#1 (10 ug/dose) | 0.168 | 0.4593 |
| | pUK-SPDV-poly2#1 (20 ug/dose) | 0.150 | 0.5100 |
| pUK-SPDV-poly2#1 (2 ug/dose) | pUK-SPDV-poly2#1 (5 ug/dose) | −0.055 | 0.8103 |
| | pUK-SPDV-poly2#1 (10 ug/dose) | 0.024 | 0.9160 |
| | pUK-SPDV-poly2#1 (20 ug/dose) | 0.005 | 0.9808 |
| pUK-SPDV-poly2#1 (5 ug/dose) | pUK-SPDV-poly2#1 (10 ug/dose) | 0.079 | 0.7297 |
| | pUK-SPDV-poly2#1 (20 ug/dose) | 0.060 | 0.7917 |
| pUK-SPDV-poly2#1 (10 ug/dose) | pUK-SPDV-poly2#1 (20 ug/dose) | −0.019 | 0.9351 |

*Statistically significant at $p \leq 0.05$
**Statistically significant at $p \leq 0.01$ A statistically significant difference existed in mean histological index score within Day 35 between the saline (control) and all vaccine groups with dosage levels higher than 0.5 µg/dose; and between pUK-SPDV-poly2#1 (0.5 µg/dose) and all other treatments with higher dosage levels.

No statistically significant differences existed between the control and the 0.5 µg/dose.

No statistically significant differences existed between the 1 µg/dose and all higher dose groups.

TABLE 17

Summary Statistics for Ct for Gene of Interest, SAV-nsP1, and Reference Gene, Ef1a, by Day and Treatment

| Tank | Treatment Group | N[1] | Ct, Reference Gene, Ef1a | | | | Ct, Gene of Interest, SAV-nsP1 | | | |
|---|---|---|---|---|---|---|---|---|---|---|
| | | | Mean | SD | Lower Bound | Upper Bound | Mean | SD | Lower Bound | Upper Bound |
| Day 0 | NEGATIVE Control | 10 | 22.77 | 0.82 | 22.19 | 23.36 | 39.90 | 0.32 | 39.67 | 40.13 |
| Day 19 | Saline (Control) | 36 | 21.44 | 1.01 | 21.10 | 21.78 | 21.38 | 3.67 | 20.13 | 22.62 |
| | pUK-SPDV-poly2#1 (0.5 ug/dose) | 39 | 21.69 | 1.23 | 21.29 | 22.09 | 24.76 | 6.96 | 22.51 | 27.02 |
| | pUK-SPDV-poly2#1 (1 ug/dose) | 39 | 21.51 | 1.23

TABLE 19-continued

Results from an ANOVA on ΔCt among Treatments for Day 19

| Treatment | vs. Treatment | Least Squares Mean Difference | p-value |
|---|---|---|---|
| pUK-SPDV-poly2#1 (5 ug/dose) | pUK-SPDV-poly2#1 (10 ug/dose) | 1.067 | 0.3551 |
| | pUK-SPDV-poly2#1 (20 ug/dose) | 0.150 | 0.8962 |
| pUK-SPDV-poly2#1 (10 ug/dose) | pUK-SPDV-poly2#1 (20 ug/dose) | −0.918 | 0.4173 |

*Statistically significant at p ≤ 0.05
**Statistically significant at p ≤ 0.01

Statistically significant differences in mean ΔCt within Day 19 existed among all ea ents, except among pUK-SPDV-poly2#1 (5 ug/dose), (10 ug/dose) and (20 ug/dose).

Statistically significant differences in mean delta Ct within Day 19 existed among all treatments, except among pUK-SPDV-poly2#1 (5 μg/dose), (10 μg/dose) and (20 μg/dose)

TABLE 20

Results from an ANOVA on ΔCt among Treatments for Day 26

| Treatment | vs. Treatment | Least Squares Mean Difference | p-value |
|---|---|---|---|
| Saline (Control) | pUK-SPDV-poly2#1 (0.5 ug/dose) | −2.436 | 0.0312* |
| | pUK-SPDV-poly2#1 (1 ug/dose) | −9.304 | <.0001** |
| | pUK-SPDV-poly2#1 (2 ug/dose) | −11.664 | <.0001** |
| | pUK-SPDV-poly2#1 (5 ug/dose) | −15.148 | <.0001** |
| | pUK-SPDV-poly2#1 (10 ug/dose) | −14.600 | <.0001** |
| | pUK-SPDV-poly2#1 (20 ug/dose) | −15.787 | <.0001** |
| pUK-SPDV-poly2#1 (0.5 ug/dose) | pUK-SPDV-poly2#1 (1 ug/dose) | −6.869 | <.0001** |
| | pUK-SPDV-poly2#1 (2 ug/dose) | −9.228 | <.0001** |
| | pUK-SPDV-poly2#1 (5 ug/dose) | −12.712 | <.0001** |
| | pUK-SPDV-poly2#1 (10 ug/dose) | −12.165 | <.0001** |
| | pUK-SPDV-poly2#1 (20 ug/dose) | −13.351 | <.0001** |
| pUK-SPDV-poly2#1 (1 ug/dose) | pUK-SPDV-poly2#1 (2 ug/dose) | −2.359 | 0.0319** |
| | pUK-SPDV-poly2#1 (5 ug/dose) | −5.843 | <.0001** |
| | pUK-SPDV-poly2#1 (10 ug/dose) | −5.296 | <.0001** |
| | pUK-SPDV-poly2#1 (20 ug/dose) | −6.482 | <.0001** |
| pUK-SPDV-poly2#1 (2 ug/dose) | pUK-SPDV-poly2#1 (5 ug/dose) | −3.484 | 0.0017** |
| | pUK-SPDV-poly2#1 (10 ug/dose) | −2.936 | 0.0066** |
| | pUK-SPDV-poly2#1 (20 ug/dose) | −4.123 | 0.0002** |
| pUK-SPDV-poly2#1 (5 ug/dose) | pUK-SPDV-poly2#1 (10 ug/dose) | 0.547 | 0.6174 |
| | pUK-SPDV-poly2#1 (20 ug/dose) | −0.639 | 0.5645 |
| pUK-SPDV-poly2#1 (10 ug/dose) | pUK-SPDV-poly2#1 (20 ug/dose) | −1.187 | 0.2728 |

*Statistically significant at p ≤ 0.05
**Statistically significant at p ≤ 0.01

Statistically significant differences in mean ΔCt within Day 26 existed among all reagents, except among pUK-SPDV-poly2#1 (5 ug/dose), (10 ug/dose) and (20 ug/dose).

Statistically significant differences in mean delta Ct within Day 26 existed among all treatments, except among pUK-SPDV-poly2#1 (5 μg/dose), (10 μg/dose) and (20 μg/dose)

TABLE 21

Results from an ANOVA on ΔCt among Treatments for Day 35

| Treatment | vs. Treatment | Least Squares Mean Difference | p-value |
|---|---|---|---|
| Saline (Control) | pUK-SPDV-poly2#1 (0.5 ug/dose) | −2.158 | 0.0182* |
| | pUK-SPDV-poly2#1 (1 ug/dose) | −5.517 | <.0001** |
| | pUK-SPDV-poly2#1 (2 ug/dose) | −11.692 | <.0001** |
| | pUK-SPDV-poly2#1 (5 ug/dose) | −14.614 | <.0001** |
| | pUK-SPDV-poly2#1 (10 ug/dose) | −14.160 | <.0001** |
| | pUK-SPDV-poly2#1 (20 ug/dose) | −14.305 | <.0001** |
| pUK-SPDV-poly2#1 (0.5 ug/dose) | pUK-SPDV-poly2#1 (1 ug/dose) | −3.359 | <.0002** |
| | pUK-SPDV-poly2#1 (2 ug/dose) | −9.534 | <.0001** |
| | pUK-SPDV-poly2#1 (5 ug/dose) | −12.456 | <.0001** |
| | pUK-SPDV-poly2#1 (10 ug/dose) | −12.002 | <.0001** |
| | pUK-SPDV-poly2#1 (20 ug/dose) | −12.147 | <.0001** |
| pUK-SPDV-poly2#1 (1 ug/dose) | pUK-SPDV-poly2#1 (2 ug/dose) | −6.176 | <.0001** |
| | pUK-SPDV-poly2#1 (5 ug/dose) | −9.098 | <.0001** |
| | pUK-SPDV-poly2#1 (10 ug/dose) | −8.643 | <.0001** |
| | pUK-SPDV-poly2#1 (20 ug/dose) | −8.789 | <.0001** |
| pUK-SPDV-poly2#1 (2 ug/dose) | pUK-SPDV-poly2#1 (5 ug/dose) | −2.922 | 0.0013** |
| | pUK-SPDV-poly2#1 (10 ug/dose) | −2.467 | 0.0063** |
| | pUK-SPDV-poly2#1 (20 ug/dose) | −2.613 | 0.0041** |
| pUK-SPDV-poly2#1 (5 ug/dose) | pUK-SPDV-poly2#1 (10 ug/dose) | 0.455 | 0.6123 |
| | pUK-SPDV-poly2#1 (20 ug/dose) | 0.309 | 0.7321 |
| pUK-SPDV-poly2#1 (10 ug/dose) | pUK-SPDV-poly2#1 (20 ug/dose) | −0.146 | 0.8719 |

*Statistically significant at p ≤ 0.05

**Statistically significant at p ≤ 0.01

Statistically significant differences in mean ΔCt within Day 35 existed among all treatments, except among pUK-SPDV-poly2#1 (5 ug/dose), 10 ug/dose) and (20 ug/dose).

Statistically significant differences in mean delta Ct within Day 35 existed among all treatments, except among pUK-SPDV-poly2#1 (5 μg/dose), (10 μg/dose) and (20 μg/dose)

TABLE 22

Correlation of Histological Index Score & ΔCt within Day

| Day | Pearson Correlation | p-value |
|---|---|---|
| Day 19 | −0.648 | <.0001** |
| Day 26 | −0.718 | <.0001** |
| Day 35 | −0.361 | <.0001** |

**Statistically significant at p ≤ 0.01

Statistically significant correlation existed between histological index score and ΔCt for all days, All were negatively correlated. The highest correlation, in absolute value, was for Day 26, followed by Day 19, and then Day 35

TABLE 23

Schematic Illustrating Statistically Significant Differences Among Groups within Days 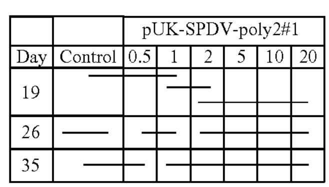 Results from the analysis of the data from Day 19 indicate no statistically significant differences in mean histological index score among the Control (0 ug/dose), 0.5 ug/dose, and the 1 ug/dose groups; nor between the 1 ug/dose and the 2 ug/dose group. No statistically significant differences existed among the 2 through 20 ug/dose groups.

The data from Tables 5-23 suggest that the optimal protection at Day 19 is provided by a 10 μg dose and that the minimal protective dose is 5 μg. The data also suggests that optimal protection is provided at days 26 and 35 by a 10 μg dose and that the minimal protective dose at this timepoint is 2 μg.

These studies demonstrate that pUK-SPDV-poly2#1 is a highly efficient vaccine (as compared to saline control), exhibits an excellent safety profile with only marginal and transient increases in local reactions at the site of injection, rapid clearance of plasmid from gut, spleen, gonads, head kidney and heart with no plasmid detectable in any organ at day 36 post vaccination, rapid clearance of plasmid from muscle at the injection site with plasmid levels dropping to below 5% of day 1 levels within 7 days post vaccination (except for gut: within 36 days), and was only detectable at minuscule levels (at <0.11% of day 1 levels; 2× vaccine) up to day 759 post-vaccination. In addition, it has been demonstrated that the heart histopathology index provides a highly sensitive measure for efficacy and safety, with excellent assay robustness.

Example 7

A study was performed comparing the efficacy of an inactivated whole virus vaccine compared to a DNA vaccine comprising pUK-SPDV-poly2#1. The DNA vaccine was administered at a dose of 10 micrograms and 20 micrograms, the dose per fish being 0.05 ml intramuscularly. The inactivated whole virus vaccine was the commercially available Norvax®Compact PD (Intervet AS), used as a dose per fish of 0.1 ml intraperitoneally.

2,670 naïve Atlantic salmon were used with an average weight of 44.9 g at the beginning of the study. 2,200 fish were divided amongst the five test groups, 440 were used as Trojan (shedders) for challenge, and 30 fish were used for the time zero as naïve control samples.

To comply with the recommended vaccination program outlined on the label of the Norvax® Compact PD vaccine product, the vaccination regime was divided into two phases separated by a 213 degree day period as per the label recommendation. Vaccination phase 1 included the administration of the various PD vaccine treatments or saline for the negative control groups. Vaccination phase 2 included either the administration of saline or an intrapertioneal 0.1 ml dose per fish of a vaccine with an oil adjuvant, which did not contain antigens against PD (Norvax® Minova 6, Intervet AS: contains inactivated strains of *Listonella* (*Vibrio*) *anguillarum* serovar O1, *Listonella* (*Vibrio*) *anguillarum* serovar O2α, *Aeromonas salmonicida* subsp. *salmonicida*, *Vibrio salmonicida* and *Moritella viscosa*, and surface protein from IPN virus serotype Sp.). Both vaccinations were performed at approx. 12C.

The Negative control groups were injected intraperitoneally with 0.1 ml of a 0.9% NaCl solution.

TABLE 24

| Groups | Group names | Group Markings | No. of fish | Vaccination 1 (0 dd) | Vaccination 2 (213 dd) |
|---|---|---|---|---|---|
| Negative-negative control | PBS | Adipose fins | 440 | Saline | saline |
| negative control | Oil multivalent | Right maxilla | 440 | Saline | Norvax ® Minova 6 |
| positive control | Commercial PD | Left maxilla | 440 | Norvax ® Compact PD | Norvax ® Minova 6 |
| Treatment A | PD NAV 10 micrograms | Right Maxilla + Adipose fin | 440 | PD NAV 10 microgram | Norvax ® Minova 6 |
| Treatment B | PD NAV 20 micrograms | left Maxilla + Adipose fin | 440 | PD NAV 20 microgram | Norvax ® Minova 6 |

Following the second vaccination, each treatment group was equally divided among four tanks (110 fish/group/tank). Thus the five different groups were co-habited for the remaining of the study. The fish were then challenged at 731 dd and 2050 dd with a SAV-3 isolate from tissue homogenates prepared from the heart of clinically symptomatic fish from an outbreak in Norway. Each challenge was performed in duplicate tanks using a full cohabitation model including 20% shedders per tank administered with 0.1 ml intraperitoneal injection of the SAV-3 isolate. Histology samples of heart and pancreas were collected on day 18, 22 and 26 post-challenge. 30 fish were also sampled prior to vaccination as a control, as well as 5 fish from all groups from both replicates (total 50 fish) prior to challenge at 731 dd and 2050 dd as a post-vaccination control. Samples underwent a histopathological analysis as well as qRT-PCR to evaluate viral load in heart tissue. The data is presented as CT values (CT values are a measure of the number of cycles of amplification required to detect the virus; hence higher CT values indicated lower viral load and lower CT values indicate higher viral loads). The assay was designed to specifically target the SAV3 viral subtype. The CT values were then normalized against the elongation factor alpha, the reference gene. The normalized values were then averaged for each group (average deltaCT). The average deltaCT value obtained for the negative-negative (PBS) control group was then subtracted for the group's average deltaCT and the results elevated to the power of 2 due to the exponential nature of PCR amplification. The final data gave a representation of the fold decrease of virus concentration in the heart samples when compared to the negative control group.

The safety of the DNA vaccine was assessed by monitoring the mortality of the vaccinated Atlantic salmon over an 18 day period. No adverse effect or mortality was observed during this period for either dosage amount.

TABLE 25

Histopathology scores for Pancreas Degeneration/Necrosis:
731 dd challenge, 22 days post challenge
Severity of acinar necrosis was evaluated on a scale ranging from level 0 representing normal tissue to level 3 indicative of a marked degeneration and necrosis of the tissues.

| Treatments | N obs | N | Mean | Std dev | Min | Max |
|---|---|---|---|---|---|---|
| PBS | 60 | 60 | 2.35 | 0.82 | 0 | 3 |
| Oil multivalent | 61 | 60 | 1.85 | 0.936 | 0 | 3 |
| Commercial PD | 60 | 60 | 1.517 | 1.186 | 0 | 3 |
| PD NAV 10 micrograms | 59 | 59 | 0.237 | 0.625 | 0 | 3 |
| PD NAV 20 micrograms | 61 | 61 | 0.197 | 0.572 | 0 | 3 |

TABLE 26

Histopathology scores for Pancreas Degeneration/
Necrosis: 2050 dd challenge, 26 days post challenge

| Treatments | N obs | N | Mean | Std dev | Min | Max |
|---|---|---|---|---|---|---|
| PBS | 60 | 60 | 2.967 | 0.181 | 2 | 3 |
| Oil multivalent | 60 | 60 | 2.6 | 0.643 | 0 | 3 |
| Commercial PD | 60 | 59 | 2.492 | 0.972 | 0 | 3 |
| PD NAV 10 micrograms | 61 | 60 | 0.383 | 0.761 | 0 | 3 |
| PD NAV 20 micrograms | 61 | 61 | 0.77 | 1.131 | 0 | 3 |

N obs: Number of observations
N: number of data points

At 731 dd post-vaccination and 22 days post challenge, the PD NAV (both 10 and 20 micrograms) scored less than 0.3 for pancreas necrosis, a significant ($p<0.001$) reduction when compared to the negative-negative PBS group averaging a score of 2.4, the negative (oil-multivalent) control averaging 1.9 as well as the commercial inactivated vaccine (Compact PD) averaging 1.5.

A similar trend was observed for the 2050 dd/26 days post challenge data even though the infection in the negative control was more severe. For this challenge time point, the PD NAV scored less than 0.8, showing a significant ($p<0.001$) reduction from the negative-negative (PBS) group averaging a score of 3.0, the negative (oil-multivalent) control averaging 2.6 and the commercial inactivated vaccine (Compact PD) averaging 2.5.

Heart Histopathology
Severity of myocyte necrosis was evaluated on a scale ranging from level 0 representing normal tissue to level 3 indicative of a marked degeneration and necrosis of the tissue.

TABLE 27

Histopathology scores for Heart Necrosis 731 dd challenge,
22 days post challenge

| Treatments | N obs | N | Mean | Std dev | Min | Max |
|---|---|---|---|---|---|---|
| PBS | 60 | 60 | 1.33 | 0.774 | 0 | 3 |
| Oil multivalent | 61 | 61 | 1.23 | 0.716 | 0 | 3 |
| Commercial PD | 60 | 60 | 0.967 | 0.863 | 0 | 3 |
| PD NAV 10 micrograms | 59 | 59 | 0.068 | 0.254 | 0 | 1 |
| PD NAV 20 micrograms | 61 | 61 | 0.033 | 0.18 | 0 | 1 |

TABLE 28

Histopathology scores for Heart Necrosis: 2050 dd challenge,
26 days post challenge

| Treatments | N obs | N | Mean | Std dev | Min | Max |
|---|---|---|---|---|---|---|
| PBS | 60 | 60 | 2.433 | 0.722 | 1 | 3 |
| Oil multivalent | 60 | 60 | 2.05 | 0.832 | 0 | 3 |
| Commercial PD | 59 | 59 | 1.864 | 1.09 | 0 | 3 |
| PD NAV 10 micrograms | 60 | 59 | 0.254 | 0.544 | 0 | 3 |
| PD NAV 20 micrograms | 61 | 60 | 0.35 | 0.685 | 0 | 3 |

N obs: Number of observations
N: number of data points

At 731 dd post-vaccination and 22 days post challenge, the PD NAV (both 10 and 20 micrograms) scored less than 0.1 for heart histopathology, a significant ($p<0.001$) reduction when compared to the negative-negative PBS group averaging a score of 1.3, the negative (oil-multivalent) control averaging 1.2, as well as the commercial inactivated vaccine (Compact PD) averaging 1.0.

For the durational response 2050 dd and 26 days post challenge the PD NAV. For this challenge time point, the PD NAV (both 10 and 20 micrograms) scored less than 0.4 for heart histopathology, a significant ($p<0.001$) reduction when compared to the negative-negative (PBS) group averaging a score of 2.4, the negative (oil-multivalent) control averaging 2.1 and the commercial inactivated vaccine (Compact PD) averaging 1.9.

Prevalence of the SAV3 Virus by qRT-PCR
A RT-qPCR method was used to detect SAV3 viruses in heart tissue. The assay was used to evaluate the severity of virus propagation as well as the percentage of infection in each treatment group.

Severity of Virus Propagation
The percentage of heart samples with a positive diagnostic for SAV3 was calculated based on the qRT-PCR results. Samples with a CT value greater than or equal to 37 were considered negative and scored as 0 value, while CT value less than 37 were considered positive and given a value of 1. The calculated means and associated standard deviations are in the table below.

TABLE 29

Assessment of presence or absence of the SAV-3 virus in
heart tissues qRT-PCR diagnostics
731 dd challenge/22 days post challenge

| Treatments | N obs | N | Mean | Std dev | Min | Max |
|---|---|---|---|---|---|---|
| PBS | 60 | 60 | 1 | 0 | 1 | 1 |
| Oil multivalent | 61 | 61 | 0.967 | 0.18 | 0 | 1 |
| Commercial PD | 60 | 60 | 0.833 | 0.376 | 0 | 1 |
| PD NAV 10 micrograms | 59 | 59 | 0.407 | 0.495 | 0 | 1 |
| PD NAV 20 micrograms | 61 | 60 | 0.417 | 0.497 | 0 | 1 |

TABLE 30

Assessment of presence or absence of the SAV-3 virus in
heart tissues qRT-PCR diagnostics
2050 dd challenge/26 days post challenge

| Treatments | N obs | N | Mean | Std dev | Min | Max |
|---|---|---|---|---|---|---|
| PBS | 60 | 59 | 1 | 0 | 1 | 1 |
| Oil multivalent | 60 | 60 | 1 | 0 | 1 | 1 |

TABLE 30-continued

Assessment of presence or absence of the SAV-3 virus in
heart tissues qRT-PCR diagnostics
2050 dd challenge/26 days post challenge

| Treatments | N obs | N | Mean | Std dev | Min | Max |
|---|---|---|---|---|---|---|
| Commercial PD | 59 | 59 | 0.966 | 0.183 | 0 | 1 |
| PD NAV 10 micrograms | 60 | 60 | 0.583 | 0.497 | 0 | 1 |
| PD NAV 20 micrograms | 61 | 61 | 0.574 | 0.499 | 0 | 1 |

N obs: Number of observations
N: number of data points

At 731 dd post-vaccination and 22 days post challenge, the PD NAV (both 10 and 20 micrograms) had significantly ($p<0.001$) lower SAV3 detection rate (40.7%, 41.7% respectively) when compared to the negative-negative PBS group (100%), the negative (oil-multivalent) control (96.7%), as well as the commercial inactivated vaccine (Compact PD) (83.3%).

For the 2050 dd challenge, PD NAV vaccinated fish had a significantly lower ($p<0.001$) SAV3 detection rate (58.3%, 57.4%) when compared to the PBS negative control (100%), multivalent oil control (100%) and the inactivated PD vaccine (Compact PD) (96.6%).

Relative Virus Concentration in Heart Tissues

The number of cycle (CT) to obtain a positive signal for the presence of SAV3 viral particles found in heart tissue was measured by qRT-PCR.

TABLE 31

Relative virus concentration in heart tissues
731 dd challenge/22 days post challenge

| Treatments | N obs | N | Average delta CT | Delta deltaCT | 2exp(-deltadeltaCT) |
|---|---|---|---|---|---|
| PBS | 60 | 60 | 0.97 | 0.00 | 0.997 |
| Oil multivalent | 61 | 61 | -0.39 | -1.36 | 2.575 |
| Commercial PD | 60 | 60 | -3.50 | -4.47 | 22.192 |
| PD NAV 10 micrograms | 59 | 59 | -13.96 | -14.93 | 31249.065 |
| PD NAV 20 micrograms | 61 | 60 | -13.72 | -14.69 | 26493.179 |

TABLE 32

Relative virus concentration in heart tissues
2050 dd challenge/26 days post challenge

| Treatments | N obs | N | Average delta CT | Delta delta CT | 2exp(-deltadeltaCT) |
|---|---|---|---|---|---|
| PBS | 60 | 59 | 0.56 | 0.00 | 0.998 |
| Oil multivalent | 60 | 60 | 0.52 | -0.04 | 1.032 |
| Commercial PD | 59 | 59 | -0.74 | -1.30 | 2.460 |
| PD NAV 10 micrograms | 60 | 60 | -12.68 | -13.24 | 9671.585 |
| PD NAV 20 micrograms | 61 | 61 | -10.66 | -11.22 | 2379.649 |

N obs: Number of observations
N: number of data points

At 518 dd post-vaccination and following a challenge, SAV-3 concentration was 26400 to 31400 fold less in the heart tissue for PD NAV vaccinated fish, 3 fold less for the oil multivalent, and 22 fold less for the inactivated PD vaccine than the levels detected in the PBS negative control group. For the 2050 dd challenge, SAV3 concentration was 2300 to 9600 fold less in the heart tissue for PD NAV vaccinated fish, 1 fold less for the oil multivalent control and 2 fold less for the inactivated PD vaccine than the levels detected in the PBS negative control group.

In conclusion the pUK-SPDV-poly2#1 DNA vaccine was superior in preventing the development of tissue necrosis in target organs as well as reducing viral propagation in heart tissue, when administered at either a 10 or 20 microgram dose as compared to an inactivated whole virus vaccine and negative controls. Superiority was conformed at both early onset (731 dd) and late onset (2050 days) of immunity indicating this vaccines offers durational protection.

It is to be understood that any reference to a particular range includes all individual values and sub-ranges within that range as if each were individually listed herein. All references cited within this application are incorporated by reference in their entirety. While the present invention has been described in terms of the preferred embodiments, it is understood that variations and modifications will occur to those skilled in the art. Therefore, it is intended that the appended claims cover all such equivalent variations that come within the scope of the invention as claimed.

REFERENCES

Bolivar, et al. Construction and characterization of new cloning vehicles. I. Ampicillin-resistant derivatives of the plasmid pMB9. 1977a. Gene. 2:75-93.

Bolivar, et al. 1977b. Construction and characterization of new cloning vehicles. II. A multipurpose cloning system. Gene. 2:95-113.

Covarrubias et al. 1981. Construction and characterization of new cloning vehicles. V. Mobilization and coding properties of pBR322 and several deletion derivatives including pBR327 and pBR328. Gene. 13:25-35.

Jørgensen, et al. 2003. CpG DNA induces protective antiviral immune responses in Atlantic salmon (*Salmo salar* L.). J Virol. 77:11471-9.

Krieg, et al. 2004. Vectors and methods for immunization or therapeutic protocols. U.S. Pat. No. 6,821,957.

Scott J R. 1984. Regulation of plasmid replication. Microbiol Rev. 48:1-23.

Strandskog, et al. 2007. Characterization of three distinct CpG oligonucleotide classes which differ in ability to induce IFN alpha/beta activity and cell proliferation in Atlantic salmon (*Salmo salar* L.) leukocytes. Dev Comp Immunol, 31:39-51.

Strauss, et al. 1994. The alphaviruses: gene expression, replication, and evolution. Microbiol Rev. 58:491-562.

Tomizawa, et al. 1974. Replication of Colicin E1 Plasmid DNA in Cell Extracts. Origin and Direction of Replication. PNAS. 71:2260-2264.

Villoing, et al. 2000. Rainbow trout sleeping disease virus is an atypical alphavirus. J Virol. 74:173-83.

Weston, et al. 1999. Salmon pancreas disease virus, an alphavirus infecting farmed Atlantic salmon, *Salmo salar* L. Virology. 256:188-95.

The invention claimed is:

1. A deoxyribonucleic acid (DNA) expression vector encoding a salmon alphavirus (SAV) polyprotein; wherein said SAV polyprotein is at least 98% identical with SEQ ID NO: 5.

2. The DNA expression vector of claim 1, comprising a nucleic acid sequence selected from the group consisting of SEQ ID NO: 1, SEQ ID NO: 2 and SEQ ID NO: 3.

3. A DNA expression vector encoding a SAV polyprotein comprising the sequence of SEQ ID NO: 5.

4. A method for inducing an immune response in a host against a salmon alphavirus comprising administering to the host a DNA expression vector encoding a SAV polyprotein; wherein said SAV polyprotein is at least 98% identical with SEQ ID NO:5.

5. A method for inducing an immune response in a host against a salmon alphavirus comprising administering to the host a polypeptide or peptides sharing at least 98% identity with SEQ ID NO: 5.

6. The method of claim 4, wherein said DNA expression vector is a plasmid which is administered by injection into muscle tissue.

7. The method of claim 4, wherein two to 20 micrograms of said DNA expression vector is administered to the host.

8. A vaccine comprising the DNA expression vector of claim 1.

9. The method of claim 7, wherein 5 to 10 micrograms of the DNA expression vector is administered to the host.

10. The method of claim 4, wherein the DNA expression vector is a supercoiled plasmid; and wherein 5 to 10 micrograms of the DNA expression vector is administered to the host by injection into muscle tissue.

11. A method for inducing an immune response in a host against a salmon alphavirus comprising administering to the host a DNA expression vector encoding a SAV polyprotein; wherein said expression vector comprises a sequence selected from the group of SEQ ID NO:1, SEQ ID NO: 2, and SEQ ID NO: 3.

12. The method of claim 11, wherein the DNA expression vector is a supercoiled plasmid; and wherein 5 to 10 micrograms of the DNA expression vector is administered to the host by injection into muscle tissue.

13. A vaccine comprising the DNA expression vector of claim 2.

14. A method for inducing an immune response in a host against a salmon alphavirus comprising administering to the host a DNA expression vector encoding a SAV polyprotein comprising the sequence of SEQ ID NO: 5.

15. The method of claim 14, wherein the DNA expression vector is a supercoiled plasmid; and wherein 5 to 10 micrograms of the DNA expression vector is administered to the host by injection into muscle tissue.

16. A vaccine comprising the DNA expression vector of claim 3.

* * * * *

SEQUENCE LISTING

<160> NUMBER OF SEQ ID NOS: 13

<210> SEQ ID NO 1
<211> LENGTH: 3984
<212> TYPE: DNA
<213> ORGANISM: SPDV

<400> SEQUENCE: 1

```
atgcatcatc accatcacca tatgtttccc atgcaattca ccaactcagc ctatcgccag      60
atggagccca tgttcgcacc ggcttctcga ggacaagtac agccgtatcg gccgcgcaca     120
aagcgccgcc aagagccgca agtcggcaac gctgctattg ctgccctcgc gaaccagatg     180
agcgcgctcc agctgcaggt ggctggactt gccggccagg caagggtgga ccgtcgtgga     240
ccgagacgtg ttcagaagaa caagcagaag aagaagaact cttccaacgg agaaaaaccc     300
aaggagaaga agaagaagca aaaacaacag gagaagaaag ggagcggcgg tgaaaaagtc     360
aagaagccac ggaaccggcc cgggaaggag gtaaggatct ccgtaaagcg tgcccgacag     420
agcaccttcc ccgtgtacca tgacggtgcc atatccggct atgcggtgct gattggctcc     480
cgcgtgttta agccagcgca cgtgaagggg aagatcgacc ccccgaact ggcggacatc     540 aagttccagg tcgccgagga catggacctc gaagcagccg catacccaa gagcatgcga     600 gaccaagcgg ctgaaccagc aaccatgacg gatggagtgt acaactggga atacggcact     660
atcagagtgg aggacaacgt cgtgatcgat gcgagcggca gaggcaagcc gggtgacagc     720
ggcagggcca tcaccgacaa ctcaggaaag gttgtcggta tcgtcctcgg aggaggaccc     780
gatggtaggc gcacacgtct ctccgtgata ggtttcgaca agaagctgaa ggccagagag     840
atcgcctaca gcgaggccat cccttggaca cgcgcaccag ctctcctgct gctgcccatg     900
gtcatcgcct gtacctacaa ctccaacacc tttgactgct ccaaaccgtc ctgccaggac     960
tgttgcatta ctgctgaacc aaagaaggcc atgactatgc tgaaggacaa cctgaatgac    1020
ccgaattact gggacctgct tattgccgtc accacctgca gttccgcccg aaaaaagagg    1080
gctgtgtcta cgtcgcctgc cgccgcttac gacacacaaa ttctcgccgc ccacgcagct    1140 gcctcccgt atagggcgta ctgccccgat tgtgacggaa ctgcctgcat ctcgccgata    1200
gctatcgacg aggtggtaag tagcggtagt gaccacgtcc ttcgcatccg ggtcggttct    1260
caatcgggag tgaccgctaa aggcggtgcg gcgggtgaaa cctctctgcg atacctggga    1320
agggacggta aggttcacgc cgcggacaac acgcggctcg tggtgcgcac cactgcaaag    1380
tgtgacgtgc tgcaggccac tggccactac attctggcca actgcccagt ggggcagagt    1440
ctcactgttg cggccacact ggacggcacc cggcatcaat gtaccacggt tttcgaacat    1500
caagtaacgg agaagttcac aagagaacgc agcaagggcc accacctgtc cgatctgacc    1560
aagaaatgca ccaggttttc caccaccccg aagaaatccg cgctctatct cgtggatgtg    1620
tatgacgctc tgccgatttc tgtagagatc agcaccgtgg tgacatgcaa cgaaagtcag    1680
tgcacagtga gggtgccacc cggtaccaca gtgaaattcg ataagaagtg caagagcgct    1740
gcccaagcga ccgtcacctt caccagcggc tcccagacgt ttacgtgcga ggagccggtc    1800
ctaacggccg ccagtatcac ccagggcaag ccgcaccta gatcgtcaat gctgcccagc    1860
```

```
ggaggcaaag aggtgaaagc gaggattcca ttcccgttcc cgccagagac tgcgacctgc    1920
agagtgagtg tcgccccact gccatcgatc acctatgagg aaagcgatgt cctgctggcc    1980
ggcactgcga ataccccgt gctgctaact acacggaatc ttggtttcca tagcaacgcc     2040
acatccgaat ggatccaggg taagtacctg cgccgcatcc cggtcacgcc caagggatc     2100
gaactaatgt ggggaaacaa cgcaccgctg cacttctggt catctgtcag gtacgcatct    2160
ggggacgccg acgcgtaccc ctgggaactt ctggtgcacc acatcaagca ccatccggag    2220
tatgcgtggg cgtttgtagg agttgcatgt ggcctactgg ccgttgcagc atgcgtgttt    2280
gcgtgcgcat gcaacagggt gcggtactct ctgcttgcca acacgttcaa cccgaaccca    2340
ccaccactga ccgcactgac tgcagcactg tgctgcatac ctggggctcg cgcggatcaa    2400
ccctacctgg acatcattgc ctacttgtgg accaacagca agtggccttc gggctgcaa     2460
tgcgcggcgc ccgtggcttg tatgctcatc gtcacatacg cccttagaca ctgcagattg    2520
tgctgcaagt cttttttagg ggtaagaggg tggtcggctc tgttggtcat ccttgcgtat    2580
gtacagagct gcaagagcta cgaacacacc gtggtggtcc aatggatcc aagagccccg     2640
tcgtacgagg cggtgataaa ccggaatggg tatgacccc tgaagctgac catcgcagtg     2700
aatttcaccg tcatctcacc aactacggct ctggaatact ggaccgtgc aggagtccct     2760
gtcgtcgagc cgcccatgt gggctgctgc acgtcagtgt cctgccccac cgacctctcc    2820
acgctgcacg cgttcaccgg caaagccgtc tccgacgtgc actgcgatgt gcacacaaac    2880
gtgtacccct tgttgtgggg tgcggctcac tgcttttgtt ccactgaaaa cacgcaggtc    2940
agcgctgtgg ccgccaccgt ttctgagttc tgcgctcagg acgcagaacg cgccgaggcg    3000
ttcagcgttc acagcagctc agtcactgca gagatcctgg tgacgcttgg tgaagtggtg    3060
acggcagtcc acgtttacgt ggacggggta acatcagcca ggggtaccga cctcaagatc    3120
gtggctggcc caataacaac tgactactcc ccgtttgatc gcaaagtagt ccgtatcagc    3180
gaagaggtct ataactacga ctggcctcct tacggggctg gtcgaccagg cacattcgga    3240
gacattcaag ctaggtcaac caactatgtc aaacccaatg atctgtacgg ggatatcggg    3300
attgaagtac tgcagccgac taatgaccac gtgcacgtgg cttacacgta tacgacctcc    3360
gggttactgc gttggttgca ggacgctccg aaaccactca gtgtcacagc accgcacggt    3420
tgtaagatca gtgctaaccc gctcctggcc ctcgattgtg gggttggtgc cgtccccatg    3480
tccatcaaca ttccggacgc gaagttcacc cgcaaattaa aggatccgaa accatcggcc    3540
ctgaaatgcg tggtggacag ttgcgagtac ggggtggact acggggcgc cgccacgatc    3600
acctacgagg ccacgaggc tgggaagtgc gggatccatt ccctgacacc aggagtccct    3660
ctgagaacat cagtggttga agtagttgcc ggcgctaata ccgtcaaaac gaccttctcc    3720
tcacccacgc ccgaggtcac actcgaggta gagatctgtt cggcaatagt gaagtgcgcc    3780
agtgagtgca ctccaccgaa ggaacacgta gtcgcagcca ggcctcgcca tggcagcgac    3840
actggaggct acatctccgg gcccgcaatg cgctgggccg gagggattgt agggacccta    3900
gtggtcctgt tcctcatcct tgccgtcacc tactgcgtgg tgaagaagtg ccgctctaaa    3960
agaatccgga tagtcaagag ctaa                                          3984
```

<210> SEQ ID NO 2
<211> LENGTH: 3963
<212> TYPE: DNA
<213> ORGANISM: SPDV

<400> SEQUENCE: 2

```
atgtttccca tgcaattcac caactcagcc tatcgccaga tggagcccat gttcgcaccg      60
gcttctcgag gacaagtaca gccgtatcgg ccgcgcacaa agcgccgcca agagccgcaa     120
gtcggcaacg ctgctattgc tgccctcgcg aaccagatga gcgcgctcca gctgcaggtg     180
gctggacttg ccggccaggc aagggtggac cgtcgtggac cgagacgtgt tcagaagaac     240
aagcagaaga agaagaactc ttccaacgga gaaaaaccca aggagaagaa gaagaagcaa     300
aaacaacagg agaagaaagg gagcggcggt gaaaaagtca agaagccacg gaaccggccc     360
gggaaggagg taaggatctc cgtaaagcgt gcccgacaga gcaccttccc cgtgtaccat     420
gacggtgcca tatccggcta tgcggtgctg attggctccc gcgtgtttaa gccagcgcac     480
gtgaagggta agatcgacca ccccgaactg gcggacatca gttccaggt cgccgaggac      540
atggacctcg aagcagccgc ataccccaag agcatgcgag accaagcggc tgaaccagca     600
accatgacgg atggagtgta caactgggaa tacggcacta tcagagtgga ggacaacgtc     660
gtgatcgatg cgagcggcag aggcaagccg ggtgacagcg gcagggccat caccgacaac     720
tcaggaaagg ttgtcggtat cgtcctcgga ggaggacccg atggtaggcg cacacgtctc     780
tccgtgatag gtttcgacaa gaagctgaag gccagagaga tcgcctacag cgaggccatc     840
ccttggacac gcgcaccagc tctcctgctg ctgcccatgg tcatcgcctg tacctacaac     900
tccaacacct ttgactgctc caaaccgtcc tgccaggact gttgcattac tgctgaacca     960
aagaaggcca tgactatgct gaaggacaac ctgaatgacc cgaattactg ggacctgctt    1020
attgccgtca ccacctgcag ttccgcccga aaaagaggg ctgtgtctac gtcgcctgcc    1080
gccgcttacg acacacaaat tctcgccgcc cacgcagctg cctccccgta tagggcgtac    1140
tgcccccgatt gtgacggaac tgcctgcatc tcgccgatag ctatcgacga ggtggtaagt    1200
agcggtagtg accacgtcct tcgcatccgg gtcggttctc aatcgggagt gaccgctaaa    1260
ggcggtgcgg cgggtgaaac ctctctgcga tacctgggaa gggacggtaa ggttcacgcc    1320
gcggacaaca cgcggctcgt ggtgcgcacc actgcaaagt gtgacgtgct gcaggccact    1380
ggccactaca ttctggccaa ctgcccagtg gggcagagtc tcactgttgc ggccacactg    1440
gacggcaccc ggcatcaatg taccacggtt ttcgaacatc aagtaacgga gaagttcaca    1500
agagaacgca gcaagggcca ccacctgtcc gatctgacca agaaatgcac caggtttttcc    1560
accaccccga agaaatccgc gctctatctc gtggatgtgt atgacgctct gccgatttct    1620
gtagagatca gcaccgtggt gacatgcaac gaaagtcagt gcacagtgag ggtgccaccc    1680
ggtaccacag tgaaattcga taagaagtgc aagagcgctg cccaagcgac cgtcaccttc    1740
accagcggct cccagacgtt tacgtgcgag agccggtcc taacggccgc cagtatcacc    1800
cagggcaagc cgcaccttag atcgtcaatg ctgcccagcg gaggcaaaga ggtgaaagcg    1860
aggattccat tccgttccc gccagagact gcgacctgca gagtgagtgt cgccccactg    1920
ccatcgatca cctatgagga aagcgatgtc ctgctggccg gcactgcgaa atacccgtg     1980
ctgctaacta cacggaatct tggttttccat agcaacgcca catccgaatg gatccagggt    2040
aagtaccctgc gccgcatccc ggtcacgccc aagggatcg aactaatgtg gggaaacaac    2100
gcaccgctgc acttctggtc atctgtcagg tacgcatctg gggacgccga cgcgtacccc    2160
tgggaacttc tggtgcacca catcaagcac catccggagt atgcgtgggc gtttgtagga    2220
gttgcatgtg gcctactggc cgttgcagca tgcgtgtttg cgtgcgcatg caacagggtg    2280
cggtactctc tgcttgccaa cacgttcaac ccgaacccac caccactgac cgcactgact    2340
```

```
gcagcactgt gctgcatacc tggggctcgc gcggatcaac cctacctgga catcattgcc      2400
tacttgtgga ccaacagcaa agtggccttc gggctgcaat gcgcggcgcc cgtggcttgt      2460
atgctcatcg tcacatacgc ccttagacac tgcagattgt gctgcaagtc ttttttaggg      2520
gtaagagggt ggtcggctct gttggtcatc cttgcgtatg tacagagctg caagagctac      2580
gaacacaccg tggtggtccc aatggatcca agagcccgt cgtacgaggc ggtgataaac       2640
cggaatgggt atgaccccct gaagctgacc atcgcagtga atttcaccgt catctcacca      2700
actacggctc tggaatactg gacctgtgca ggagtccctg tcgtcgagcc gccccatgtg      2760
ggctgctgca cgtcagtgtc ctgccccacc gacctctcca cgctgcacgc gttcaccggc      2820
aaagccgtct ccgacgtgca ctgcgatgtg cacacaaacg tgtaccccct gttgtggggt      2880
gcggctcact gcttttgttc cactgaaaac acgcaggtca cgcgctgtggc cgccaccgtt     2940 tctgagttct gcgctcagga cgcagaacgc gccgaggcgt cagcgttca cagcagctca      3000 gtcactgcag agatcctggt gacgcttggt gaagtggtga cggcagtcca cgtttacgtg      3060
gacggggtaa catcagccag gggtaccgac ctcaagatcg tggctggccc aataacaact      3120
gactactccc cgtttgatcg caaagtagtc cgtatcagcg aagaggtcta taactacgac      3180
tggcctcctt acgggctgg tcgaccaggc acattcggag acattcaagc taggtcaacc      3240
aactatgtca acccaatga tctgtacggg gatatcggga ttgaagtact gcagccgact      3300
aatgaccacg tgcacgtggc ttacacgtat acgacctccg ggttactgcg ttggttgcag      3360
gacgctccga aaccactcag tgtcacagca ccgcacggtt gtaagatcag tgctaacccg      3420
ctcctggccc tcgattgtgg ggttggtgcc gtccccatgt ccatcaacat tccggacgcg      3480
aagttcaccc gcaaattaaa ggatccgaaa ccatcggccc tgaaatgcgt ggtggacagt      3540
tgcgagtacg gggtggacta cgggggcgcc gccacgatca cctacgaggg ccacgaggct      3600
gggaagtgcg ggatccattc cctgacacca ggagtccctc tgagaacatc agtggttgaa      3660
gtagttgccg cgctaatac cgtcaaaacg accttctcct cacccacgcc cgaggtcaca      3720
ctcgaggtag agatctgttc ggcaatagtg aagtgcgcca gtgagtgcac tccaccgaag      3780
gaacacgtag tcgcagccag gcctcgccat ggcagcgaca ctggaggcta catctccggg      3840
cccgcaatgc gctgggccgg agggattgta gggaccctag tggtcctgtt cctcatcctt      3900
gccgtcacct actgcgtggt gaagaagtgc cgctctaaaa gaatccggat agtcaagagc      3960
taa                                                                    3963

<210> SEQ ID NO 3
<211> LENGTH: 7942
<212> TYPE: DNA
<213> ORGANISM: SPDV

<400> SEQUENCE: 3
ctagatccga tgtacgggcc agatatacgc gttgacattg attattgact agttattaat       60
agtaatcaat tacggggtca ttagttcata gcccatatat ggagttccgc gttacataac      120
ttacggtaaa tggcccgcct ggctgaccgc ccaacgaccc ccgcccattg acgtcaataa      180
tgacgtatgt tcccatagta acgccaatag ggactttcca ttgacgtcaa tgggtggagt      240
atttacggta aactgcccac ttggcagtac atcaagtgta tcatatgcca agtacgcccc      300
ctattgacgt caatgacggt aaatggcccg cctggcatta tgcccagtac atgaccttat      360
gggactttcc tacttggcag tacatctacg tattagtcat cgctattacc atggtgatgc      420
ggttttggca gtacatcaat gggcgtggat agcggtttga ctcacgggga tttccaagtc      480
```

-continued

```
tccaccccat tgacgtcaat gggagtttgt tttggcacca aaatcaacgg gactttccaa    540
aatgtcgtaa caactccgcc ccattgacgc aaatgggcgg taggcgtgta cggtgggagg    600
tctatataag cagagctctc tggctaacta gagaacccac tgcttactgg cttatcgaaa    660
ttgcggccgc atgcatcatc accatcacca tatgtttccc atgcaattca ccaactcagc    720
ctatcgccag atggagccca tgttcgcacc ggcttctcga ggacaagtac agccgtatcg    780
gccgcgcaca aagcgccgcc aagagccgca agtcggcaac gctgctattg ctgccctcgc    840
gaaccagatg agcgcgctcc agctgcaggt ggctggactt gccggccagg caagggtgga    900
ccgtcgtgga ccgagacgtg ttcagaagaa caagcagaag aagaagaact cttccaacgg    960 agaaaaccc aaggagaaga agaagaagca aaaacaacag gagaagaaag ggagcggcgg   1020
tgaaaaagtc aagaagccac ggaaccggcc cgggaaggag gtaaggatct ccgtaaagcg   1080
tgcccgacag agcaccttcc ccgtgtacca tgacggtgcc atatccggct atgcggtgct   1140
gattggctcc cgcgtgttta agccagcgca cgtgaagggt aagatcgacc accccgaact   1200
ggcggacatc aagttccagg tcgccgagga catggacctc gaagcagccg cataccccaa   1260
gagcatgcga gaccaagcgg ctgaaccagc aaccatgacg gatggagtgt acaactggga   1320
atacggcact atcagagtgg aggacaacgt cgtgatcgat gcgagcggca gaggcaagcc   1380
gggtgacagc ggcagggcca tcaccgacaa ctcaggaaag gttgtcggta tcgtcctcgg   1440
aggaggaccc gatggtaggc gcacacgtct ctccgtgata ggtttcgaca agaagctgaa   1500
ggccagagag atcgcctaca gcgaggccat cccttggaca cgcgcaccag ctctcctgct   1560
gctgcccatg gtcatcgcct gtacctacaa ctccaacacc tttgactgct ccaaaccgtc   1620
ctgccaggac tgttgcatta ctgctgaacc aaagaaggcc atgactatgc tgaaggacaa   1680
cctgaatgac ccgaattact gggacctgct tattgccgtc accacctgca gttccgcccg   1740
aaaaaagagg gctgtgtcta cgtcgcctgc cgccgcttac gacacacaaa ttctcgccgc   1800
ccacgcagct gcctccccgt atagggcgta ctgccccgat tgtgacggaa ctgcctgcat   1860
ctcgccgata gctatcgacg aggtggtaag tagcggtagt gaccacgtcc ttcgcatccg   1920
ggtcggttct caatcgggag tgaccgctaa aggcggtgcg gcgggtgaaa cctctctgcg   1980
atacctggga agggacggta aggttcacgc cgcggacaac acgcggctcg tggtgcgcac   2040
cactgcaaag tgtgacgtgc tgcaggccac tggccactac attctggcca actgcccagt   2100
ggggcagagt ctcactgttg cggccacact ggacggcacc cggcatcaat gtaccacggt   2160
tttcgaacat caagtaacgg agaagttcac aagagaacgc agcaagggcc accacctgtc   2220
cgatctgacc aagaaatgca ccaggttttc caccaccccg aagaaatccg cgctctatct   2280
cgtggatgtg tatgacgctc tgccgatttc tgtagagatc agcaccgtgg tgacatgcaa   2340
cgaaagtcag tgcacagtga gggtgccacc cggtaccaca gtgaaattcg ataagaagtg   2400
caagagcgct gcccaagcga ccgtcacctt caccagcggc tcccagacgt ttacgtgcga   2460
ggagccggtc ctaacggccg ccagtatcac ccagggcaag ccgcacctta gatcgtcaat   2520
gctgcccagc ggaggcaaag aggtgaaagc gaggattcca ttcccgttcc cgccagagac   2580
tgcgacctgc agagtgagtg tcgccccact gccatcgatc acctatgagg aaagcgatgt   2640
cctgctggcc ggcactgcga aatacccgt gctgctaact acacggaatc ttggttttcca   2700 tagcaacgcc acatccgaat ggatccaggg taagtacctg cgccgcatcc cggtcacgcc   2760
ccaagggatc gaactaatgt gggaaaacaa cgcaccgctg cacttctggt catctgtcag   2820
gtacgcatct ggggacgccg acgcgtaccc ctgggaactt ctggtgcacc acatcaagca   2880
```

```
ccatccggag tatgcgtggg cgtttgtagg agttgcatgt ggcctactgg ccgttgcagc   2940
atgcgtgttt gcgtgcgcat gcaacagggt gcggtactct ctgcttgcca acacgttcaa   3000
cccgaaccca ccaccactga ccgcactgac tgcagcactg tgctgcatac ctggggctcg   3060
cgcggatcaa ccctacctgg acatcattgc ctacttgtgg accaacagca aagtggcctt   3120
cgggctgcaa tgcgcggcgc ccgtggcttg tatgctcatc gtcacatacg cccttagaca   3180
ctgcagattg tgctgcaagt ctttttttagg ggtaagaggg tggtcggctc tgttggtcat   3240
ccttgcgtat gtacagagct gcaagagcta cgaacacacc gtggtggtcc caatggatcc   3300
aagagcccg tcgtacgagg cggtgataaa ccggaatggg tatgaccccc tgaagctgac   3360
catcgcagtg aatttcaccg tcatctcacc aactacggct ctggaatact ggacctgtgc   3420
aggagtccct gtcgtcgagc cgccccatgt gggctgctgc acgtcagtgt cctgccccac   3480
cgacctctcc acgctgcacg cgttcaccgg caaagccgtc tccgacgtgc actgcgatgt   3540
gcacacaaac gtgtacccct tgttgtgggg tgcggctcac tgcttttgtt ccactgaaaa   3600
cacgcaggtc agcgctgtgg ccgccaccgt ttctgagttc tgcgctcagg acgcagaacg   3660
cgccgaggcg ttcagcgttc acagcagctc agtcactgca gagatcctgg tgacgcttgg   3720
tgaagtggtg acggcagtcc acgtttacgt ggacggggta acatcagcca ggggtaccga   3780
cctcaagatc gtggctggcc caataacaac tgactactcc ccgttttgatc gcaaagtagt   3840
ccgtatcagc gaagaggtct ataactacga ctggcctcct tacggggctg gtcgaccagg   3900
cacattcgga gacattcaag ctaggtcaac caactatgtc aaacccaatg atctgtacgg   3960
ggatatcggg attgaagtac tgcagccgac taatgaccac gtgcacgtgg cttacacgta   4020
tacgacctcc gggttactgc gttggttgca ggacgctccg aaaccactca gtgtcacagc   4080
accgcacggt tgtaagatca gtgctaaccc gctcctggcc ctcgattgtg gggttggtgc   4140
cgtccccatg tccatcaaca ttccggacgc gaagttcacc cgcaaattaa aggatccgaa   4200
accatcggcc ctgaaatgcg tggtggacag ttgcgagtac ggggtggact acggggcgc   4260
cgccacgatc acctacgagg ccacgaggc tgggaagtgc gggatccatt ccctgacacc   4320
aggagtccct ctgagaacat cagtggttga agtagttgcc ggcgctaata ccgtcaaaac   4380
gaccttctcc tcacccacgc ccgaggtcac actcgaggta gagatctgtt cggcaatagt   4440
gaagtgcgcc agtgagtgca ctccaccgaa ggaacacgta gtcgcagcca ggcctcgcca   4500
tggcagcgac actggaggct acatctccgg gcccgcaatg cgctgggccg agggattgt   4560
agggaccta gtggtcctgt tcctcatcct tgccgtcacc tactgcgtgg tgaagaagtg   4620
ccgctctaaa agaatccgga tagtcaagag ctaaattccg gtatacaaat tgcgaattcg   4680
agctcccggg taccatggca tgcatcgata gatctcgagt ctagactaga gctcgctgat   4740
cagcctcgac tgtgccttct agttgccagc catctgttgt ttgcccctcc ccgtgccttt   4800
ccttgaccct ggaaggtgcc actcccactg tcctttccta ataaaatgag gaaattgcat   4860
cgcattgtct gagtaggtgt cattctattc tggggggtgg ggtggggcag gacagcaagg   4920
gggaggattg ggaagacaat agcaggcatg ctggggaagg cctcggacta gtggcgtaat   4980
catggtcata gctgtttcct gtgtgaaatt gttatccgct cacaattcca cacaacatac   5040
gagccgcgga agcataaagt gtaaagcctg ggtgcctaa tgagtgagct aactcacatt   5100
aattgcgttg cgctcactgc ccgctttcca gtcgggaaac ctgtcgtgcc agctgcatta   5160
atgaatcggc caacgcgcgg ggagaggcgg tttgcgtatt gggcgctctt ccgcttcctc   5220
gctcactgac tcgctgcgct cggtcgttcg gctgcggcga gcggtatcag ctcactcaaa   5280
```

-continued

```
ggcggtaata cggttatcca cagaatcagg ggataacgca ggaaagaaca tgtgagcaaa    5340
aggccagcaa aaggccagga accgtaaaaa ggccgcgttg ctggcgtttt tccataggct    5400
ccgcccccct gacgagcatc acaaaaatcg acgctcaagt cagaggtggc gaaacccgac    5460
aggactataa agataccagg cgtttccccc tggaagctcc ctcgtgcgct ctcctgttcc    5520
gaccctgccg cttaccggat acctgtccgc ctttctccct tcgggaagcg tggcgctttc    5580
tcatagctca cgctgtaggt atctcagttc ggtgtaggtc gttcgctcca agctgggctg    5640
tgtgcacgaa ccccccgttc agcccgaccg ctgcgcctta tccggtaact atcgtcttga    5700
gtccaacccg gtaagacacg acttatcgcc actggcagca gccactggta acaggattag    5760
cagagcgagg tatgtaggcg gtgctacaga gttcttgaag tggtggccta actacggcta    5820
cactagaaga acagtatttg gtatctgcgc tctgctgaag ccagttacct tcggaaaaag    5880
agttggtagc tcttgatccg gcaaacaaac caccgctggt agcggtggtt ttttt gtttg    5940 caagcagcag attacgcgca gaaaaaagg atcctttga tcttttctac    6000 ggggtctgac gctcagtgga acgaaaactc acgttaaggg attttggtca tgagcttgcg    6060
ccgtcccgtc aagtcagcgt aatgctctgc cagtgttaca accaattaac caattctgat    6120
tagaaaaact catcgagcat caaatgaaac tgcaatttat tcatatcagg attatcaata    6180 ccatatttt gaaaagccg tttctgtaat gaaggagaaa actcaccgag gcagttccat    6240
aggatggcaa gatcctggta tcggtctgcg attccgactc gtccaacatc aatacaacct    6300
attaatttcc cctcgtcaaa aataaggtta tcaagtgaga aatcaccatg agtgacgact    6360
gaatccggtg agaatggcaa aagtttatgc atttctttcc agacttgttc aacaggccag    6420
ccattacgct cgtcatcaaa atcactcgca tcaaccaaac cgttattcat tcgtgattgc    6480
gcctgagcga gacgaaatac gcgatcgctg ttaaaaggac aattacaaac aggaatcgaa    6540
tgcaaccggc gcaggaacac tgccagcgca tcaacaatat tttcacctga atcaggatat    6600
tcttctaata cctggaatgc tgttttttccg gggatcgcag tggtgagtaa ccatgcatca    6660
tcaggagtac ggataaaatg cttgatggtc ggaagaggca taaattccgt cagccagttt    6720
agtctgacca tctcatctgt aacatcattg gcaacgctac ctttgccatg tttcagaaac    6780
aactctggcg catcgggctt cccatacaag cgatagattg tcgcacctga ttgcccgaca    6840
ttatcgcgag cccatttata cccatataaa tcagcatcca tgttggaatt taatcgcggc    6900
ctcgacgttt cccgttgaat atggctcata acaccccttg tattactgtt tatgtaagca    6960
gacagtttta ttgttcatga tgatatattt ttatcttgtg caatgtaaca tcagagattt    7020
tgagacacaa cgtggctttc ccccccccc ccatgacatt aacctataaa aataggcgta    7080
tcacgaggcc ctttcgtctc gcgcgtttcg gtgatgacgg tgaaaacctc tgacacatgc    7140
agctcccgga gacggtcaca gcttgtctgt aagcggatgc cgggagcaga caagcccgtc    7200
agggcgcgtc agcgggtgtt ggcgggtgtc ggggctggct taactatgcg gcatcagagc    7260
agattgtact gagagtgcac cataaaattg taaacgttaa tattttgtta aaattcgcgt    7320 taaattttg ttaaatcagc tcattttta accaatagac cgaaatcggc aaaatccctt    7380
ataaatcaaa agaatagccc gagatagagt tgagtgttgt tccagtttgg aacaagagtc    7440
cactattaaa gaacgtggac tccaacgtca agggcgaaa accgtctat cagggcgatg    7500 gcccaccccg atttagagct tgacggggaa agccggcgaa cgtggcgaga aggaaggga    7560 agaaagcgaa aggagcgggc gctaaggcgc tggcaagtgt agcggtcacg ctgcgcgtaa    7620
ccaccacacc cgccgcgctt aatgcgccgc tacagggcgc gtactatggt tgctttgacg    7680
```

```
tatgcggtgt gaaataccgc acagatgcgt aaggagaaaa taccgcatca ggcgccattc    7740
gccattcagg ctgcgcaact gttgggaagg gcgatcggtg cgggcctctt cgctattacg    7800
ccagctggcg aaaggtggat gtgctgcaag gcgattaagt tgggtaacgc cagggttttc    7860
ccagtcacga cgttgtaaaa cgacggccag tgaattgtaa tacgactcac tatagggcga    7920
attggggatc gatccactag tt                                              7942
```

<210> SEQ ID NO 4
<211> LENGTH: 1327
<212> TYPE: PRT
<213> ORGANISM: SPDV

<400> SEQUENCE: 4

```
Met His His His His His Met Phe Pro Met Gln Phe Thr Asn Ser
1               5                   10                  15

Ala Tyr Arg Gln Met Glu Pro Met Phe Ala Pro Ala Ser Arg Gly Gln
            20                  25                  30

Val Gln Pro Tyr Arg Pro Arg Thr Lys Arg Arg Gln Glu Pro Gln Val
        35                  40                  45

Gly Asn Ala Ala Ile Ala Ala Leu Ala Asn Gln Met Ser Ala Leu Gln
    50                  55                  60

Leu Gln Val Ala Gly Leu Ala Gly Gln Ala Arg Val Asp Arg Arg Gly
65                  70                  75                  80

Pro Arg Arg Val Gln Lys Asn Lys Gln Lys Lys Asn Ser Ser Asn
            85                  90                  95

Gly Glu Lys Pro Lys Glu Lys Lys Lys Gln Lys Gln Gln Glu Lys
        100                 105                 110

Lys Gly Ser Gly Gly Glu Lys Val Lys Lys Pro Arg Asn Arg Pro Gly
    115                 120                 125

Lys Glu Val Arg Ile Ser Val Lys Arg Ala Arg Gln Ser Thr Phe Pro
130                 135                 140

Val Tyr His Asp Gly Ala Ile Ser Gly Tyr Ala Val Leu Ile Gly Ser
145                 150                 155                 160

Arg Val Phe Lys Pro Ala His Val Lys Gly Lys Ile Asp His Pro Glu
            165                 170                 175

Leu Ala Asp Ile Lys Phe Gln Val Ala Glu Asp Met Asp Leu Glu Ala
        180                 185                 190

Ala Ala Tyr Pro Lys Ser Met Arg Asp Gln Ala Ala Glu Pro Ala Thr
    195                 200                 205

Met Thr Asp Gly Val Tyr Asn Trp Glu Tyr Gly Thr Ile Arg Val Glu
210                 215                 220

Asp Asn Val Val Ile Asp Ala Ser Gly Arg Gly Lys Pro Gly Asp Ser
225                 230                 235                 240

Gly Arg Ala Ile Thr Asp Asn Ser Gly Lys Val Val Gly Ile Val Leu
            245                 250                 255

Gly Gly Gly Pro Asp Gly Arg Arg Thr Arg Leu Ser Val Ile Gly Phe
        260                 265                 270

Asp Lys Lys Leu Lys Ala Arg Glu Ile Ala Tyr Ser Glu Ala Ile Pro
    275                 280                 285

Trp Thr Arg Ala Pro Ala Leu Leu Leu Leu Pro Met Val Ile Ala Cys
290                 295                 300

Thr Tyr Asn Ser Asn Thr Phe Asp Cys Ser Lys Pro Ser Cys Gln Asp
305                 310                 315                 320
```

```
Cys Cys Ile Thr Ala Glu Pro Lys Lys Ala Met Thr Met Leu Lys Asp
            325                 330                 335

Asn Leu Asn Asp Pro Asn Tyr Trp Asp Leu Leu Ile Ala Val Thr Thr
        340                 345                 350

Cys Ser Ser Ala Arg Lys Lys Arg Ala Val Ser Thr Ser Pro Ala Ala
    355                 360                 365

Ala Tyr Asp Thr Gln Ile Leu Ala Ala His Ala Ala Ser Pro Tyr
370                 375                 380

Arg Ala Tyr Cys Pro Asp Cys Asp Gly Thr Ala Cys Ile Ser Pro Ile
385                 390                 395                 400

Ala Ile Asp Glu Val Val Ser Ser Gly Ser Asp His Val Leu Arg Ile
                405                 410                 415

Arg Val Gly Ser Gln Ser Gly Val Thr Ala Lys Gly Gly Ala Ala Gly
                420                 425                 430

Glu Thr Ser Leu Arg Tyr Leu Gly Arg Asp Gly Lys Val His Ala Ala
                435                 440                 445

Asp Asn Thr Arg Leu Val Val Arg Thr Thr Ala Lys Cys Asp Val Leu
        450                 455                 460

Gln Ala Thr Gly His Tyr Ile Leu Ala Asn Cys Pro Val Gly Gln Ser
465                 470                 475                 480

Leu Thr Val Ala Ala Thr Leu Asp Gly Thr Arg His Gln Cys Thr Thr
                485                 490                 495

Val Phe Glu His Gln Val Thr Glu Lys Phe Thr Arg Gly Arg Ser Lys
                500                 505                 510

Gly His His Leu Ser Asp Leu Thr Lys Lys Cys Thr Arg Phe Ser Thr
                515                 520                 525

Thr Pro Lys Lys Ser Ala Leu Tyr Leu Val Asp Val Tyr Asp Ala Leu
        530                 535                 540

Pro Ile Ser Val Glu Ile Ser Thr Val Val Thr Cys Asn Glu Ser Gln
545                 550                 555                 560

Cys Thr Val Arg Val Pro Pro Gly Thr Thr Val Lys Phe Asp Lys Lys
                565                 570                 575

Cys Lys Ser Ala Ala Gln Ala Thr Val Thr Phe Thr Ser Gly Ser Gln
                580                 585                 590

Thr Phe Thr Cys Glu Glu Pro Val Leu Thr Ala Ala Ser Ile Thr Gln
                595                 600                 605

Gly Lys Pro His Leu Arg Ser Ser Met Leu Pro Ser Gly Gly Lys Glu
            610                 615                 620

Val Lys Ala Arg Ile Pro Phe Pro Phe Pro Pro Glu Thr Ala Thr Cys
625                 630                 635                 640

Arg Val Ser Val Ala Pro Leu Pro Ser Ile Thr Tyr Glu Glu Ser Asp
                645                 650                 655

Val Leu Leu Ala Gly Thr Ala Lys Tyr Pro Val Leu Leu Thr Thr Arg
                660                 665                 670

Asn Leu Gly Phe His Ser Asn Ala Thr Ser Glu Trp Ile Gln Gly Lys
            675                 680                 685

Tyr Leu Arg Arg Ile Pro Val Thr Pro Gln Gly Ile Glu Leu Met Trp
        690                 695                 700

Gly Asn Asn Ala Pro Leu His Phe Trp Ser Ser Val Arg Tyr Ala Ser
705                 710                 715                 720

Gly Asp Ala Asp Ala Tyr Pro Trp Glu Leu Leu Val His His Ile Lys
                725                 730                 735
```

-continued

His His Pro Glu Tyr Ala Trp Ala Phe Val Gly Val Ala Cys Gly Leu
            740                 745                 750

Leu Ala Val Ala Ala Cys Val Phe Ala Cys Ala Cys Asn Arg Val Arg
    755                 760                 765

Tyr Ser Leu Leu Ala Asn Thr Phe Asn Pro Asn Pro Pro Leu Thr
770                 775                 780

Ala Leu Thr Ala Ala Leu Cys Cys Ile Pro Gly Ala Arg Ala Asp Gln
785                 790                 795                 800

Pro Tyr Leu Asp Ile Ile Ala Tyr Leu Trp Thr Asn Ser Lys Val Ala
                805                 810                 815

Phe Gly Leu Gln Cys Ala Ala Pro Val Ala Cys Met Leu Ile Val Thr
            820                 825                 830

Tyr Ala Leu Arg His Cys Arg Leu Cys Cys Lys Ser Phe Leu Gly Val
            835                 840                 845

Arg Gly Trp Ser Ala Leu Leu Val Ile Leu Ala Tyr Val Gln Ser Cys
            850                 855                 860

Lys Ser Tyr Glu His Thr Val Val Pro Met Asp Pro Arg Ala Pro
865                 870                 875                 880

Ser Tyr Glu Ala Val Ile Asn Arg Asn Gly Tyr Asp Pro Leu Lys Leu
                885                 890                 895

Thr Ile Ala Val Asn Phe Thr Val Ile Ser Pro Thr Thr Ala Leu Glu
                900                 905                 910

Tyr Trp Thr Cys Ala Gly Val Pro Val Glu Pro Pro His Val Gly
            915                 920                 925

Cys Cys Thr Ser Val Ser Cys Pro Thr Asp Leu Ser Thr Leu His Ala
930                 935                 940

Phe Thr Gly Lys Ala Val Ser Asp Val His Cys Asp Val His Thr Asn
945                 950                 955                 960

Val Tyr Pro Leu Leu Trp Gly Ala Ala His Cys Phe Cys Ser Thr Glu
                965                 970                 975

Asn Thr Gln Val Ser Ala Val Ala Ala Thr Val Ser Glu Phe Cys Ala
            980                 985                 990

Gln Asp Ala Glu Arg Ala Glu Ala  Phe Ser Val His Ser  Ser Ser Val
            995                 1000                1005

Thr Ala  Glu Ile Leu Val Thr  Leu Gly Glu Val Val  Thr Ala Val
    1010                1015                1020

His Val  Tyr Val Asp Gly Val  Thr Ser Ala Arg Gly  Thr Asp Leu
    1025                1030                1035

Lys Ile  Val Ala Gly Pro Ile  Thr Thr Asp Tyr Ser  Pro Phe Asp
    1040                1045                1050

Arg Lys  Val Val Arg Ile Ser  Glu Glu Val Tyr Asn  Tyr Asp Trp
    1055                1060                1065

Pro Pro  Tyr Gly Ala Gly Arg  Pro Gly Thr Phe Gly  Asp Ile Gln
    1070                1075                1080

Ala Arg  Ser Thr Asn Tyr Val  Lys Pro Asn Asp Leu  Tyr Gly Asp
    1085                1090                1095

Ile Gly  Ile Glu Val Leu Gln  Pro Thr Asn Asp His  Val His Val
    1100                1105                1110

Ala Tyr  Thr Tyr Thr Thr Ser  Gly Leu Leu Arg Trp  Leu Gln Asp
    1115                1120                1125

Ala Pro  Lys Pro Leu Ser Val  Thr Ala Pro His Gly  Cys Lys Ile
    1130                1135                1140

-continued

Ser Ala Asn Pro Leu Leu Ala Leu Asp Cys Gly Val Gly Ala Val
                1145                1150                1155

Pro Met Ser Ile Asn Ile Pro Asp Ala Lys Phe Thr Arg Lys Leu
    1160                1165                1170

Lys Asp Pro Lys Pro Ser Ala Leu Lys Cys Val Asp Ser Cys
    1175                1180                1185

Glu Tyr Gly Val Asp Tyr Gly Ala Ala Thr Ile Thr Tyr Glu
    1190                1195                1200

Gly His Glu Ala Gly Lys Cys Gly Ile His Ser Leu Thr Pro Gly
    1205                1210                1215

Val Pro Leu Arg Thr Ser Val Glu Val Val Ala Gly Ala Asn
    1220                1225                1230

Thr Val Lys Thr Thr Phe Ser Ser Pro Thr Pro Glu Val Thr Leu
    1235                1240                1245

Glu Val Glu Ile Cys Ser Ala Ile Val Lys Cys Ala Ser Glu Cys
    1250                1255                1260

Thr Pro Pro Lys Glu His Val Val Ala Ala Arg Pro Arg His Gly
    1265                1270                1275

Ser Asp Thr Gly Gly Tyr Ile Ser Gly Pro Ala Met Arg Trp Ala
    1280                1285                1290

Gly Gly Ile Val Gly Thr Leu Val Val Leu Phe Leu Ile Leu Ala
    1295                1300                1305

Val Thr Tyr Cys Val Val Lys Lys Cys Arg Ser Lys Arg Ile Arg
    1310                1315                1320

Ile Val Lys Ser
    1325

<210> SEQ ID NO 5
<211> LENGTH: 1320
<212> TYPE: PRT
<213> ORGANISM: SPDV

<400> SEQUENCE: 5

Met Phe Pro Met Gln Phe Thr Asn Ser Ala Tyr Arg Gln Met Glu Pro
1               5                   10                  15

Met Phe Ala Pro Ala Ser Arg Gly Gln Val Gln Pro Tyr Arg Pro Arg
                20                  25                  30

Thr Lys Arg Arg Gln Glu Pro Gln Val Gly Asn Ala Ala Ile Ala Ala
            35                  40                  45

Leu Ala Asn Gln Met Ser Ala Leu Gln Leu Gln Val Ala Gly Leu Ala
        50                  55                  60

Gly Gln Ala Arg Val Asp Arg Arg Gly Pro Arg Arg Val Gln Lys Asn
65                  70                  75                  80

Lys Gln Lys Lys Lys Asn Ser Ser Asn Gly Glu Lys Pro Lys Glu Lys
                85                  90                  95

Lys Lys Lys Gln Lys Gln Gln Glu Lys Lys Gly Ser Gly Gly Glu Lys
            100                 105                 110

Val Lys Lys Pro Arg Asn Arg Pro Gly Lys Glu Val Arg Ile Ser Val
        115                 120                 125

Lys Arg Ala Arg Gln Ser Thr Phe Pro Val Tyr His Asp Gly Ala Ile
    130                 135                 140

Ser Gly Tyr Ala Val Leu Ile Gly Ser Arg Val Phe Lys Pro Ala His
145                 150                 155                 160

Val Lys Gly Lys Ile Asp His Pro Glu Leu Ala Asp Ile Lys Phe Gln
                165                 170                 175

-continued

Val Ala Glu Asp Met Asp Leu Glu Ala Ala Tyr Pro Lys Ser Met
        180                 185                 190

Arg Asp Gln Ala Ala Glu Pro Ala Thr Met Thr Asp Gly Val Tyr Asn
            195                 200                 205

Trp Glu Tyr Gly Thr Ile Arg Val Glu Asp Asn Val Val Ile Asp Ala
    210                 215                 220

Ser Gly Arg Gly Lys Pro Gly Asp Ser Gly Arg Ala Ile Thr Asp Asn
225                 230                 235                 240

Ser Gly Lys Val Val Gly Ile Val Leu Gly Gly Gly Pro Asp Gly Arg
                245                 250                 255

Arg Thr Arg Leu Ser Val Ile Gly Phe Asp Lys Lys Leu Lys Ala Arg
        260                 265                 270

Glu Ile Ala Tyr Ser Glu Ala Ile Pro Trp Thr Arg Ala Pro Ala Leu
            275                 280                 285

Leu Leu Leu Pro Met Val Ile Ala Cys Thr Tyr Asn Ser Asn Thr Phe
    290                 295                 300

Asp Cys Ser Lys Pro Ser Cys Gln Asp Cys Cys Ile Thr Ala Glu Pro
305                 310                 315                 320

Lys Lys Ala Met Thr Met Leu Lys Asp Asn Leu Asn Asp Pro Asn Tyr
                325                 330                 335

Trp Asp Leu Leu Ile Ala Val Thr Thr Cys Ser Ser Ala Arg Lys Lys
        340                 345                 350

Arg Ala Val Ser Thr Ser Pro Ala Ala Tyr Asp Thr Gln Ile Leu
            355                 360                 365

Ala Ala His Ala Ala Ala Ser Pro Tyr Arg Ala Tyr Cys Pro Asp Cys
    370                 375                 380

Asp Gly Thr Ala Cys Ile Ser Pro Ile Ala Ile Asp Glu Val Val Ser
385                 390                 395                 400

Ser Gly Ser Asp His Val Leu Arg Ile Arg Val Gly Ser Gln Ser Gly
                405                 410                 415

Val Thr Ala Lys Gly Gly Ala Ala Gly Glu Thr Ser Leu Arg Tyr Leu
        420                 425                 430

Gly Arg Asp Gly Lys Val His Ala Ala Asp Asn Thr Arg Leu Val Val
            435                 440                 445

Arg Thr Thr Ala Lys Cys Asp Val Leu Gln Ala Thr Gly His Tyr Ile
    450                 455                 460

Leu Ala Asn Cys Pro Val Gly Gln Ser Leu Thr Val Ala Ala Thr Leu
465                 470                 475                 480

Asp Gly Thr Arg His Gln Cys Thr Thr Val Phe Glu His Gln Val Thr
                485                 490                 495

Glu Lys Phe Thr Arg Glu Arg Ser Lys Gly His His Leu Ser Asp Leu
        500                 505                 510

Thr Lys Lys Cys Thr Arg Phe Ser Thr Pro Lys Lys Ser Ala Leu
            515                 520                 525

Tyr Leu Val Asp Val Tyr Asp Ala Leu Pro Ile Ser Val Glu Ile Ser
    530                 535                 540

Thr Val Val Thr Cys Asn Glu Ser Gln Cys Thr Val Arg Val Pro Pro
545                 550                 555                 560

Gly Thr Thr Val Lys Phe Asp Lys Lys Cys Lys Ser Ala Ala Gln Ala
                565                 570                 575

Thr Val Thr Phe Thr Ser Gly Ser Gln Thr Phe Thr Cys Glu Glu Pro
        580                 585                 590

Val Leu Thr Ala Ala Ser Ile Thr Gln Gly Lys Pro His Leu Arg Ser
            595                 600                 605

Ser Met Leu Pro Ser Gly Gly Lys Glu Val Lys Ala Arg Ile Pro Phe
            610                 615                 620

Pro Phe Pro Pro Glu Thr Ala Thr Cys Arg Val Ser Val Ala Pro Leu
625                 630                 635                 640

Pro Ser Ile Thr Tyr Glu Glu Ser Asp Val Leu Leu Ala Gly Thr Ala
            645                 650                 655

Lys Tyr Pro Val Leu Leu Thr Thr Arg Asn Leu Gly Phe His Ser Asn
            660                 665                 670

Ala Thr Ser Glu Trp Ile Gln Gly Lys Tyr Leu Arg Arg Ile Pro Val
            675                 680                 685

Thr Pro Gln Gly Ile Glu Leu Met Trp Gly Asn Asn Ala Pro Leu His
            690                 695                 700

Phe Trp Ser Ser Val Arg Tyr Ala Ser Gly Asp Ala Asp Ala Tyr Pro
705                 710                 715                 720

Trp Glu Leu Leu Val His His Ile Lys His His Pro Glu Tyr Ala Trp
            725                 730                 735

Ala Phe Val Gly Val Ala Cys Gly Leu Leu Ala Val Ala Ala Cys Val
            740                 745                 750

Phe Ala Cys Ala Cys Asn Arg Val Arg Tyr Ser Leu Leu Ala Asn Thr
            755                 760                 765

Phe Asn Pro Asn Pro Pro Leu Thr Ala Leu Thr Ala Ala Leu Cys
            770                 775                 780

Cys Ile Pro Gly Ala Arg Ala Asp Gln Pro Tyr Leu Asp Ile Ile Ala
785                 790                 795                 800

Tyr Leu Trp Thr Asn Ser Lys Val Ala Phe Gly Leu Gln Cys Ala Ala
            805                 810                 815

Pro Val Ala Cys Met Leu Ile Val Thr Tyr Ala Leu Arg His Cys Arg
            820                 825                 830

Leu Cys Cys Lys Ser Phe Leu Gly Val Arg Gly Trp Ser Ala Leu Leu
            835                 840                 845

Val Ile Leu Ala Tyr Val Gln Ser Cys Lys Ser Tyr Glu His Thr Val
            850                 855                 860

Val Val Pro Met Asp Pro Arg Ala Pro Ser Tyr Glu Ala Val Ile Asn
865                 870                 875                 880

Arg Asn Gly Tyr Asp Pro Leu Lys Leu Thr Ile Ala Val Asn Phe Thr
            885                 890                 895

Val Ile Ser Pro Thr Thr Ala Leu Glu Tyr Trp Thr Cys Ala Gly Val
            900                 905                 910

Pro Val Val Glu Pro Pro His Val Gly Cys Cys Thr Ser Val Ser Cys
            915                 920                 925

Pro Thr Asp Leu Ser Thr Leu His Ala Phe Thr Gly Lys Ala Val Ser
            930                 935                 940

Asp Val His Cys Asp Val His Thr Asn Val Tyr Pro Leu Leu Trp Gly
945                 950                 955                 960

Ala Ala His Cys Phe Cys Ser Thr Glu Asn Thr Gln Val Ser Ala Val
            965                 970                 975

Ala Ala Thr Val Ser Glu Phe Cys Ala Gln Asp Ala Glu Arg Ala Glu
            980                 985                 990

Ala Phe Ser Val His Ser Ser Val Thr Ala Glu Ile Leu Val Thr
            995                 1000                1005

```
Leu Gly Glu Val Val Thr Ala Val His Val Tyr Val Asp Gly Val
    1010                1015                1020

Thr Ser Ala Arg Gly Thr Asp Leu Lys Ile Val Ala Gly Pro Ile
    1025                1030                1035

Thr Thr Asp Tyr Ser Pro Phe Asp Arg Lys Val Val Arg Ile Ser
    1040                1045                1050

Glu Glu Val Tyr Asn Tyr Asp Trp Pro Pro Tyr Gly Ala Gly Arg
    1055                1060                1065

Pro Gly Thr Phe Gly Asp Ile Gln Ala Arg Ser Thr Asn Tyr Val
    1070                1075                1080

Lys Pro Asn Asp Leu Tyr Gly Asp Ile Gly Ile Glu Val Leu Gln
    1085                1090                1095

Pro Thr Asn Asp His Val His Val Ala Tyr Thr Tyr Thr Thr Ser
    1100                1105                1110

Gly Leu Leu Arg Trp Leu Gln Asp Ala Pro Lys Pro Leu Ser Val
    1115                1120                1125

Thr Ala Pro His Gly Cys Lys Ile Ser Ala Asn Pro Leu Leu Ala
    1130                1135                1140

Leu Asp Cys Gly Val Gly Ala Val Pro Met Ser Ile Asn Ile Pro
    1145                1150                1155

Asp Ala Lys Phe Thr Arg Lys Leu Lys Asp Pro Lys Pro Ser Ala
    1160                1165                1170

Leu Lys Cys Val Val Asp Ser Cys Glu Tyr Gly Val Asp Tyr Gly
    1175                1180                1185

Gly Ala Ala Thr Ile Thr Tyr Glu Gly His Glu Ala Gly Lys Cys
    1190                1195                1200

Gly Ile His Ser Leu Thr Pro Gly Val Pro Leu Arg Thr Ser Val
    1205                1210                1215

Val Glu Val Val Ala Gly Ala Asn Thr Val Lys Thr Thr Phe Ser
    1220                1225                1230

Ser Pro Thr Pro Glu Val Thr Leu Glu Val Glu Ile Cys Ser Ala
    1235                1240                1245

Ile Val Lys Cys Ala Ser Glu Cys Thr Pro Pro Lys Glu His Val
    1250                1255                1260

Val Ala Ala Arg Pro Arg His Gly Ser Asp Thr Gly Gly Tyr Ile
    1265                1270                1275

Ser Gly Pro Ala Met Arg Trp Ala Gly Gly Ile Val Gly Thr Leu
    1280                1285                1290

Val Val Leu Phe Leu Ile Leu Ala Val Thr Tyr Cys Val Val Lys
    1295                1300                1305

Lys Cys Arg Ser Lys Arg Ile Arg Ile Val Lys Ser
    1310                1315                1320

<210> SEQ ID NO 6
<211> LENGTH: 282
<212> TYPE: PRT
<213> ORGANISM: SPDV

<400> SEQUENCE: 6

Met Phe Pro Met Gln Phe Thr Asn Ser Ala Tyr Arg Gln Met Glu Pro
1               5                   10                  15

Met Phe Ala Pro Ala Ser Arg Gly Gln Val Gln Pro Tyr Arg Pro Arg
            20                  25                  30
```

```
Thr Lys Arg Arg Gln Glu Pro Gln Val Gly Asn Ala Ala Ile Ala Ala
         35                  40                  45

Leu Ala Asn Gln Met Ser Ala Leu Gln Leu Val Ala Gly Leu Ala
 50                  55                  60

Gly Gln Ala Arg Val Asp Arg Gly Pro Arg Val Gln Lys Asn
 65                  70                  75                  80

Lys Gln Lys Lys Lys Asn Ser Ser Asn Gly Glu Lys Pro Lys Glu Lys
                     85                  90                  95

Lys Lys Lys Gln Lys Gln Gln Glu Lys Lys Gly Ser Gly Gly Glu Lys
                100                 105                 110

Val Lys Lys Pro Arg Asn Arg Pro Gly Lys Glu Val Arg Ile Ser Val
                115                 120                 125

Lys Arg Ala Arg Gln Ser Thr Phe Pro Val Tyr His Asp Gly Ala Ile
                130                 135                 140

Ser Gly Tyr Ala Val Leu Ile Gly Ser Arg Val Phe Lys Pro Ala His
145                 150                 155                 160

Val Lys Gly Lys Ile Asp His Pro Glu Leu Ala Asp Ile Lys Phe Gln
                165                 170                 175

Val Ala Glu Asp Met Asp Leu Glu Ala Ala Tyr Pro Lys Ser Met
                180                 185                 190

Arg Asp Gln Ala Ala Glu Pro Ala Thr Met Thr Asp Gly Val Tyr Asn
                195                 200                 205

Trp Glu Tyr Gly Thr Ile Arg Val Glu Asp Asn Val Ile Asp Ala
210                 215                 220

Ser Gly Arg Gly Lys Pro Gly Asp Ser Gly Arg Ala Ile Thr Asp Asn
225                 230                 235                 240

Ser Gly Lys Val Val Gly Ile Val Leu Gly Gly Pro Asp Gly Arg
                245                 250                 255

Arg Thr Arg Leu Ser Val Ile Gly Phe Asp Lys Lys Leu Lys Ala Arg
                260                 265                 270

Glu Ile Ala Tyr Ser Glu Ala Ile Pro Trp
                275                 280

<210> SEQ ID NO 7
<211> LENGTH: 71
<212> TYPE: PRT
<213> ORGANISM: SPDV

<400> SEQUENCE: 7

Thr Arg Ala Pro Ala Leu Leu Leu Pro Met Val Ile Ala Cys Thr
1                5                  10                  15

Tyr Asn Ser Asn Thr Phe Asp Cys Ser Lys Pro Ser Cys Gln Asp Cys
                20                  25                  30

Cys Ile Thr Ala Glu Pro Lys Lys Ala Met Thr Met Leu Lys Asp Asn
                35                  40                  45

Leu Asn Asp Pro Asn Tyr Trp Asp Leu Leu Ile Ala Val Thr Thr Cys
 50                  55                  60

Ser Ser Ala Arg Lys Lys Arg
 65                  70

<210> SEQ ID NO 8
<211> LENGTH: 438
<212> TYPE: PRT
<213> ORGANISM: SPDV
```

```
<400> SEQUENCE: 8

Ala Val Ser Thr Ser Pro Ala Ala Tyr Asp Thr Gln Ile Leu Ala
1               5                   10                  15

Ala His Ala Ala Ala Ser Pro Tyr Arg Ala Tyr Cys Pro Asp Cys Asp
                20                  25                  30

Gly Thr Ala Cys Ile Ser Pro Ile Ala Ile Asp Glu Val Val Ser Ser
            35                  40                  45

Gly Ser Asp His Val Leu Arg Ile Arg Val Gly Ser Gln Ser Gly Val
    50                  55                  60

Thr Ala Lys Gly Gly Ala Ala Gly Glu Thr Ser Leu Arg Tyr Leu Gly
65                  70                  75                  80

Arg Asp Gly Lys Val His Ala Ala Asp Asn Thr Arg Leu Val Val Arg
                85                  90                  95

Thr Thr Ala Lys Cys Asp Val Leu Gln Ala Thr Gly His Tyr Ile Leu
            100                 105                 110

Ala Asn Cys Pro Val Gly Gln Ser Leu Thr Val Ala Ala Thr Leu Asp
        115                 120                 125

Gly Thr Arg His Gln Cys Thr Thr Val Phe Glu His Gln Val Thr Glu
130                 135                 140

Lys Phe Thr Arg Glu Arg Ser Lys Gly His His Leu Ser Asp Leu Thr
145                 150                 155                 160

Lys Lys Cys Thr Arg Phe Ser Thr Thr Pro Lys Lys Ser Ala Leu Tyr
                165                 170                 175

Leu Val Asp Val Tyr Asp Ala Leu Pro Ile Ser Val Glu Ile Ser Thr
            180                 185                 190

Val Val Thr Cys Asn Glu Ser Gln Cys Thr Val Arg Val Pro Pro Gly
        195                 200                 205

Thr Thr Val Lys Phe Asp Lys Lys Cys Lys Ser Ala Ala Gln Ala Thr
210                 215                 220

Val Thr Phe Thr Ser Gly Ser Gln Thr Phe Thr Cys Glu Glu Pro Val
225                 230                 235                 240

Leu Thr Ala Ala Ser Ile Thr Gln Gly Lys Pro His Leu Arg Ser Ser
                245                 250                 255

Met Leu Pro Ser Gly Gly Lys Glu Val Lys Ala Arg Ile Pro Phe Pro
            260                 265                 270

Phe Pro Pro Glu Thr Ala Thr Cys Arg Val Ser Val Ala Pro Leu Pro
        275                 280                 285

Ser Ile Thr Tyr Glu Glu Ser Asp Val Leu Leu Ala Gly Thr Ala Lys
    290                 295                 300

Tyr Pro Val Leu Leu Thr Thr Arg Asn Leu Gly Phe His Ser Asn Ala
305                 310                 315                 320

Thr Ser Glu Trp Ile Gln Gly Lys Tyr Leu Arg Arg Ile Pro Val Thr
                325                 330                 335

Pro Gln Gly Ile Glu Leu Met Trp Gly Asn Asn Ala Pro Leu His Phe
            340                 345                 350

Trp Ser Ser Val Arg Tyr Ala Ser Gly Asp Ala Asp Ala Tyr Pro Trp
        355                 360                 365

Glu Leu Leu Val His His Ile Lys His His Pro Glu Tyr Ala Trp Ala
370                 375                 380

Phe Val Gly Val Ala Cys Gly Leu Leu Ala Val Ala Ala Cys Val Phe
385                 390                 395                 400

Ala Cys Ala Cys Asn Arg Val Arg Tyr Ser Leu Leu Ala Asn Thr Phe
                405                 410                 415
```

```
Asn Pro Asn Pro Pro Leu Thr Ala Leu Thr Ala Ala Leu Cys Cys
            420                 425                 430

Ile Pro Gly Ala Arg Ala
            435

<210> SEQ ID NO 9
<211> LENGTH: 46
<212> TYPE: PRT
<213> ORGANISM: SPDV

<400> SEQUENCE: 9

Asp Gln Pro Tyr Leu Asp Ile Ile Ala Tyr Leu Trp Thr Asn Ser Lys
1               5                   10                  15

Val Ala Phe Gly Leu Gln Cys Ala Ala Pro Val Ala Cys Met Leu Ile
            20                  25                  30

Val Thr Tyr Ala Leu Arg His Cys Arg Leu Cys Cys Lys Ser
            35                  40                  45

<210> SEQ ID NO 10
<211> LENGTH: 483
<212> TYPE: PRT
<213> ORGANISM: SPDV

<400> SEQUENCE: 10

Phe Leu Gly Val Arg Gly Trp Ser Ala Leu Leu Val Ile Leu Ala Tyr
1               5                   10                  15

Val Gln Ser Cys Lys Ser Tyr Glu His Thr Val Val Pro Met Asp
            20                  25                  30

Pro Arg Ala Pro Ser Tyr Glu Ala Val Ile Asn Arg Asn Gly Tyr Asp
            35                  40                  45

Pro Leu Lys Leu Thr Ile Ala Val Asn Phe Thr Val Ile Ser Pro Thr
    50                  55                  60

Thr Ala Leu Glu Tyr Trp Thr Cys Ala Gly Val Pro Val Val Glu Pro
65                  70                  75                  80

Pro His Val Gly Cys Cys Thr Ser Val Ser Cys Pro Thr Asp Leu Ser
                85                  90                  95

Thr Leu His Ala Phe Thr Gly Lys Ala Val Ser Asp Val His Cys Asp
            100                 105                 110

Val His Thr Asn Val Tyr Pro Leu Leu Trp Gly Ala Ala His Cys Phe
        115                 120                 125

Cys Ser Thr Glu Asn Thr Gln Val Ser Ala Val Ala Ala Thr Val Ser
    130                 135                 140

Glu Phe Cys Ala Gln Asp Ala Glu Arg Ala Glu Ala Phe Ser Val His
145                 150                 155                 160

Ser Ser Ser Val Thr Ala Glu Ile Leu Val Thr Leu Gly Glu Val Val
                165                 170                 175

Thr Ala Val His Val Tyr Val Asp Gly Val Thr Ser Ala Arg Gly Thr
            180                 185                 190

Asp Leu Lys Ile Val Ala Gly Pro Ile Thr Thr Asp Tyr Ser Pro Phe
        195                 200                 205

Asp Arg Lys Val Val Arg Ile Ser Glu Glu Val Tyr Asn Tyr Asp Trp
    210                 215                 220

Pro Pro Tyr Gly Ala Gly Arg Pro Gly Thr Phe Gly Asp Ile Gln Ala
225                 230                 235                 240

Arg Ser Thr Asn Tyr Val Lys Pro Asn Asp Leu Tyr Gly Asp Ile Gly
                245                 250                 255
```

```
Ile Glu Val Leu Gln Pro Thr Asn Asp His Val His Val Ala Tyr Thr
            260                 265                 270

Tyr Thr Thr Ser Gly Leu Leu Arg Trp Leu Gln Asp Ala Pro Lys Pro
        275                 280                 285

Leu Ser Val Thr Ala Pro His Gly Cys Lys Ile Ser Ala Asn Pro Leu
            290                 295                 300

Leu Ala Leu Asp Cys Gly Val Gly Ala Val Pro Met Ser Ile Asn Ile
305                 310                 315                 320

Pro Asp Ala Lys Phe Thr Arg Lys Leu Lys Asp Pro Lys Pro Ser Ala
                325                 330                 335

Leu Lys Cys Val Val Asp Ser Cys Glu Tyr Gly Val Asp Tyr Gly Gly
            340                 345                 350

Ala Ala Thr Ile Thr Tyr Glu Gly His Glu Ala Gly Lys Cys Gly Ile
            355                 360                 365

His Ser Leu Thr Pro Gly Val Pro Leu Arg Thr Ser Val Val Glu Val
        370                 375                 380

Val Ala Gly Ala Asn Thr Val Lys Thr Thr Phe Ser Ser Pro Thr Pro
385                 390                 395                 400

Glu Val Thr Leu Glu Val Glu Ile Cys Ser Ala Ile Val Lys Cys Ala
                405                 410                 415

Ser Glu Cys Thr Pro Pro Lys Glu His Val Val Ala Ala Arg Pro Arg
            420                 425                 430

His Gly Ser Asp Thr Gly Gly Tyr Ile Ser Gly Pro Ala Met Arg Trp
        435                 440                 445

Ala Gly Gly Ile Val Gly Thr Leu Val Val Leu Phe Leu Ile Leu Ala
    450                 455                 460

Val Thr Tyr Cys Val Val Lys Lys Cys Arg Ser Lys Arg Ile Arg Ile
465                 470                 475                 480

Val Lys Ser

<210> SEQ ID NO 11
<211> LENGTH: 57
<212> TYPE: DNA
<213> ORGANISM: Artificial Sequence
<220> FEATURE:
<223> OTHER INFORMATION: forward primer 1

<400> SEQUENCE: 11
gggcggccgc atgcatcatc accatcacca tatgtttccc atgcaattca ccaactc    57

<210> SEQ ID NO 12
<211> LENGTH: 38
<212> TYPE: DNA
<213> ORGANISM: Artificial Sequence
<220> FEATURE:
<223> OTHER INFORMATION: reverse primer

<400> SEQUENCE: 12
atgaattcgc aatttgtata ccggaattta gctcttga                         38

<210> SEQ ID NO 13
<211> LENGTH: 28
<212> TYPE: DNA
<213> ORGANISM: Artificial Sequence
<220> FEATURE:
<223> OTHER INFORMATION: forward primer 2
```

-continued

```
<400> SEQUENCE: 13
aactatgtca aacccaatga tctgtacg                                          28
```